US009737891B2

(12) United States Patent
TerMaat et al.

(10) Patent No.: US 9,737,891 B2
(45) Date of Patent: Aug. 22, 2017

(54) RAPID THERMOCYCLER SYSTEM FOR RAPID AMPLIFICATION OF NUCLEIC ACIDS AND RELATED METHODS

(75) Inventors: Joel TerMaat, Lincoln, NE (US); Scott E. Whitney, Lincoln, NE (US); Hendrik J. Viljoen, Lincoln, NE (US); Matthew R. Kreifels, Omaha, NE (US)

(73) Assignee: STRECK, INC., Omaha, NE (US)

( * ) Notice: Subject to any disclaimer, the term of this patent is extended or adjusted under 35 U.S.C. 154(b) by 1088 days.

(21) Appl. No.: 13/484,963

(22) Filed: May 31, 2012

(65) Prior Publication Data

US 2012/0308990 A1    Dec. 6, 2012

Related U.S. Application Data

(60) Provisional application No. 61/492,002, filed on Jun. 1, 2011.

(51) Int. Cl.
*C12Q 1/68* (2006.01)
*B01L 7/00* (2006.01)
*G01N 35/00* (2006.01)

(52) U.S. Cl.
CPC ............. *B01L 7/52* (2013.01); *C12Q 1/6844* (2013.01); *B01L 2200/14* (2013.01); *B01L 2300/0627* (2013.01); *B01L 2300/0858* (2013.01); *B01L 2300/1805* (2013.01); *B01L 2300/1822* (2013.01); *G01N 2035/00366* (2013.01)

(58) Field of Classification Search
None
See application file for complete search history.

(56) References Cited

U.S. PATENT DOCUMENTS

| | | |
|---|---|---|
| D255,526 S | 12/1972 | Baum et al. |
| 3,722,502 A | 3/1973 | Besuner et al. |
| 3,911,918 A | 10/1975 | Turner |
| D256,053 S | 7/1980 | Steigerwald |
| 4,528,187 A | 7/1985 | Truglio |
| 4,674,640 A | 6/1987 | Asa et al. |
| 4,683,202 A | 7/1987 | Mullis |
| 4,900,321 A | 2/1990 | Kaufman et al. |
| 4,902,624 A | 2/1990 | Columbus et al. |
| D313,098 S | 12/1990 | Boyd et al. |
| 5,084,041 A | 1/1992 | Oxley et al. |
| D330,428 S | 10/1992 | Lewis et al. |
| D337,261 S | 7/1993 | Sherman |
| 5,225,165 A | 7/1993 | Perlman |
| 5,229,327 A | 7/1993 | Farnworth |
| 5,270,011 A | 12/1993 | Altherr |
| 5,304,487 A | 4/1994 | Wilding et al. |
| 5,333,675 A | 8/1994 | Mullis |
| 5,353,186 A | 10/1994 | Ruoss et al. |
| 5,423,792 A | 6/1995 | Oxley |
| 5,455,175 A | 10/1995 | Wittwer et al. |
| 5,475,610 A | 12/1995 | Atwood et al. |
| 5,508,197 A | 4/1996 | Hansen et al. |
| 5,525,300 A | 6/1996 | Danssaert et al. |
| 5,540,892 A | 7/1996 | Kidd et al. |
| 5,571,479 A | 11/1996 | Koch |
| 5,576,218 A | 11/1996 | Zurck et al. |
| 5,598,349 A | 1/1997 | Elliason et al. |
| 5,604,101 A | 2/1997 | Hanley et al. |
| 5,656,493 A | 8/1997 | Mullis |
| 5,674,742 A | 10/1997 | Nirthrup et al. |
| 5,681,741 A | 10/1997 | Atwood et al. |
| 5,683,659 A | 11/1997 | Hovatter |
| 5,721,136 A | 2/1998 | Finney et al. |
| 5,795,547 A | 8/1998 | Moser et al. |
| 5,832,543 A | 11/1998 | Bosserman |
| 5,856,174 A | 1/1999 | Lipshutz et al. |
| 5,863,791 A | 1/1999 | Baldszunl et al. |
| 5,928,880 A | 7/1999 | Wilding |

(Continued)

FOREIGN PATENT DOCUMENTS

| | | |
|---|---|---|
| DE | 4022792 | 7/1990 |
| DE | 102005038252 | 2/2007 |
| EP | 0 350 675 A2 | 1/1990 |
| EP | 1000661 | 5/2000 |
| EP | 1757367 | 2/2007 |
| EP | 2193845 | 6/2010 |
| WO | 98/43740 | 10/1998 |
| WO | 98/43740 A2 | 10/1998 |
| WO | 01/15680 A1 | 3/2001 |
| WO | 02/41999 | 5/2002 |

(Continued)

OTHER PUBLICATIONS

International Search Report and Written Opinion, for Corresponding PCT Application No. US2009/34446 A1 filed Feb. 19, 2009.
Boshoff-Mostert et al., Crack propagation in catalytic pellets due to thermal stresses. AICHE J. Aug. 1996, 2288-2294, 42.
Chaisson et al., Tuberculosis in Africa—Combating an HIV driven crisis. N. Engl. J. Med., Mar. 13, 2008, 1089-1092, 358(11).
Davies et al., The diagnosis and misdiagnosis of tuberculosis, Int. J. Tuberc. Lung. Dis., Nov. 2008, 1226-1234, 12(11).
Davis et al., The rheological properties of sputum, Biorheology, Apr. 1969, 11-21 6(1).

(Continued)

*Primary Examiner* — Prabha Chunduru
(74) *Attorney, Agent, or Firm* — The Dobrusin Law Firm, P.C.

(57) ABSTRACT

A thermocycling device and method of operating a thermocycler instrument, the instrument including a sample holder, at least one thermal cycling element, and at least one first and second temperature sensors, for causing the sample holder containing the at least one sample to undergo polymerase chain reaction amplification by repeated cycling between at least a denaturation heating stage and an annealing cooling stage. The first temperature corresponding with the temperature of the sample holder is monitored using the at least one first temperature sensor, and a second temperature corresponding with the temperature external of the sample holder is monitored using the at least one second temperature sensor. Based upon the first temperature and the second temperature, the power that is delivered to the at least one thermal cycling element of the instrument is dynamically controlled.

14 Claims, 18 Drawing Sheets

(56) References Cited

U.S. PATENT DOCUMENTS

| | | |
|---|---|---|
| 5,935,858 A | 8/1999 | Herst |
| 5,958,349 A | 9/1999 | Petersen et al. |
| 5,972,716 A | 10/1999 | Ragusa et al. |
| 6,015,534 A | 1/2000 | Atwood |
| D425,625 S | 5/2000 | Niermann |
| 6,140,613 A | 10/2000 | Isuno |
| 6,159,727 A | 12/2000 | Bochkariov |
| 6,174,670 B1* | 1/2001 | Wittwer ............... B01L 3/5082 435/6.1 |
| 6,210,382 B1 | 4/2001 | Hogg |
| 6,210,958 B1 | 4/2001 | Brust et al. |
| 6,303,343 B1 | 10/2001 | Kopf-Sill |
| 6,312,886 B1 | 11/2001 | Lee et al. |
| 6,372,486 B1 | 4/2002 | Fripp |
| 6,374,684 B1 | 4/2002 | Dority |
| 6,472,186 B1 | 10/2002 | Quintanar et al. |
| 6,503,750 B1 | 1/2003 | Benett et al. |
| 6,556,940 B1 | 4/2003 | Tretiakov et al. |
| 6,558,947 B1* | 5/2003 | Lund .................. B01L 3/50851 219/428 |
| 6,645,191 B1 | 11/2003 | Knerr et al. |
| 6,657,169 B2 | 12/2003 | Brown |
| 6,734,401 B2 | 5/2004 | Bedingham et al. |
| 6,780,617 B2 | 8/2004 | Chen |
| 6,783,025 B2 | 8/2004 | Lohn |
| 6,787,338 B2 | 9/2004 | Wittwer et al. |
| 6,814,934 B1 | 11/2004 | Higuchi |
| 6,818,185 B1 | 11/2004 | Petersen et al. |
| 6,875,602 B2 | 4/2005 | Gutierrez |
| 6,881,541 B2 | 4/2005 | Petersen et al. |
| 6,887,693 B2 | 5/2005 | McMillan et al. |
| 6,889,468 B2 | 5/2005 | Bedingham et al. |
| 6,964,862 B2 | 11/2005 | Chen |
| 6,987,253 B2 | 1/2006 | Bedingham et al. |
| 7,051,536 B1 | 5/2006 | Cohen et al. |
| 7,081,600 B2 | 7/2006 | Brown et al. |
| 7,138,254 B2 | 11/2006 | Jovanovich et al. |
| 7,164,077 B2 | 1/2007 | Venkatasubramanian |
| 7,164,107 B2 | 1/2007 | Bedingham et al. |
| 7,189,252 B2 | 3/2007 | Krueger et al. |
| 7,238,321 B2 | 7/2007 | Wittwer et al. |
| 7,255,833 B2 | 8/2007 | Chang et al. |
| 7,295,316 B2 | 11/2007 | Boege et al. |
| 7,422,905 B2 | 9/2008 | Clague et al. |
| 7,435,933 B2 | 10/2008 | Bedingham et al. |
| 7,439,069 B2 | 10/2008 | Nippoldt et al. |
| 7,442,542 B2 | 10/2008 | Miao et al. |
| 7,462,323 B1 | 12/2008 | Chang et al. |
| 7,482,116 B2 | 1/2009 | Birnboim |
| 7,490,976 B2 | 2/2009 | Bucher |
| 7,544,506 B2 | 6/2009 | Breidford et al. |
| 7,578,976 B1 | 8/2009 | Northrup et al. |
| 7,648,095 B2 | 1/2010 | Jagle |
| 7,749,452 B2 | 7/2010 | Brem et al. |
| D621,520 S | 8/2010 | Talmer et al. |
| D621,951 S | 8/2010 | Bucholtz et al. |
| D640,795 S | 6/2011 | Jackson et al. |
| 8,003,370 B2 | 8/2011 | Maltezos et al. |
| 8,008,046 B2 | 8/2011 | Maltezos et al. |
| 2001/0007759 A1* | 7/2001 | Wittwer et al. ............... 435/91.1 |
| 2002/0030044 A1 | 3/2002 | Brown |
| 2002/0086417 A1 | 7/2002 | Chen |
| 2003/0106682 A1* | 6/2003 | Reid .................. B01L 7/52 165/206 |
| 2004/0122559 A1 | 6/2004 | Young |
| 2004/0214315 A1 | 10/2004 | Saluz et al. |
| 2005/0009070 A1 | 1/2005 | Arciniegas |
| 2005/0282270 A1 | 12/2005 | Shin et al. |
| 2006/0088931 A1 | 4/2006 | Ririe |
| 2006/0101830 A1 | 5/2006 | Cohen et al. |
| 2006/0160243 A1 | 7/2006 | Tang et al. |
| 2006/0228264 A1 | 10/2006 | Garvin et al. |
| 2007/0051739 A1 | 3/2007 | Giraud |
| 2007/0111206 A1 | 5/2007 | Tyagi et al. |
| 2007/0128080 A1 | 6/2007 | Lohn |
| 2007/0140919 A1 | 6/2007 | Clarkston et al. |
| 2008/0003649 A1 | 1/2008 | Maltetos et al. |
| 2008/0032347 A1* | 2/2008 | Sarofim .................. B01L 7/52 435/91.2 |
| 2008/0038813 A1 | 2/2008 | Chen |
| 2008/0061429 A1 | 3/2008 | Cohen et al. |
| 2008/0193912 A1 | 8/2008 | Fong et al. |
| 2008/0219889 A1 | 9/2008 | Schaefer et al. |
| 2008/0248534 A1 | 10/2008 | Lim et al. |
| 2009/0011417 A1 | 1/2009 | Maltezos et al. |
| 2009/0023603 A1 | 1/2009 | Selden et al. |
| 2009/0061450 A1 | 3/2009 | Hunter |
| 2009/0120104 A1 | 5/2009 | Federer |
| 2009/0136385 A1 | 5/2009 | Handique et al. |
| 2009/0155838 A1 | 6/2009 | Hale |
| 2009/0162866 A1 | 6/2009 | Birnboim et al. |
| 2009/0275113 A1 | 11/2009 | Maltezos et al. |
| 2010/0285571 A1 | 11/2010 | Coursey et al. |
| 2010/0288059 A1 | 11/2010 | Viljoen et al. |
| 2010/0291536 A1* | 11/2010 | Viljoen et al. .................... 435/4 |

FOREIGN PATENT DOCUMENTS

| | | |
|---|---|---|
| WO | 2004/052527 A1 | 6/2004 |
| WO | 2005113741 | 12/2005 |
| WO | 2006/024879 | 3/2006 |
| WO | 2009/105499 | 8/2009 |
| WO | WO 2009105499 A1 * | 8/2009 ............... B01L 7/52 |
| WO | 2011082415 | 7/2011 |
| WO | 2011086497 | 7/2011 |
| WO | 2011/153244 | 12/2011 |

OTHER PUBLICATIONS

Dziadek et al., Specificity of insertion sequence-based PCR assays for *Mycobacterium tuberculosis* complex, Int. J. Tuberc. Lung. Dis., Jan. 2001, 569-574, 5(6).

El-Hajj et al., Detection of rifampin resistance in *Mycobacterium tuberculosis* in a single tube with molecular beacons, J. Clin. Microbiol., Nov. 2001, 4131-4137, 39(11).

Flores et al., In-house nucleic acid amplification tests for the detection of *Mycobacterium tuberculosis* in sputum specimens: meta-analysis and meta-regression, BMC Microbiol., Oct. 2005, 55, 5.

Global Health Diagnostics Forum, The right tools can save lives, Nature, Dec. 7, 2006, 681, 444.

Greco et al., Current evidence on diagnostic accuracy of commercially based nucleic acid amplification tests for the diagnosis of pulmonary tuberculosis. Thorax, Sep. 2006, 783-790, 61(9).

Griep et al., Kinetics of the DNA polymerase *Pyrococcus kodakaraensis*. Chemical Engineering Science, 2006, 3885-3892, 61.

Keeler et al., Reducing the global burden of tuberculosis: The contribution of improved diagnostics, Nature, Nov. 23, 2006, 49-57, 444 Supp. 1.

Marras et al., Genotyping SNPs with molecular beacons, Methods Mol. Biol. 2003, 111-128, 212.

McEvoy et al., The role of IS6110 in the evolution of *Mycobacterium tuberculosis*, Tuberculosis (Edinb)., Sep. 2007, 393-404, 87(5).

Menzies et al., Risk of tuberculosis infection and disease associated with work in health care settings, Int. J. Tuberc. Lung Dis., Jun. 2007, 593-605, 11(6).

Menzies et al., Tuberculosis among health care workers, N. Engl. J. Med., Jan. 12, 1995, 92-98, 332(2).

Musser, Antimicrobial agent resistance in mycobacteria; genetic insights, Clin. Microbiol. Rev., Oct. 1995, 496-514, 8(4).

Muthupillai et al., Magnetic resonance elastography by direct visualization of propagating acoustic strain waves, Science, Sep. 29, 1995, 1854-1857, 269.

Negi et al., Diagnostic potential of IS6110, 38kDa, 65kDa and 85B sequence-based polymerase chain reaction in the diagnosis of *Mycobacterium tuberculosis* in clinical samples, Indian. J. Med. Microbiol. Jan. 2007, 43-9, 25(1).

(56) References Cited

OTHER PUBLICATIONS

Nielsen et al., Elastic contributions dominate the viscoelastic properties of sputum from cystic fibrosis patient, Biophys. Chem., Dec. 20, 2004, 193-200, 112.
Othman et al., Microscopic magnetic resonance elastography (muMRE), Magnetic Resonance in Medicine, Sep. 2005, 605-615, 54.
Perkins et al., Progress towards improved tuberculosis diagnostics for developing countries, Lancet, Mar. 18, 2006, 942-943, 367.
Ramaswamy et al., Molecular genetic basis of antimicrobial agent resistance in *Mycobacterium tuberculosis*: 1998 update, Tuber. Lung Dis., 1998, 3-29, 79.
Riska et al., Molecular determinants of drug resistance in tuberculosis, Int. J, Tuberc. Lung Dis., Feb. 2000, S4-10, 4(2 Suppl I).
Sarmiento et al., Assessment by meta-analysis of PCR for diagnosis of smear-negative pulmonary tuberculosis, J. Clin. Microbiol., Jul. 2003, 3233-3240, 41(7).
Shah et al., Extensively Drug-Resistant Tuberculosis in the United States 1993-2007, JAMA, Nov. 12, 2008, 2153-2160, 300(18).
Singh et al., Comparative evaluation of FASTPlaque assay with PCR and other conventional in vitro diagnostic methods for the early detection of pulmonary tuberculosis, J. Clin. Lab. Anal., 2008, 367-374, 22(5).
Somoskovi et al., The molecular basis of resistance to isoniazid, rifampin, and pyrazinamide in *Mycobacterium tuberculosis*, Respir. Res., 2001, 164-168, 2(3).
Storla et al., A systematic review of delay in the diagnosis and treatment of tuberculosis, BMC Public Health, Jan. 14, 2008, 15, 8.
Sun et al., Comparison of gyrA gene mutations between laboratory-selected ofloxarin-resistant *Mycobacterium tuberculosis* strains and clinical isolates, Int. J. Antimicrob. Agents., Feb. 2008, 115-112, 31(2).
Telenti, Genetics and pulmonary medicine. 5. Genetics of drug resistant tuberculosis, Thorax, Sep, 2008, 793-797, 53.
Thierry et al., Characterization of a *Mycobacterium tuberculosis* insertion sequence, IS6110, and its application in diagnosis, J. Clin. Microbiol., Dec. 1990, 2668-2673, 28(12).
Valente et al., A kinetic study of in virto lysis of *Mycobacterium smegmatis*, Chemical Engineering Science, 2009, 1944-1952, 64.

Van Soolingen et al., Comparison of various repetitive DNA elements as genetic markers for strain differentiation and epidemiology of *Mycobacterium tuberculosis*, J. Clin. Microbiol., Aug. 1993, 1987-1995, 31.
Viljoen et al., A macroscopic kinetic model for DNA polymerase elongation and the high-fidelity nucleotide selection, Computational Biology and Chemistry, Apr. 2005, 101-110, 29.
Wang et al., Fluoroquinolone resistance in *Mycobacterium tuberculosis* isolates: associated genetic mutations and relationship to antimicrobial exposure, J. Antimicrob. Chemother., May 2007, 860-865.
World Health Organization, Global tuberculosis control—epidemiology, strategy, financing, WHO Report 2009, WHO/HTM/TB/2009.411.
Copending U.S. Appl. No. 29/400,931.
Copending U.S. Appl. No. 13/452,419.
Analytical Biochemistry 186, 328-331 (1990) "Minimizing the Time Required for DNA Amplication by Efficient Heat Transfer to Small Samples".
PCT Written Opinion & Search Report for Application No. PCT/US2012/040201 dated Aug. 1, 2012.
Northrup, M. Allen, et al., "A miniature integrated nucleic acid analysis system", Automation Technologies for Genome Characterization, 1997, pp. 189-204.
Wittwer, Carl T. et al, "Minimizing the time required for DNA amplification by efficient heat transfer to small samples", Anal. Chem. 1998, 70, 2997-3002.
Friedman, Neal A., et al., "Capillary tube resistive thermal cycling", The 7th International Conference on Solid-State Sensors and Actuators, 924-926.
International Search Report & Written Opinion dated Aug. 16, 2012; Application No. PCT/US2012/034506.
International Preliminary Report on Patentability dated Oct. 16, 2013; PCT/US2012/040201.
European Office Action dated Nov. 6, 2012; Application No. 09713496.9-2113.
Extended European Search Report dated Aug. 19, 2011; Application No. 09713496.9.
European Communication dated Jun. 9, 2011; Application No. 09713496.9.

* cited by examiner

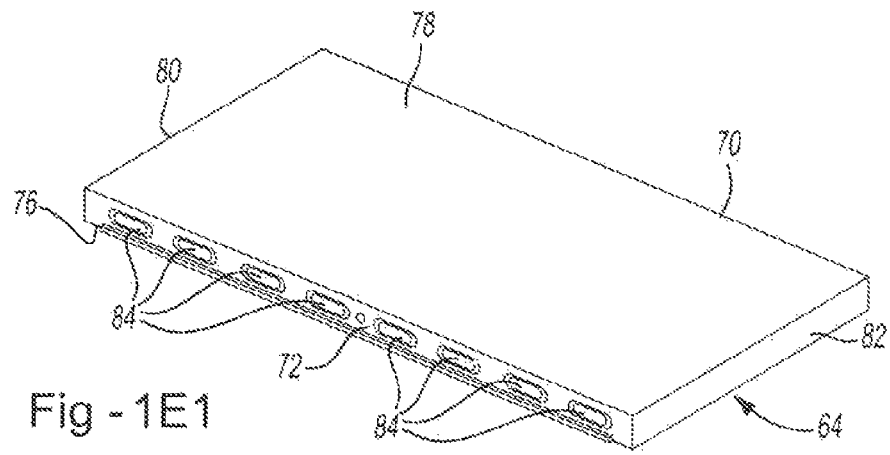
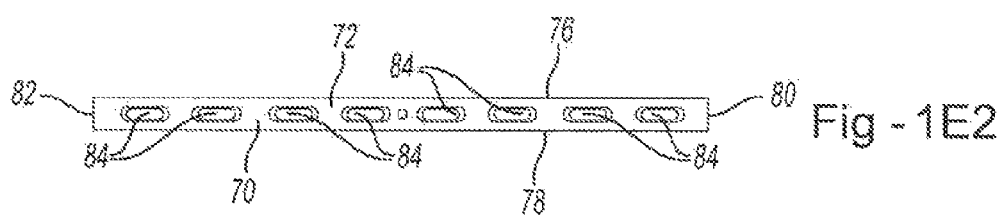
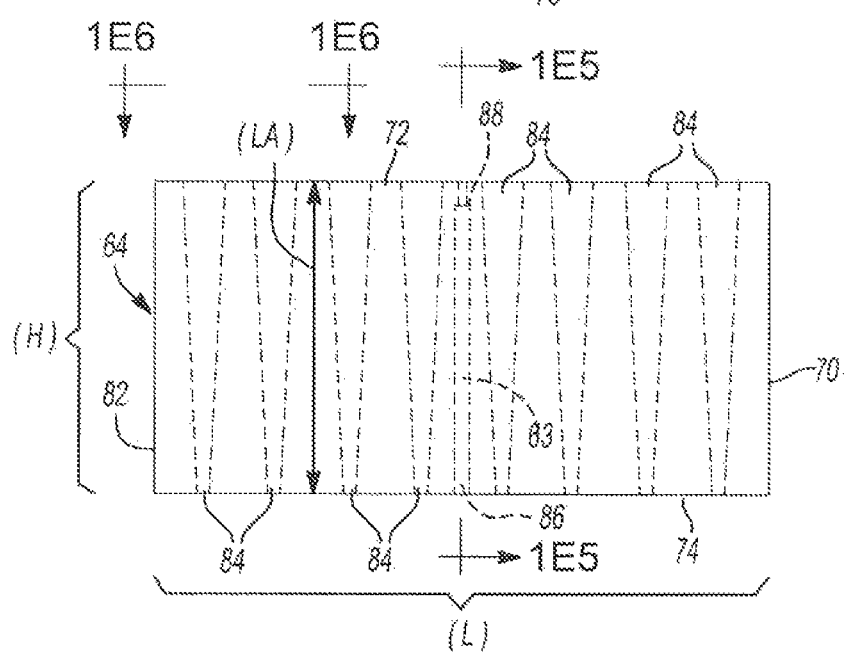
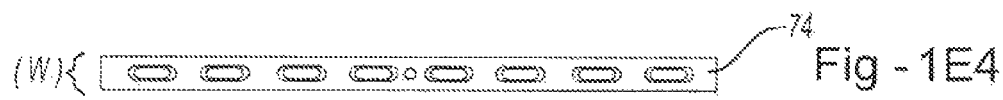

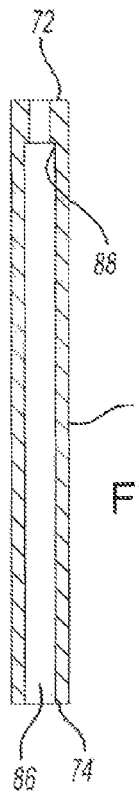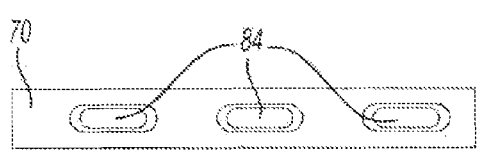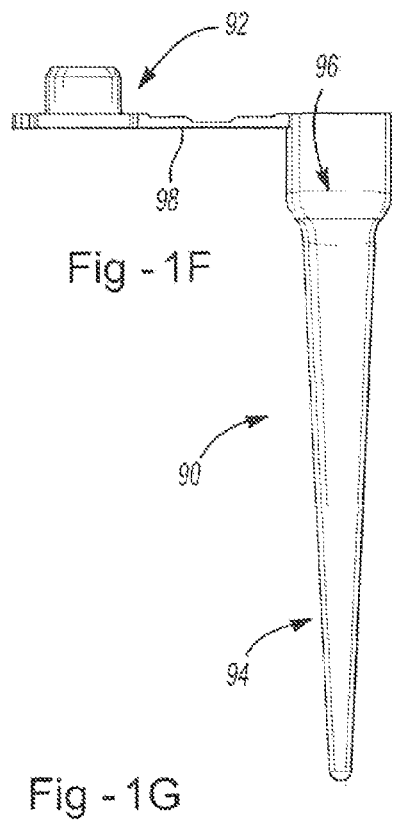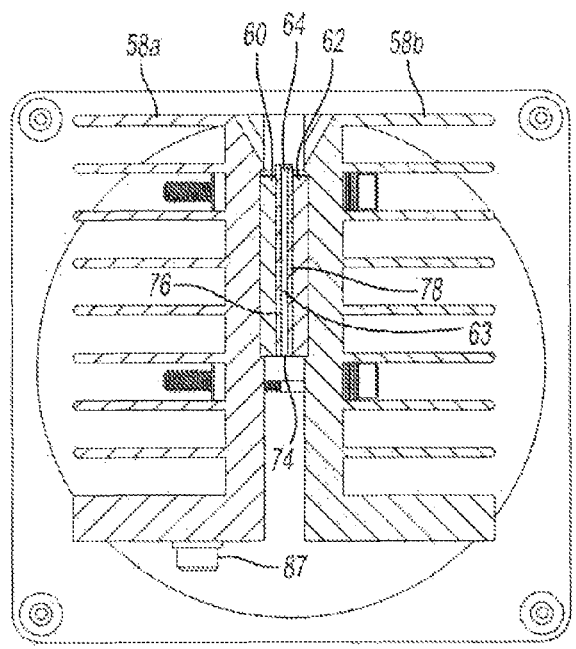

RAPID THERMOCYCLER SYSTEM FOR RAPID AMPLIFICATION OF NUCLEIC ACIDS AND RELATED METHODS

CLAIM OF PRIORITY

The present application claims the benefit of the filing date of U.S. Provisional Application No. 61/492,002, filed Jun. 1, 2011, the contents of which are hereby incorporated by reference for all purposes.

FIELD OF THE INVENTION

The present invention relates generally to executing time and/or temperature based protocols for treatment of biological samples (such as amplification of nucleic acids) and more particularly to a thermocycler instrument exhibiting rapid polymerase chain reaction (PCR) characteristics.

BACKGROUND OF THE INVENTION

The polymerase chain reaction (PCR) is a process that is employed for amplifying nucleic acid molecules. In a typical process, a sample is subjected to a number of thermal cycles, each of which includes a heating stage and a codling stage. By selecting appropriate temperatures during the stages, a sample can be subjected to denaturation, annealing, and elongation conditions until the number of copies of the desired nucleic acid segment (e.g., gene) has increased exponentially. Nowadays, PCR is often employed by way of a device known as a thermocycler.

In WO/2009/105499, there is described an improved thermocycler for PCR. The apparatus described therein addresses performance problems associated with typical art-disclosed thermocyclers. As one means to improving performance, that publication describes generally a system by which at least two thermoelectric modules (each including a thermoelectric device (TED) and an associated heat exchanger) are placed in spatial opposition in which any number of sample vessels are placed in the interior region between the thermoelectric modules.

Notwithstanding the improvements that result in performance from the apparatus of WO/2009/105499, there remains a need in the art for additional efficient thermocycler devices. There also remains a need in the art for improved approaches to the operation of such devices so that reliable and consistent amplification is achieved efficiently, and with relatively low risk of damage to samples, equipment or both, during operation.

Moreover, there continues to be a need to address obstacles that confront many thermocycler devices occasioned by thermal inertia characteristics, namely the heat transfer performance of a mass that is influenced by combination of its thermal conductivity, size, heat capacity, and the dead time inherent to the control operation. There also remains a need for a system that accounts for potential lags in thermal processing due to the execution of one or more electronic control operations and the behavior of the hardware components employed therein.

SUMMARY OF THE INVENTION

The present teachings meet one or more of the above needs, by providing a thermocycling instrument including at least one of each of a first and second spaced apart temperature sensor and being adapted for rapid PCR by at least one controller that dynamically adjusts one or more control parameters (e.g., the duration, nature and/or amount of an electricity supply, such as the amount of power, the amount of time of delivery, polarity, and/or any pulse width modulation) for controlling at least one thermal cycling element (e.g., one or more thermoelectric devices) on the basis of temperature condition information obtained from the temperature sensors (such as by way of a closed-loop control operation). In one aspect, a thermocycler instrument for polymerase chain reaction amplification of a sample comprises at least one first thermal cycling element and at least one second thermal cycling element, the first and the second thermal cycling elements being in generally opposing relation with one another. The instrument may also include a sample holder adapted to receive at least one sample and being disposed between the first thermal cycling element and second thermal cycling element in thermal communication (e.g., conducting) relation with each of the first thermal cycling element and second thermal cycling element. The instrument further includes at (east one heat exchanger for transferring heat from or to each of the first and second thermal cycling element and/or the sample holder. The instrument may also include at least one first temperature sensor that monitors a first temperature condition of (and preferably within) the sample holder and is adapted to provide information (e.g., via at least one first electrical signal) corresponding with the first temperature condition. The first temperature condition preferably corresponds with the temperature condition of a sample being processed within the sample holder. At least one second temperature sensor may also be included such that the at least one second temperature sensor monitors a second temperature condition (e.g., of a heat exchanger component, which may be in thermal conducting relation with the sample holder) external of the sample holder, and is adapted to provide information (e.g., via a second electrical signal) corresponding with the second temperature condition. Other locations than the heat exchanger may include another element, which may be a temperature sensor, that is in thermal conducting relation with the sample holder. The instrument optionally includes at least one air mover for exhausting air from the thermocycler instrument, or otherwise convecting air within the thermocycler instrument.

The instrument may also include at least one associated control device (which may be part of a closed loop control system) that is: (i) adapted to interface with a power supply to adjust the delivery of power to any first thermal cycling element and/or second thermal cycling element, and/or any optional air mover; (ii) adapted to be in signaling communication (directly or indirectly) with the first temperature sensor and the second temperature sensor for receiving the information about temperature conditions (e.g., via the first and second electrical signals); (iii) configured for analyzing the temperature information (e.g., the first and second electrical signals) from the first temperature sensor and the second temperature sensor; and (iv) configured such that, based upon such analyzing of such temperature information (e.g., from the sensor signals), the at least one control device alters an operational parameter (e.g., the duration, nature and/or amount of an electricity supply, such as the amount of power, the amount of time of delivery, polarity, any pulse width modulation) that is delivered to one or more of the first thermal cycling element and second thermal cycling element, or any optional air mover. The control device may alter any such operational parameter on the basis of such temperature information and may employ one or more algorithms that may dynamically calculate values that affect such operational parameters.

Any of a number of variations may be possible, within the teachings herein. Without, limitation, a housing is also included as a part of the instrument, the housing being configured for at least partially enclosing at least the first and second thermal cycling elements, the at least one heat exchanger, the at least one first temperature sensor, the at least one second temperature sensor, at least a portion of the electrical circuitry (it being recognized as well that some or all of the devices that function to control the instrument may be located on-board the instrument, or separate from the instrument (e.g., as part of a separate computing device)). The housing may optionally include at least one exhaust port for exhausting air transported by any optional air mover, optionally at least one air inlet structure for letting in air transported by any optional air mover, and at least one sample access opening. The housing may be similar to that disclosed in U.S. Design patent application No. 29/400,931 which is incorporated by reference herein for all purposes.

The sample holder may be a substantially solid metal block (e.g., free of liquid coolant flow passages) that includes a plurality of bores defined therein, each having a longitudinal axis and being adapted to receive a sample and at least one sensor, bore having a longitudinal axis defined in the block (e.g., in a position that sees a substantially similar temperature condition as samples contained in the holder) and being adapted to receive the at least one first temperature sensor. The sample holder may be configured as a solid block free of any passage other than the bores and optionally may be made of sterling silver, preferably as dead soft sterling silver, half hard sterling silver, full hard sterling silver or a combination thereof. The longitudinal axis of each bore and of the sensor bore may be generally parallel with each other and with a pair of opposing outer surfaces of the sample holder that are in thermal conducting relation with thermal cycling elements (e.g., thermoelectric elements), at least one of which having a heat exchanger associated with it. The sample holder may include a plurality of bores that have an oval transverse cross-sectional geometry, a tapered longitudinal cross sectional geometry. The sample holder may be configured (e.g., with tapered bores that narrow as they progress deeper into the holder) to apply pressure to a sample tube inserted therein for causing the sample tube to deform, such as for improving the rate of heat transfer to and from a contained sample as compared with a holder that does not apply such pressure. The sample, holder may be configured as a generally rectangular prism block that has a width that is less than about 10% of the height of the block. For example, the width may be less than about 3 mm (e.g., about 2.7 mm). The second temperature sensor may be a thermistor.

The at least one control device may include a computer program product comprising at least one non-transitory tangible machine, readable medium on which is provided program instructions for operating the instrument for causing a sample contained by the sample holder to undergo polymerase chain reaction amplification by repeated cycling between at least one heating step (which may be for denaturation, elongation, or both) and at least one cooling step (which, may be for annealing). The program instructions may comprise code that receives data about the first temperature condition corresponding with a temperature of the sample holder (e.g., a temperature within the holder that substantially approximates the temperature of samples in the holder) and a second temperature condition corresponding with a temperature external of the sample holder. Based upon the data of the first temperature and the second temperature, the program may cause one or more calculations to be performed and/or cause a dynamic altering of power that is delivered for controlling operation of, at least one thermal cycling element of the instrument (and/or any optional air mover). Based upon the data of the first temperature and the second temperature, the program may include adjustments (which may occur within a single stage, within a series, of stages or both) to the control parameters employed within the control algorithm.

Any air mover employed may be an axial fan, having an axis of rotation of an impeller. The air mover may be positioned adjacent an exhaust port located on a side wall of the housing. Each of the heat exchangers may have a plurality of fins that project generally laterally away from a plane that is aligned generally parallel with the axis of rotation of the impeller. The fins may be further oriented, for allowing a flow, (which may be a laminar flow and/or may have a turbulent component) of air over them occasioned by the rotation of an impeller of one or more air mover.

The thermocycler instrument may be operable at a rate sufficient to amplify a volume of at least 50 microliters (µl) of a sample to the extent of at least 30 cycles each over a span of at least about 30° C. in a period of less than about 15 minutes, less than 10 minutes, or even less than 5 minutes.

The present teachings may further provide for a method for operating a thermocycler instrument, comprising the steps of: (a) supplying power to a thermocycler instrument that includes at least two generally opposing and spaced apart thermal cycling elements (e.g., thermoelectric devices), a sample holder, therebetween, and heat exchangers associated with the thermoelectric devices and projecting away from the sample holder; (b) applying a voltage signal having a positive polarity and a negative polarity to the at least two generally opposing and spaced apart thermal cycling elements (e.g., thermoelectric devices) of the thermocycler via at least one circuit; (c) optionally, applying; a voltage signal to an air mover circuit for rotating an impeller of an air mover for convectively expelling air from the thermocycler; (d) controlling the polarity of the voltage signal that is applied to the thermal cycling elements (e.g., thermoelectric devices) to repeatedly alternate the operation of the thermoelectric device between a first condition of supplying heat to the sample holder (e.g., as part of a heating stage) and a second condition removing heat from the sample holder (e.g., as part of a cooling stage); (e) obtaining a first sample holder electrical signal corresponding with a temperature condition approximate that of a sample, such as a temperature condition of the sample holder (e.g., a temperature within the sample holder); (f) obtaining a second electrical signal corresponding with a temperature from external of the sample holder; and (g) employing the temperature sensor information (e.g., as derived from the first sample holder electrical signal and the second electrical signal) for determining values for controlling power delivery (e.g., the duration, nature and/or amount of an electrical power supply, such as the amount of power, the amount of time of delivery, polarity, any pulse width modulation) to be delivered to the thermal cycling elements (e.g., thermoelectric devices). These steps are repeated for a predetermined number of cycles per a user inputted protocol.

The methods herein may include steps of applying power to a thermal cycling element (e.g., a TED) for heating to a first setpoint temperature and altering the power application at a temperature below the first setpoint temperature and allowing the sample holder to come to temperature. The method for operating a thermocycler instrument may include performing a series of repeated cycles or loops that each include at least one heating stage (which may include heating to one, two, or more different temperatures with optimal holds at such temperatures), and at least one codling stage (which likewise may include cooling to one, two, or more different temperatures with optimal holds at such temperatures). The method may include stages in which both heating and codling are performed. For example, for the teachings herein, generally, heating or cooling preferably at relatively high levels, such as at or near 100% available power (e.g., to a power of at least about 200 watts (w) or even 250 watts (w), can occur until an offset temperature is reached and then the operation is switched to a cooling or heating, respectively, until a setpoint temperature (desirably a user inputted setpoint temperature) is reached. Such switched operation may be at or near 100% available power as well, but may be for a relatively short duration. The method for operating a thermocycler instrument may include a heating stage that includes causing heating until a sensed temperature (e.g., via a signal corresponding with a temperature) within the sample holder indicates that the temperature of the sample holder has reached a first offset temperature that is within a dynamically calculated amount below a setpoint temperature, and then causing cooling, of the sample holder for a sufficient amount of time so that the temperature, arrives at the setpoint with a substantial avoidance of any overshoot (e.g., overshoot of less than about 1° C., or even less than about 0.25° C.). The method for operating a thermocycler instrument may include, a cooling stage that includes causing cooling until a sensed temperature (e.g., via a signal corresponding with a temperature) within the sample holder indicates that the temperature of the sample holder has reached a second offset temperature that is within a predetermined amount above a setpoint temperature, and then causing heating of the sample holder for a sufficient amount of time so that the temperature arrives at the setpoint with a substantial avoidance of any undershoot (e.g., undershoot of less than about 1° C. or even 0.25° C.). The method for operating a thermocycler instrument may be such that a step is employed of obtaining temperature information (e.g., via sensor signals corresponding with a temperature) from external of the sample holder which includes obtaining a temperature value from at least one of the heat exchangers, which temperature value is employed for determining the first and second offset temperature.

The thermocycler instruments herein may be adapted to operate and may be operated for heating the sample holder at a rate of at least about 8° C./second. The thermocycler may be adapted to operate and may be operated for cooling at a rate of at least about 6° C./second. The thermocycler may be capable of a total runtime of less than or equal to 30 minutes, 15 minutes or faster, for completed amplification. One or more bores for accepting a sample tube within the thermocycler experience thermal uniformity within ±2° C. of one another, and more preferably within ±1° C. of one another, or within ±0.5° C. of one another. To achieve such uniformity, the first and second thermal cycling elements (e.g., TEDs) may both apply heat to the bores simultaneously or may both provide cooling to the bores simultaneously.

The methods herein for operating a thermocycler instrument may include operating the thermocycler instrument by heating and cooling within a temperature range of about 95° C. to about 60° C. for at least 30 cycles in under about, 15, 10 or even 5 minutes with sample volumes of about 50 µl with a thermal control of ±1° C. from setpoint temperatures.

In one very particular aspect of the teachings it is envisioned that a method for operating a thermocycler instrument may include a step of employing the first sample holder electrical signal and the second electrical signal for determining values for controlling power delivery to be delivered to the thermoelectric devices. The determining of values includes steps of: (i) receiving at least one first setpoint temperature predetermined by a user, the at least one first setpoint temperature being a maximum temperature to which a sample is to be heated for polymerase chain reaction (e.g., for denaturation and/or elongation) of at least one sample; (ii) receiving at least one second setpoint temperature predetermined by the user, the at least one second setpoint temperature being a minimum temperature to which the at least one sample is to be cooled (e.g., for annealing of the at least one sample); (iii) receiving at least one first hold time corresponding with an amount of time predetermined by the user during which the temperature of the sample holder is maintained generally at the at least one first setpoint temperature; (iv) receiving at least one second hold time corresponding with an amount of time predetermined by the user during which the temperature of the sample holder is maintained generally at the at least one second setpoint temperature; (v) causing each of the thermal cycling elements (e.g., thermoelectric devices) to heat a sample holder; (vi) receiving first heating temperature information (e.g., at least one first sensor signal) from a first temperature sensor corresponding with a temperature of the sample holder (which desirably approximates the temperature condition of the sample being processed; (vii) receiving second heating temperature information (e.g., at least one second sensor signal) from at least one second temperature sensor that is located externally of the sample holder; (viii) determining a value of any first temperature offset amount (TOFFSET1) based upon the temperature information from the at least one first and second temperature, sensors; (ix) causing heating of the sample holder until the sample holder reaches a first-offset temperature that is below the first setpoint temperature by the first temperature offset amount; (x) at the time the first offset temperature is reached, causing a cooling pulsation of the at least of the of the thermal cycling elements (e.g., thermoelectric devices) during the heating stage for a sufficient amount of time so that the temperature arrives within about 1° C. (or even about 0.25° C.) of the first setpoint temperature and further heating of the sample holder is interrupted; (xi) causing the temperature to be maintained within about 1° C. (or even about 0.25° C.) of the first setpoint temperature for the first hold time (e.g., by causing pulse, width modulation of the power to the thermal cycling elements); (xii) causing at least one thermal cycling, element, (e.g., TED) to cool a sample holder; (xiii) receiving first cooling temperature information (e.g., a signal from the first temperature sensor) corresponding with a temperature of the sample holder; (xiv) receiving second cooling temperature information (e.g.; a signal) from the at least one second temperature sensor that is located remotely from the sample holder; (xv) determining a value of any second temperature offset amount (TOFFSET2) based upon the temperature information from the at least one first and second temperature sensors; (xvi) causing cooling of the sample holder until the sample holder reaches the second offset temperature that is above the second setpoint temperature by the second temperature offset amount; (xvii) at the time when the second offset temperature is reached, causing a heating pulsation of at least one of the thermal cycling elements (e.g., thermoelectric devices) during the cooling stage for a sufficient amount of time so that the temperature arrives within about 1° C. (or even about 0.25° C.) of the second setpoint temperature and further cooling of the sample holder is interrupted; (xviii) causing the temperature to be maintained within about 1° C. (or even about 0.25° C.) of the second setpoint temperature for the second hold time; and (xix) repeating the above steps as necessary for a predetermined number of cycles until the amplification desired by the user is achieved.

Methods herein for operating a thermocycler instrument may include, a heating stage that includes causing heating until temperature information (such as that derived from at least one signal corresponding with a temperature within the sample holder) indicates that the temperature of the sample holder (or the sample therein) has reached a first offset temperature that is within a predetermined amount below a setpoint temperature, and then causing cooling of the sample holder for a sufficient amount of time so that the temperature arrives at the setpoint with overshoot of less than about 1° C. (or even less than about 0.25° C.). The method for operating a thermocycler instrument may include a cooling stage that includes causing cooling until temperature information, (such as that derived from at least one signal corresponding with a temperature within the sample holder) indicates that the temperature of the sample holder (or the sample therein) has reached a second offset temperature that is within a predetermined amount above a setpoint temperature, and then causing heating of the sample holder for a sufficient amount of time so that the temperature arrives at the setpoint with undershoot of less than about 1° C. (or even less than about 0.25° C.). The heating stage and/or the cooling stage may include heating or cooling to two or more temperatures and holding for a predetermined amount of time at each temperature (e.g., heating to a temperature for elongation and/or a temperature for denaturation).

The thermocycler instruments herein may be adapted to operate and may be operated for heating the sample-holder at a rate of at least about 8° C./second or even 10, 12, or 15° C./second. The thermocycler may be adapted to operate and may be operated for cooling at a rate of at least about 6° C./second or even 8, 10 or 12° C./second. Thus, by way of example, controlling of operation of the thermocycler instrument includes a step of receiving at least one first setpoint temperature of at least about 85° C., to which the at least one biological sample is to be heated in the sample holder for polymerase chain reaction denaturation, and at least one second setpoint temperature of below about 70° C. (e.g., about 55 to about 65° C.) to which the biological sample held in the sample holder is to be cooled for annealing of the at least one biological sample. A step of heating for elongation may be employed (e.g., heating to a setpoint temperature of from about 68° C. to about 78° C.). It is possible that a sequence of stages may be employed for denaturation followed by an annealing stage, followed then by a series of stages including a stage of heating for elongation, then a stage of heating for denaturation, and then a stage of cooling for annealing (i.e., heat, to denature, cool to anneal, then heat to elongate and then repeat).

Controlling of operation of the thermocycler instrument may include a step of maintaining a heating rate of at least about 8° C./second until a first offset temperature amount of no more than about 7.5° C. below the first setpoint temperature is reached for the sample holder. Controlling of operation of the thermocycler instrument may be such that when the first offset temperature is reached, pulse cooling the sample holder to slow the heating rate until the sample holder is within about 1° C. (or even about 0.25° C.) of the first setpoint temperature. Controlling of operation of the thermocycler instrument may include a step of maintaining a cooling rate of at least about 6° C./second until a second offset temperature above (by no more than about 7.5° C. above) the second setpoint temperature is reached for the sample, holder. Controlling of operation of the thermocycler instrument may be such that when the second offset temperature is reached, pulse heating the sample holder to slow the cooling rate until the sample holder is within about 1° C. (or even about 0.25° C.) of the second setpoint temperature. As indicated, and applicable in this illustration, controlling of operation of the thermocycler instrument may include a step of monitoring a first temperature corresponding with a temperature of or within the sample holder and a second temperature corresponding with a temperature of another component in thermal communication with, the sample holder (e.g., a heat exchanger).

As seen from above, controlling of operation of the thermocycler instrument may include a step of adjusting an amount of time, a temperature or both at which the steps of pulse cooling, pulse heating, or both commence based upon the first temperature and the second temperature. Controlling of operation of the thermocycler instrument may include a step of repeating the above steps for a predetermined number of cycles until the amplification desired by the user is achieved. It will also be appreciated that controlling of the operation of thermocycler instruments herein may include dynamic adjustments to one or more operating conditions based on the sensed temperatures and ongoing calculations based thereon, with such operating conditions relating, for example, to the duration, nature and/or amount of an electricity supply delivered, to one or more, thermal cycling elements, any air mover or each, (such as the amount of power, the amount of time of delivery, polarity, any pulse width modulation).

As seen from the above and will be demonstrated further herein, the present teachings demonstrate an improved approach to a closed loop control approach to controlling time and temperature operations performed on one or more biological samples. As will be appreciated from the teachings herein, a closed loop control system may be employed for controlling heating and cooling over a plurality of cycles on the basis of sensed temperature conditions corresponding with a temperature of one or more samples. A closed loop control system may be employed for controlling heating and cooling over a plurality of cycles and being adapted for achieving the desired setpoint temperatures while substantially avoiding undershoot and overshoot conditions. A closed loop control system may be employed for controlling heating and cooling over a plurality of cycles and being adapted to cause cessation or alteration of power to at least one thermal cycling element (e.g., at least one TED) prior to a sample setpoint temperature (e.g., as measured via a temperature within a sample block (e.g., a sample holder)) being reached during a heating or cooling stage, while still permitting the sample setpoint temperature to be reached. A closed loop control system may be employed for controlling heating and cooling over a plurality of cycles and being adapted to cause cessation or alteration of power to at least one thermal cycling element (e.g., at least one TED) prior to arriving at a sample setpoint temperature (while substantially avoiding undershoot and overshoot), pursuant to which the time and/or temperature at which the cessation or alteration occurs (or at which some other control operation occurs) is dynamically determined (e.g., repeatedly and on the basis of ongoing temperature measurements, such as from at least two spaced apart temperature sensors).

DESCRIPTION OF THE DRAWINGS

FIG. 1E1-1E6 include a series of drawings to illustrate views of an illustrative sample holder.

FIG. 1F illustrates a plan view of an illustrative sample tube.

1G is a side sectional view to illustrate a sample holder positioned between thermal cycling elements.

Figure 2A:
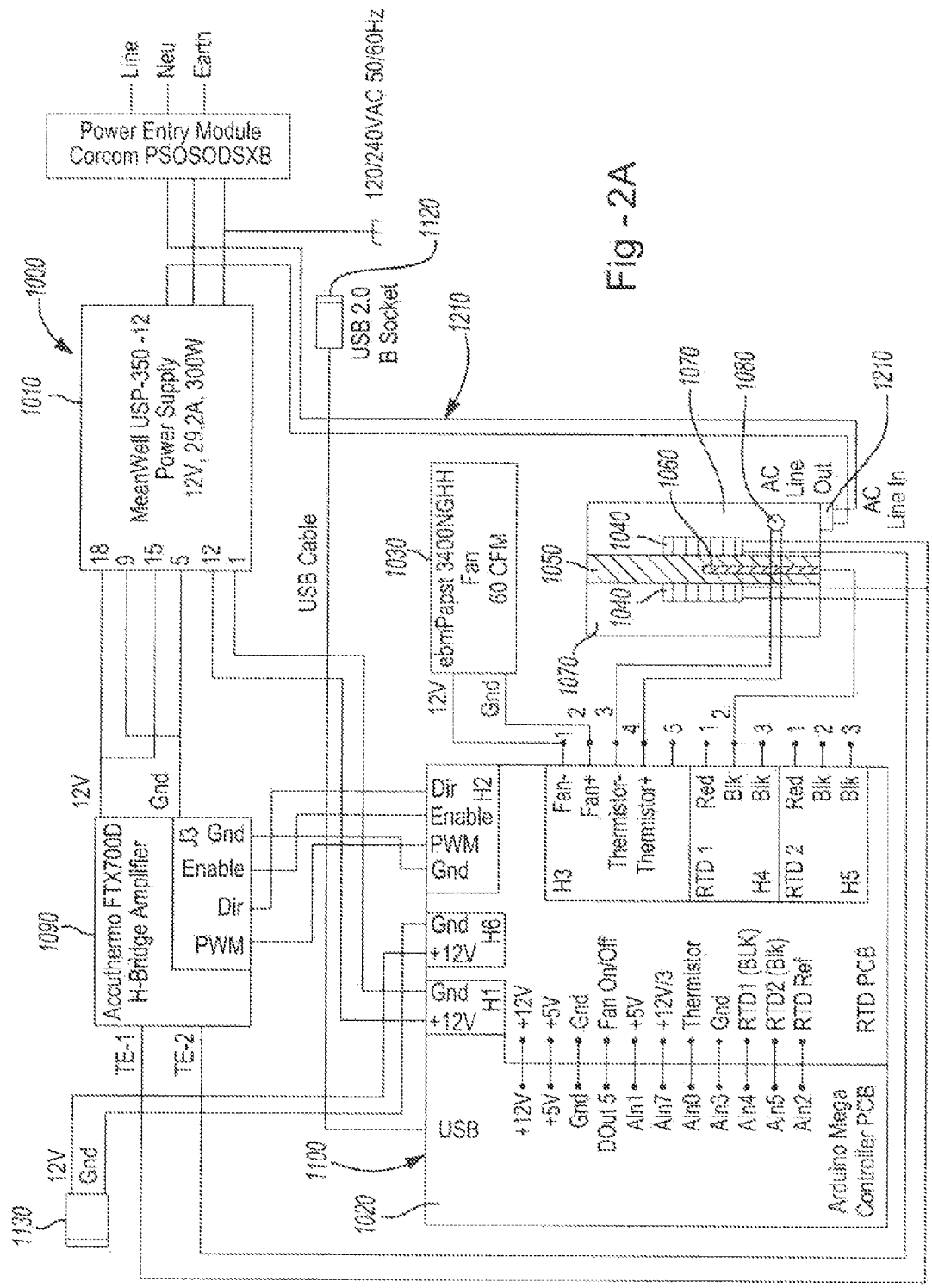

FIG. 2A is a general schematic illustrating an example of one configuration of electrically operated components of the present teachings.

Figure 2B:
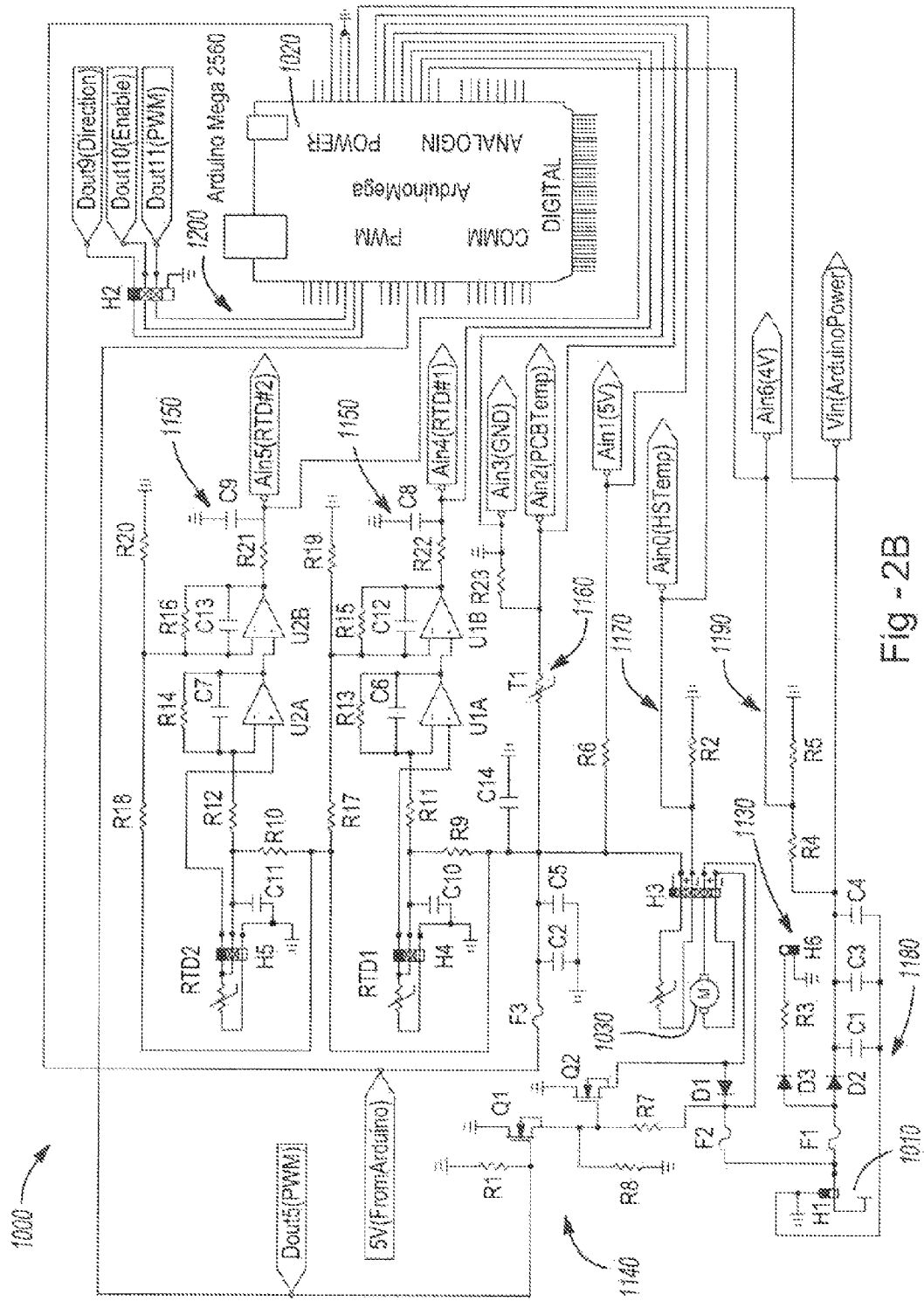
Figure 3B:
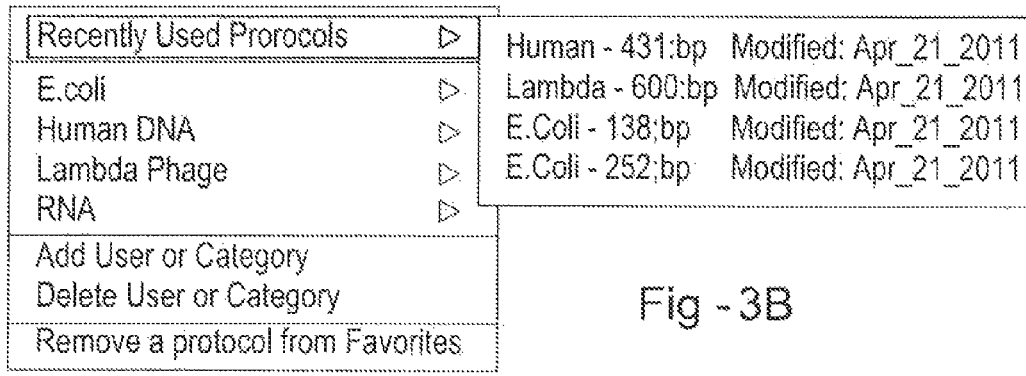
Figure 3C:
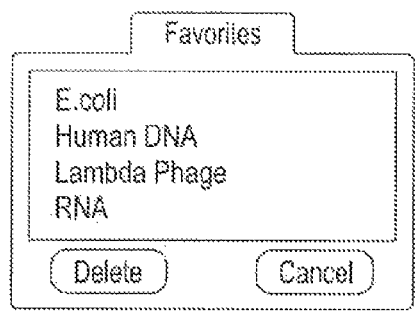
Figure 3D:
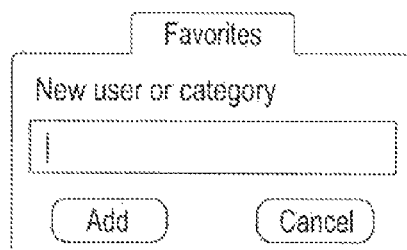
Figure 3E:
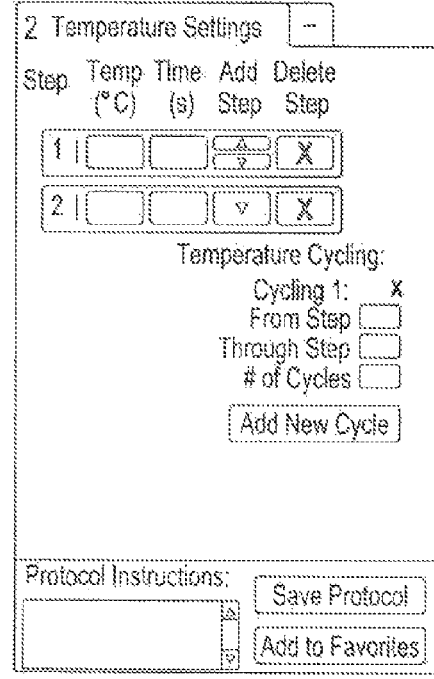
Figure 3H:
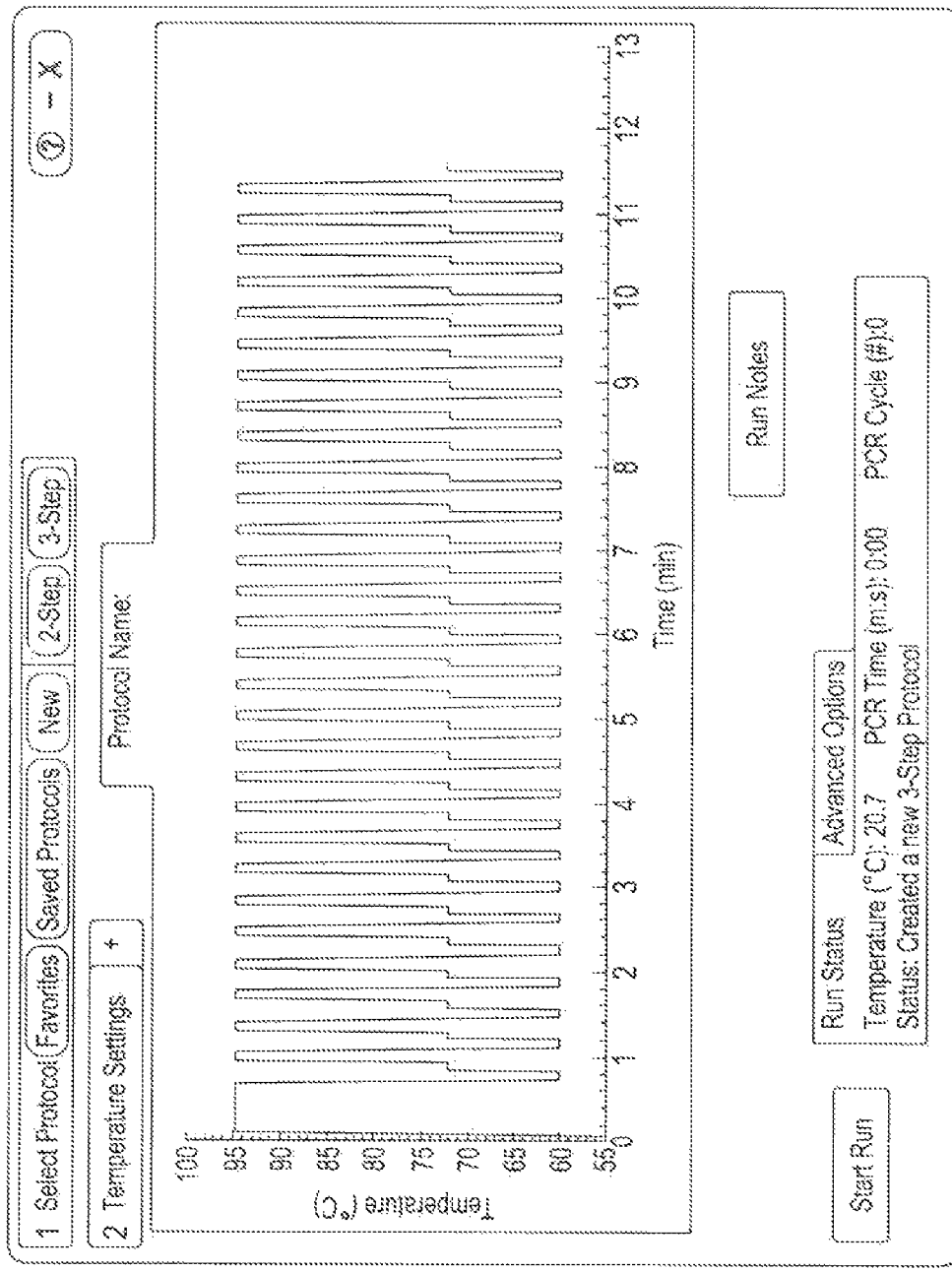
Figure 3I:
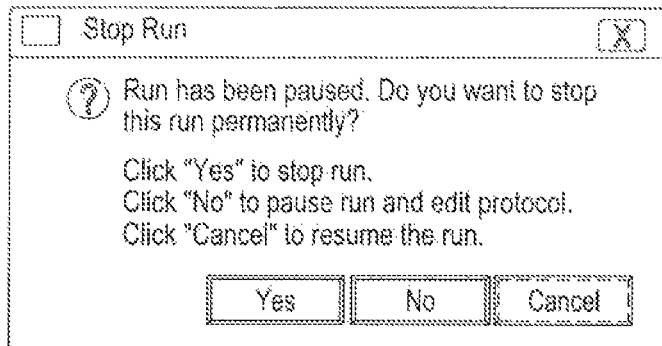
Figure 3J:
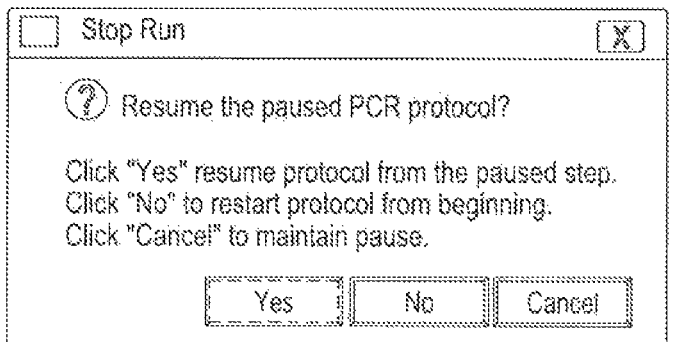

FIG. 2B is a schematic of an illustrative circuit for operating a thermocycler in accordance with the present teachings.

Figure 3A:
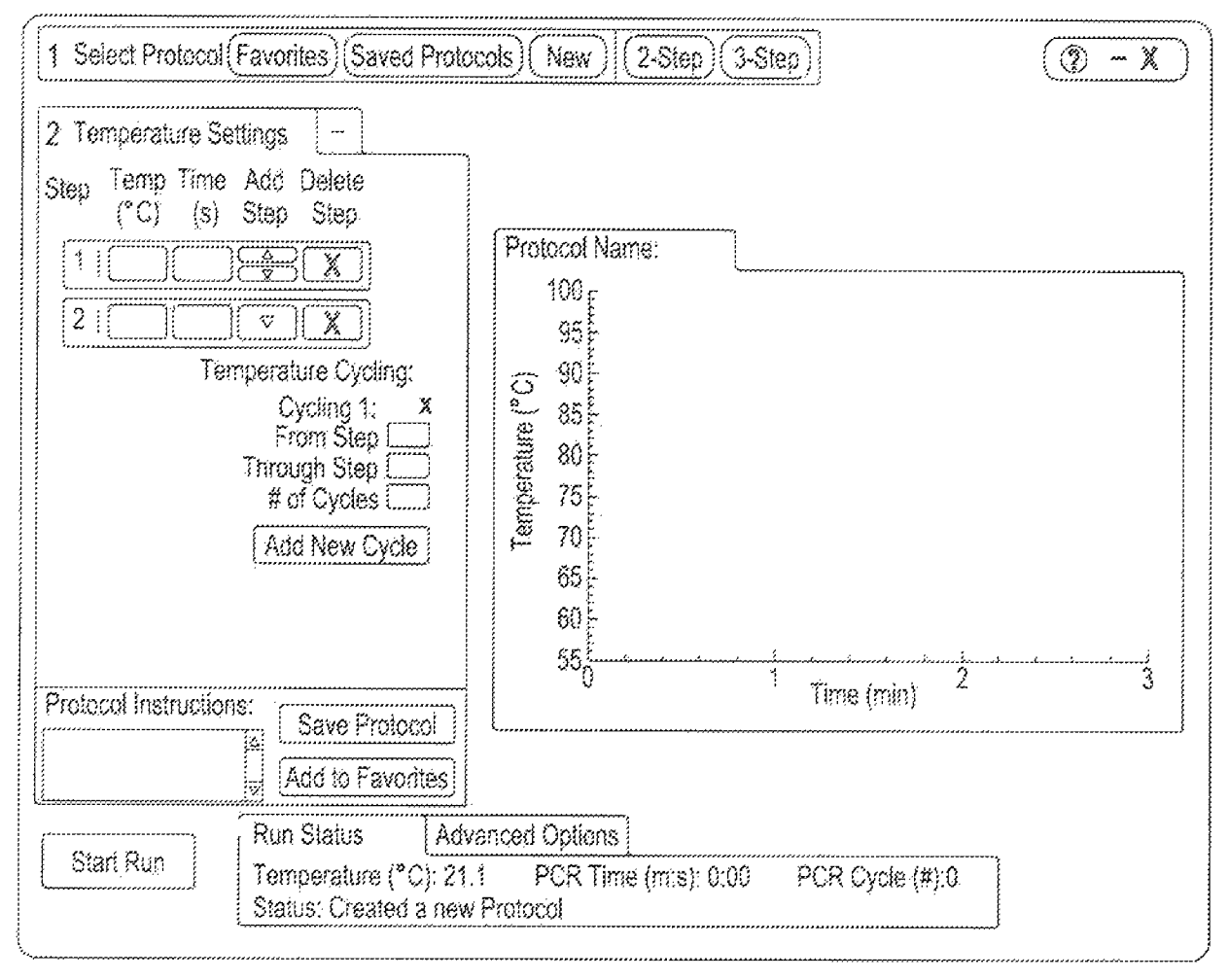
Figures 3F, 3G:
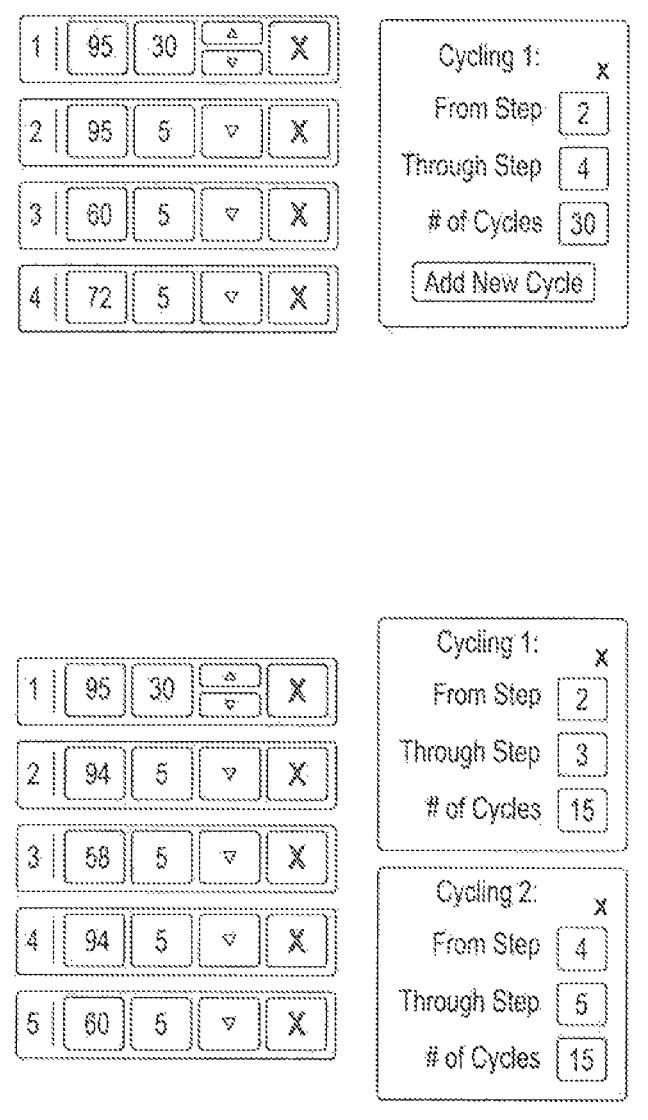

FIGS. 3A-3J are illustrative examples of user interfaces that a user may encounter during use of the thermocycler and associated software.

Figure 4A:
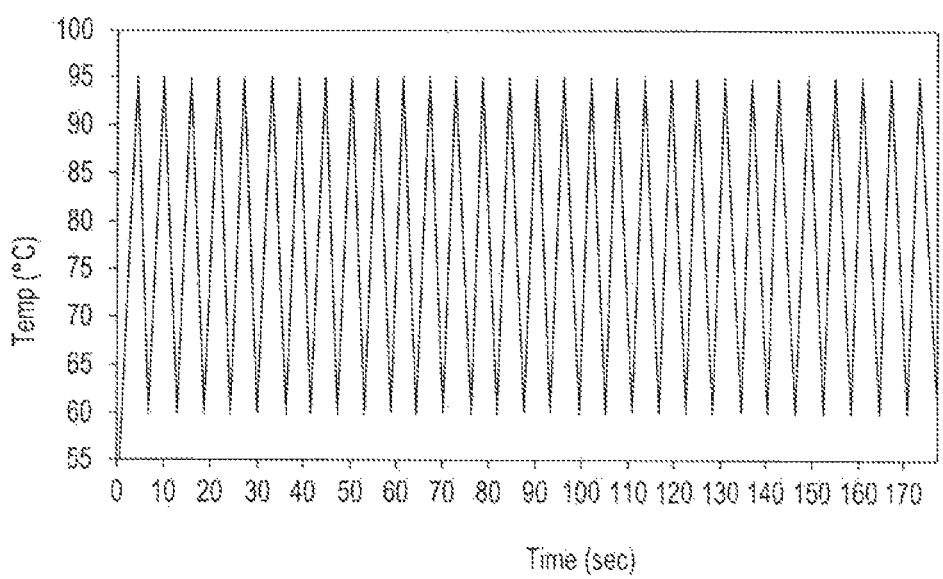
Figure 4B:
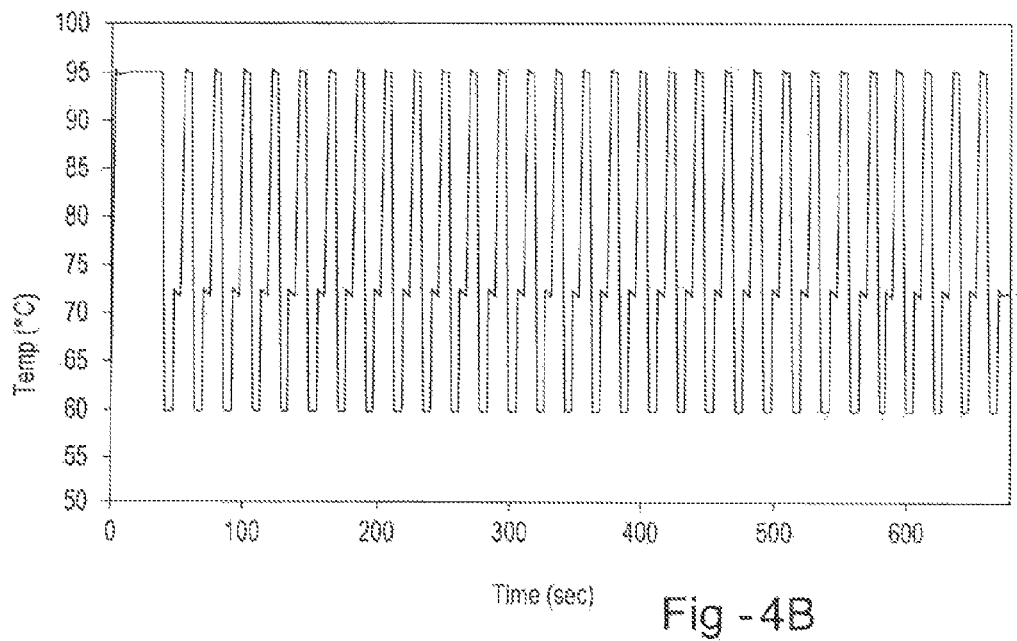
Figure 4C:
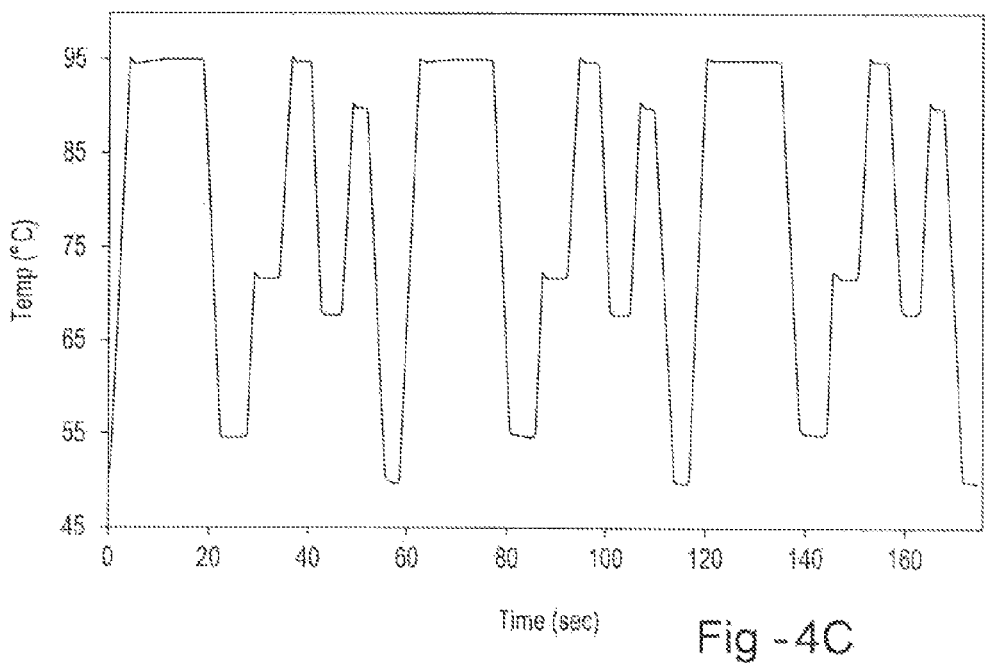

FIGS. 4A-4C are illustrative examples of temperature-time graphs of data resulting from the thermocycler.

Figure 5A:
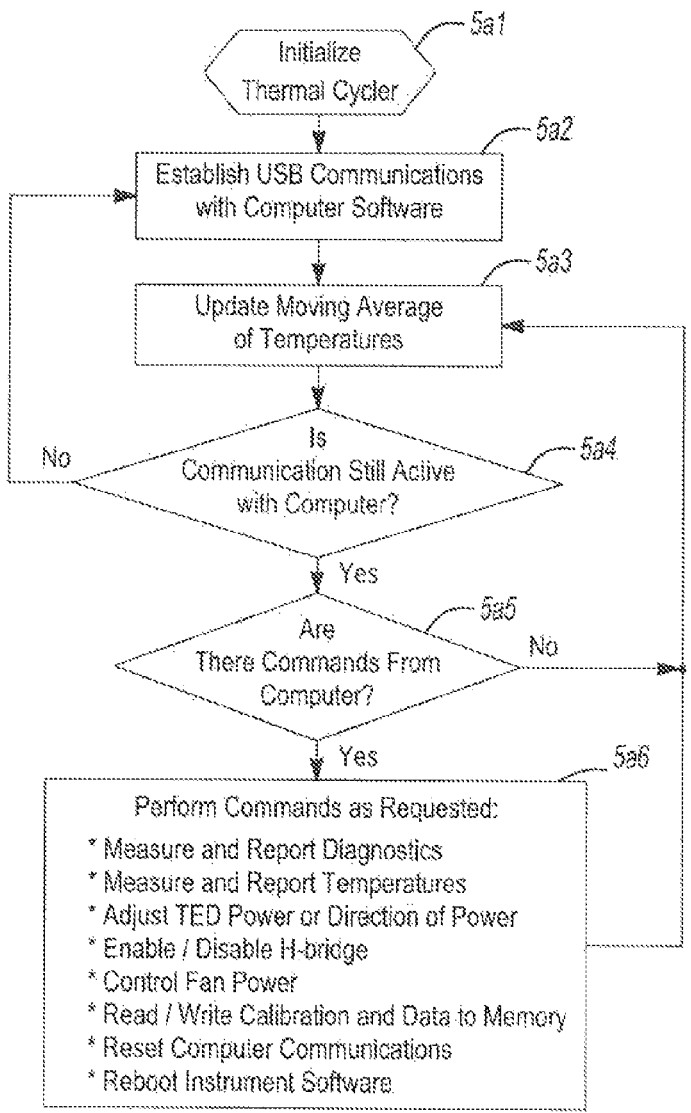

FIG. 5A is a flow chart depicting an illustrative flow of steps for software/thermocycler communication.

Figure 5B:
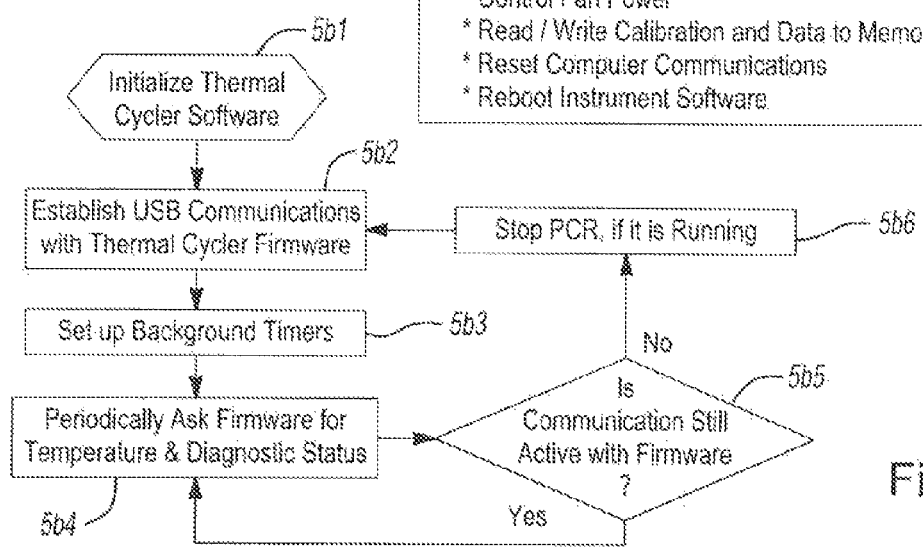

FIG. 5B is a flow chart depicting an illustrative flow of steps for software/thermocycler communication.

Figure 5C:
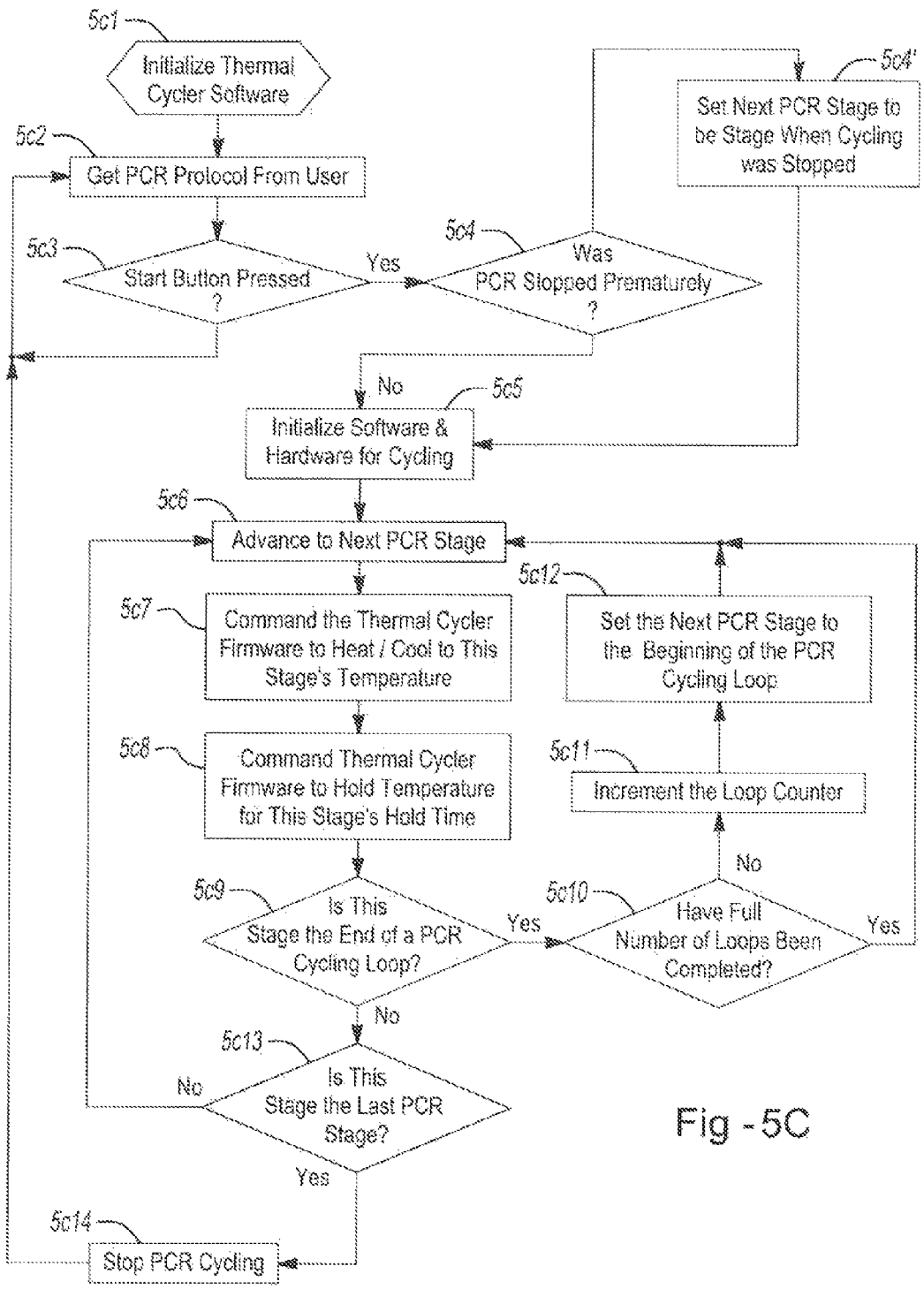

FIG. 5C is a flow chart depicting an illustrative flow of steps for software/thermocycler communication.

Figure 5D:
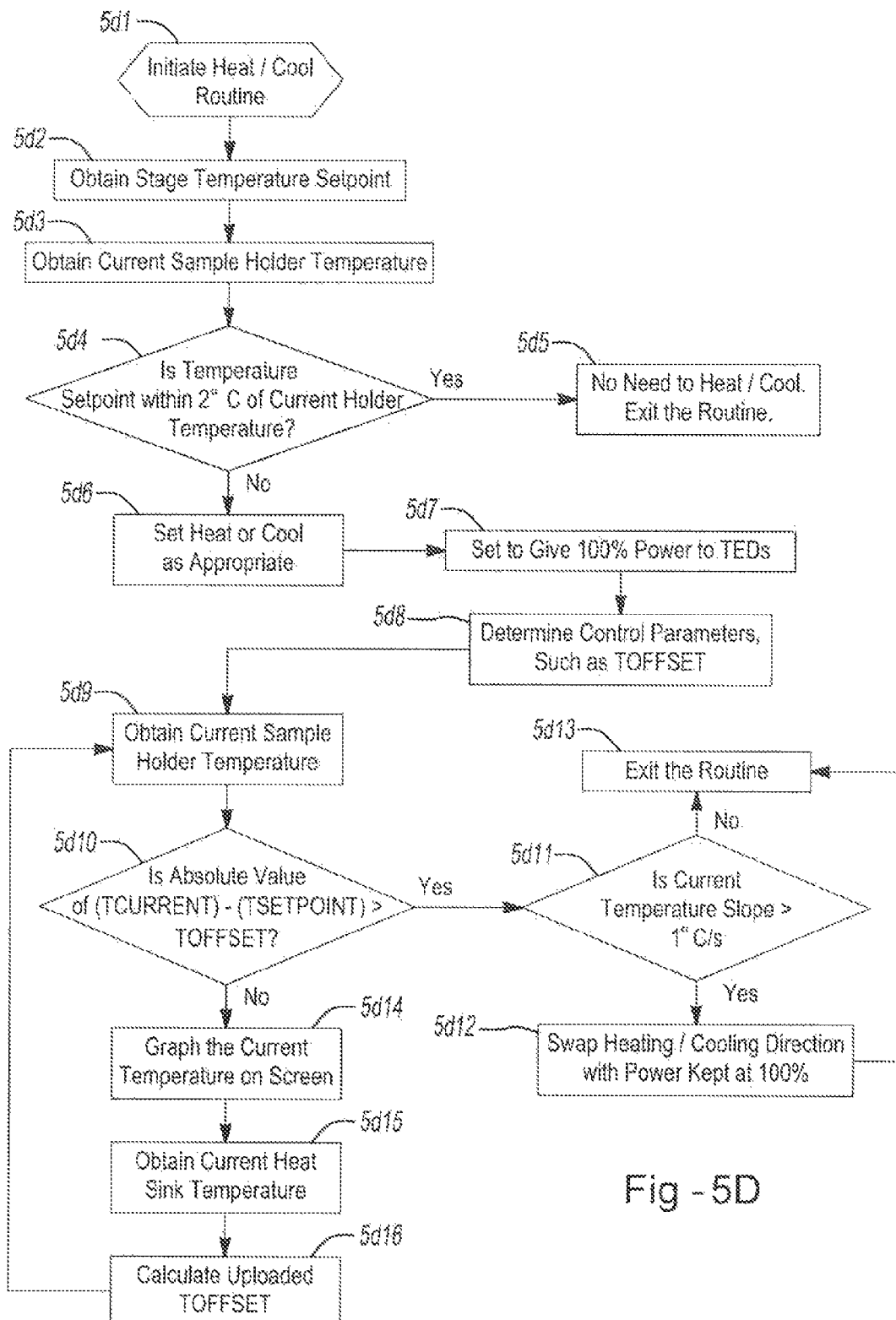

FIG. 5D is a flow chart depicting an illustrative flow of steps for temperature, control methodology.

Figure 5E:
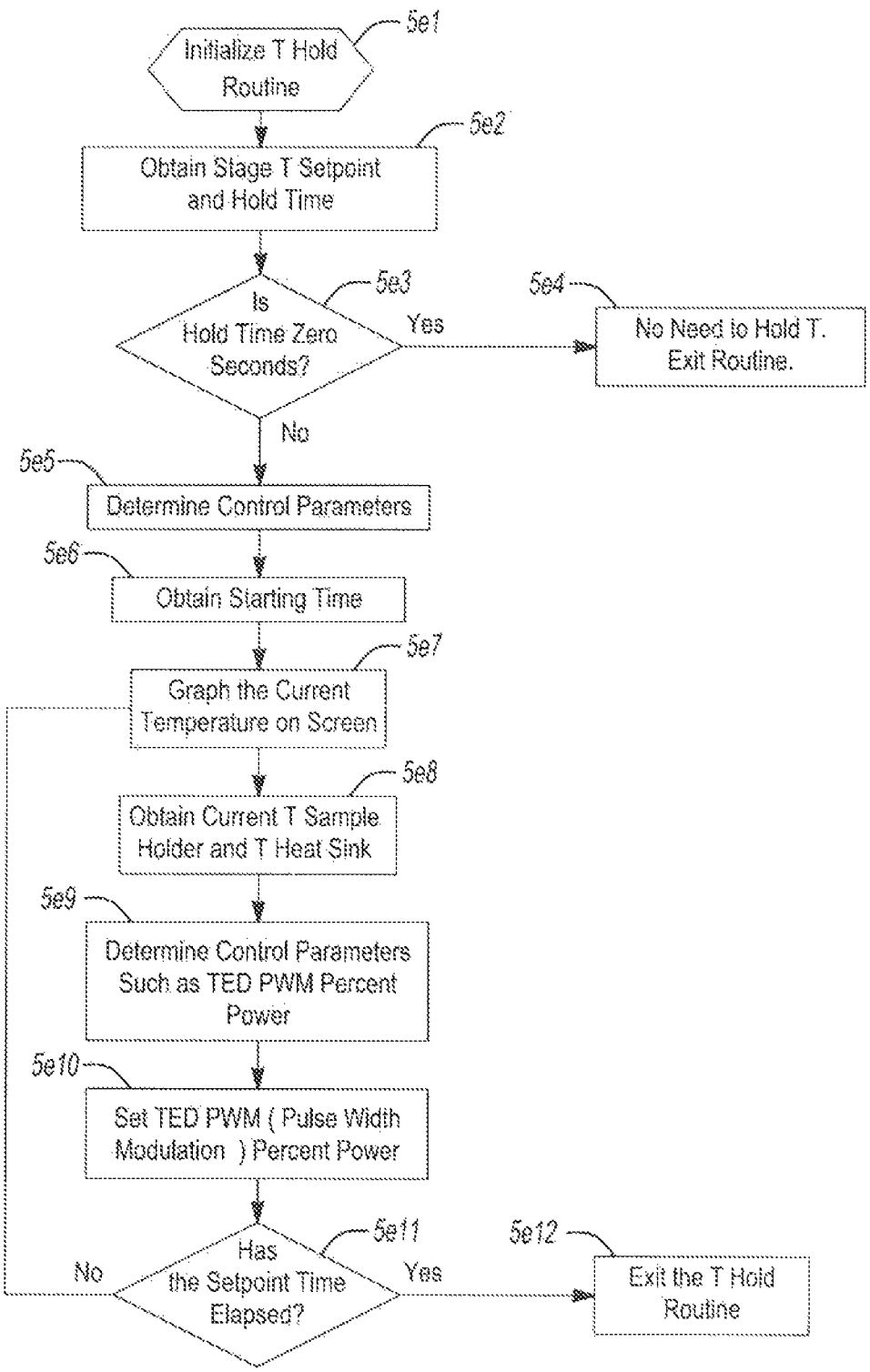

FIG. 5E is a flow chart depicting an illustrative flow of steps for hold time controls.

Figure 5F:
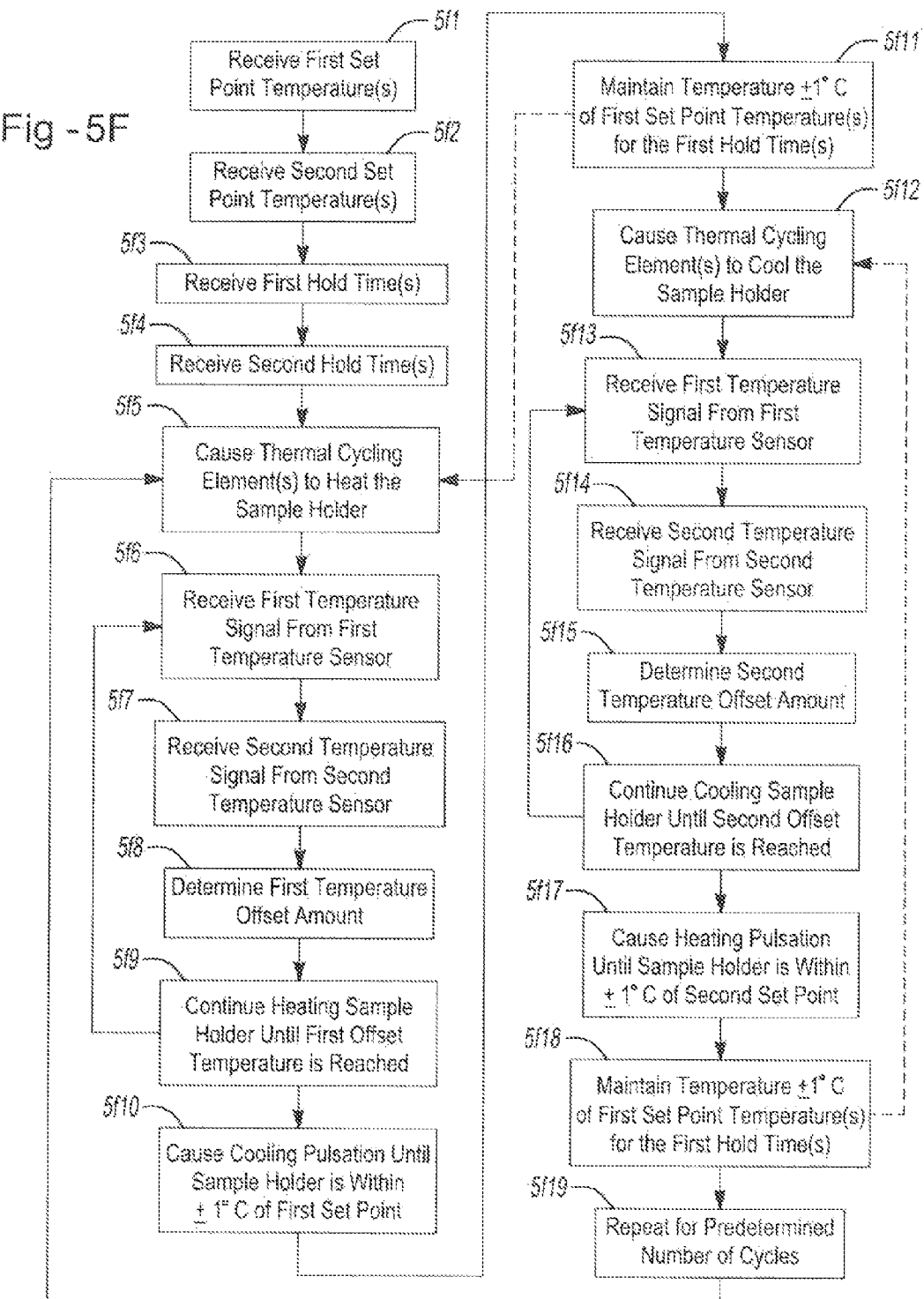

FIG. 5F is a flow chart illustrating a flow of steps for an example of a methodology for operating an instrument herein.

Figure 6:
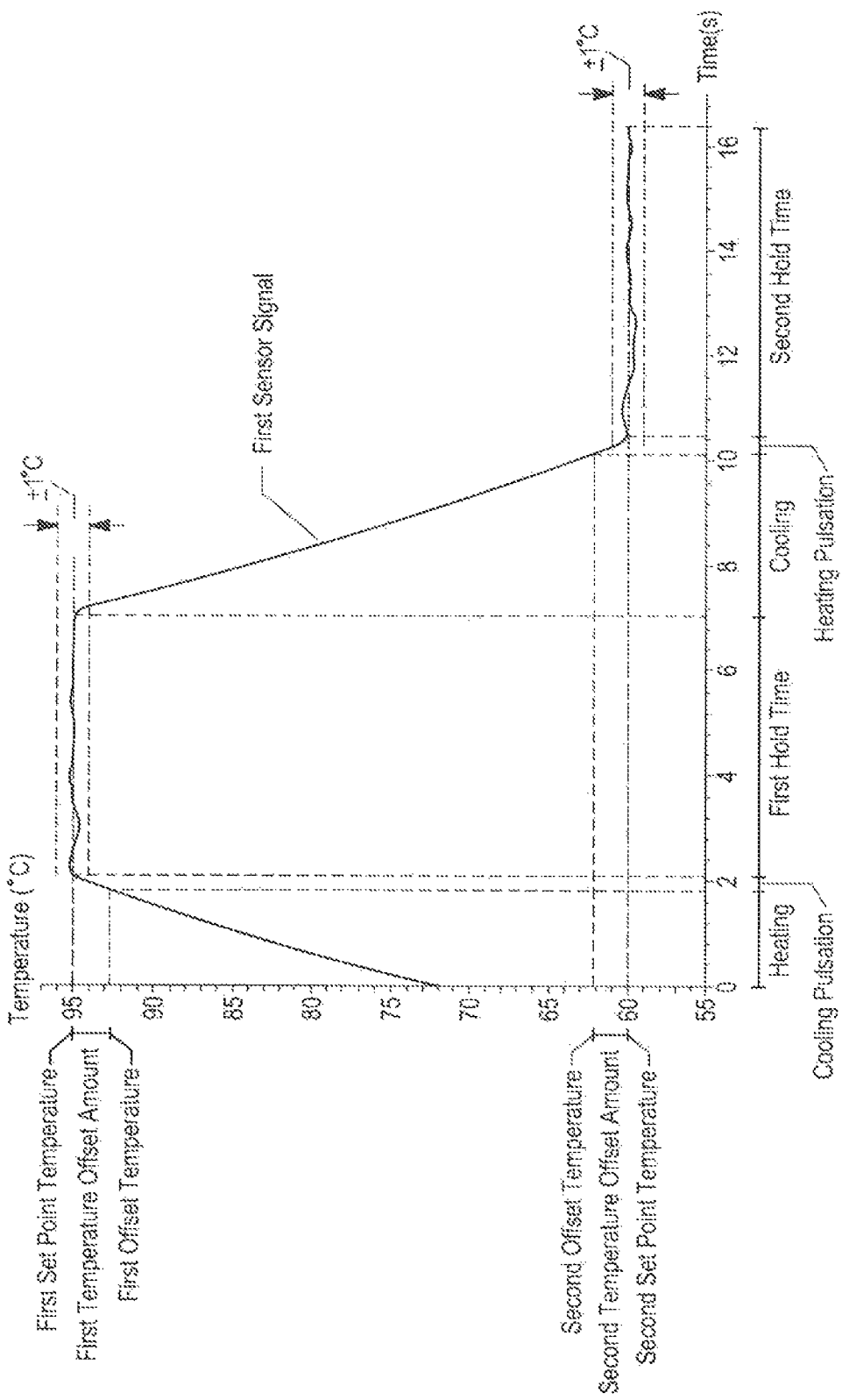

FIG. 6 is, an illustrative, portion of a plot of time and temperature that demonstrates offset temperatures.

DETAILED DESCRIPTION

As will be seen, the teachings herein illustrate various improvements to thermocycler instruments. The thermocycler instruments of the teachings follow the basic principles of WO/2009/105499, in that a sample block (e.g., a sample holder) is sandwiched between opposing thermoelectric devices. The teachings, however address a number of new features for thermocycler instruments that successfully and unexpectedly improve efficiency and operation of the instruments as compared with instruments that do not employ such features. An example of a commercially available product in accordance with many of the present teachings, and many of the teachings of U.S. Provisional Application No. 61/492,002, filed Jun. 1, 2011, is available from Streck, Inc. of La Vista, Nebr., catalog #s 250000, under the designation PHILISA®.

The teachings, herein, accordingly, are premised upon an improved thermocycler instrument, and specifically a thermocycler instrument for use to amplify nucleic acids (e.g., DNA), by which denaturation, elongation and annealing steps may be repetitively performed until exponential amplification of a template occurs, such as in accordance with a user inputted protocol. The instrument thus includes a combination of components selected and adapted for relatively rapid cycling. For example, the teachings herein contemplate use of instruments within the teachings for performing nucleic acid amplification over a period less than about 30 minutes, less than about 20 minutes, less than about 15 minutes, less than about 10 minutes, or even less than about 5 minutes. The teachings herein contemplate that such amplification rates can be successfully employed for sample sizes of greater than about 2 microliters, 10 microliters, 30 microliters, 50 microliters, or even 70 microliters (e.g., a sample size of about 25 microliters). Relatively large yields of amplified nucleic acids (e.g., at least levels detectable by gel electrophoresis) are possible over a relatively short period of time. The unexpected ability to perform such rapid amplification on relatively large sample sizes is one of the advantageous aspects of the present teachings. Aspects of the instrument also may be premised upon the recognition that thermal inertia characteristics of structures and materials used for thermocycler instruments can impede the rate at which thermal cycling can take place as may intrinsically occurring lags that occur due to electronic processing capabilities of an instrument. Accordingly, the present teachings also pertain, in various aspects, to unique approaches to addressing such obstacles.

The teachings herein envision the efficient operative employment of at least one first thermal cycling element for thermally cycling a sample in generally opposing relationship with at least one second thermal cycling element for thermally cycling the sample. Though other devices may be employed, the thermal cycling element for thermally cycling the sample typically will be one or more thermoelectric devices ("TEDs"). Thus, it, is envisioned that a first TED and a second TED may be in generally opposing relation with one another. They may be generally identical and may be controlled to operate substantially identically with each other. A sample holder may be employed to carry a sample (e.g., a sample enclosed or otherwise carried within a sample container, such as a tube). The sample holder may be adapted to receive at least one sample (e.g., a sample carried in a sample container such as a tube) and to be disposed (e.g., in a sandwiching relationship) between the thermal cycling elements (e.g., between the first TED and the second TED). An exemplary tube that may be received by the sample holder is described in commonly owned U.S. application Ser. No. 13/452,419, the contents of which are incorporated by reference for all purposes. The sample holder may be in thermal conducting relation with the thermal cycling elements. The thermal cycling elements may each include at least one heat exchanger (e.g., a suitable heat sink) for transferring heat relative from or to each of the cycling devices (e.g., the first and second TEDs).

As with other hardware components herein, the above components may be configured and positioned in a way to afford efficient heat transfer to and from a sample. They may be configured and positioned in a way to help potentially reduce thermal inertia obstacles to efficient heating or cooling. They may be configured and positioned in a way to achieve substantially uniform heating or cooling rates to a plurality of samples that may be carried within the sample holder. Thus, the first-TED and second TED may both operate to heat and/or cool one or more samples simultaneously in an effort to achieve a more uniform heating and/or cooling. They may be configured and positioned in a way to substantially account for the thermal phenomena of the components in executing temperature control.

The teachings envision the use of suitable temperature sensing componentry. For example, the componentry may be such that two or more sensors monitor (e.g., simultaneously and/or continuously) at least two temperature conditions each originating in a location remotely of each other within the thermocycling device. For example, one sensor might sense a condition with the above-rioted sample holder that approximates the temperature to which the sample is being subjected. That is, the temperature conditions are selected so that they, can be relied upon as being related to (e.g., generally corresponding with in a direct manner) the temperature within the sample holder, which may be indicative of the temperature of a sample located within the sample holder. Another sensor might sense a temperature condition of a component, such as a heat exchanger, that provides useful information in accounting for the thermal inertia and thermal interactions during heating, cooling, and temperature holding. The componentry also is adapted to deliver information (e.g., via electrical signaling) corresponding with one or more sensed temperature conditions.

The thermocycling device may also include at least one air mover for circulating hot air out of the thermocycler device. Desirably, the air mover, if employed, is adapted for exhausting air from the thermocycling device.

The teachings also contemplate a method (e.g., a computer-implemented method) for operating a thermocycler (such as the thermocyclers as described herein) for amplifying nucleic acid (e.g., DNA (deoxyribonucleic acid)) of a sample (e.g., a patient sample, such as a human patient sample). The method may include obtaining user input such as in the design of a desired PCR protocol. The method may include a step of displaying one or more user interfaces. Such user interfaces may be configured so that a user is able to input operational instruction protocol information for operating the thermocycler. Such instruction information may be selected from one or any combination of at least one temperature setting, number of cycles to be performed, times for one or more cycles, hold times at one or more temperatures, or the like. The method may include a step of receiving user operational instruction protocol information inputted by the user. The method may include a step of causing the thermocycler to execute a protocol for nucleic acid amplification on the basis of the operational instruction protocol information inputted by the user. The method may include a step of storing (e.g., in a suitable memory device in communication with the instrument) operational instruction protocol information inputted by the user. The method may include a step of displaying for a user previously programmed operational instruction protocol information so that the user can modify such information for designing a protocol. The method may include a step of receiving information about a temperature condition to which a sample is being subjected and causing such information to be displayed to a user substantially in real time. The method may include a step of providing a user with an opportunity to start, stop and/or pause a protocol during execution of such protocol on a sample. The method may include a step of outputting data about an actual or proposed protocol. The method may include one or any combination of other steps of storing notes inputted by a user, providing a preview of a protocol before causing a thermocycler to execute the protocol, performing a diagnostic check to ascertain operability of a thermocycler. By way of illustration, FIGS. 3A-3J illustrate graphical user interfaces that may be employed for obtaining user inputted information and/or outputting information to the user.

The teachings herein also contemplate at least one non-transitory computer readable medium comprising program instructions for performing the methods (or any of the steps) as described in the above. The teachings thus envision at least one computer software program including code that provides instructions to hardware for performing PCR which, when executed by at least one suitable electronic processor or other computer processor, performs the methods (or any of the steps) as described in the above. The teachings also contemplate a system for performing a PCR amplification reaction, the system comprising a device including a memory storage medium for implementing the program instructions of the non-transitory computer-readable medium. The memory storage medium may be on a computer (e.g., a computer having a processor with a processing speed of at least about 1.67 GHz, such as an Inspiron Mini 1018, from Dell). The computer may employ a Windows®-based operating system, or some other like system. The computer may be a tablet. The computer may be/a smartphone device. The above system may include a thermocycler in accordance with the present teachings, one or more devices for collecting information about the temperature condition of the sample holder, and an output device for displaying data obtained or generated by the analyzing device. The output device may be a display panel associated with the computer. Multiple functions of the software may be caused to be performed by code on a single non-transitory storage medium, or on multiple media. For example, functions may reside on firmware associated with a controller that is on-board the thermocycler instrument. The non-transitory storage media may be physically located proximate any instrument it controls (e.g., within the same housing, within the same room, within the same facility, such as a laboratory or hospital). The non-transitory storage media may be remotely located relative to the instrument (e.g., it may be on a remotely located, server, such as part of a user controlled network, as part of a cloud system, or otherwise).

The thermocycler of the present teachings also includes electrical circuitry adapted to signally interface with one or more control device, the at least one temperature sensor, the at least one air mover and one or more of the thermal cycling elements (e.g., at least one of the first and second TEDs). A housing is configured for generally enclosing the above components. The housing may include at least one air exhaust structure, such as a port, at least one air inlet structure, and at least one sample access opening. The housing and the at least one air mover may be assembled together so that air within the housing can be exhausted from the housing, such as through the at least one exhaust port of the housing.

The teachings herein also contemplate methods for operating a thermocycler according to the present teachings. In particular, the teachings contemplate methods to address and overcome potential thermal inertia or other lag obstacles that may arise. By way of example, it is contemplated the methods may include supplying power to a thermocycler that includes at least two generally opposing and spaced apart thermal cycling elements (e.g., TEDs) (which may be substantially identical and operated identically with each other), a sample block therebetween, and heat-exchangers associated with the thermoelectric devices and projecting away from the sample block. For operating devices that employ TEDs as the thermal cycling elements, there may be one or more steps of applying a voltage having a positive polarity and a negative polarity for powering the at least two generally opposing and spaced apart thermoelectric devices of the thermocycler (e.g., via an H-bridge circuit). The methods may include one or more steps of applying a voltage for powering an air mover circuit for rotating an impeller of an air mover (e.g., a blower or fan) for convectively expelling air from the thermocycler. The methods may include a step of modulating the pulse width of any signal delivered to the TEDs, the air mover, or both. For methods that operate TEDs, there may be a step of controlling the polarity of the voltage that is applied to the TEDs to repeatedly alternate the operation of the TEDs between a first condition of supplying heat to a sample holder and a second condition removing heat from the sample holder. The methods envision controlling operating parameters, (e.g., via at least one closed loop control system, such as a suitable modified proportional-integral-derivative controller), by which there may be steps of obtaining a sample holder electrical signal corresponding with a temperature within the sample holder, obtaining a heat, exchanger signal corresponding with a temperature within at least one of the heat exchangers, and controllably adjusting the speed of the air mover, and the supply of power (e.g., via voltage control) to the thermoelectric devices on the basis of either or both of the sample holder signal or the heat exchanger signal. That is, control may be exerted as to any of a number of operational parameters (e.g., the duration, nature and/or amount of an electricity supply, such as the amount of power, the amount of time of delivery, polarity, and any pulse width modulation). Such step may employ a step of performing one or more calculation that is employed for issuing a signal, such as to cause a temperature change for transforming the sample, to account for measured thermal inertia indicators (e.g., temperature conditions of the sample holder and the heat exchanger). Additional steps will be apparent from the teachings herein, wherein it is envisioned that the teachings of a functional feature also contemplate the teachings of a step of employing such feature for performing such function.

With more attention now to particular details of the respective components of the present teachings, in general, the teachings, herein envision the use of thermoelectric devices (TED) for rapidly heating and cooling a sample, even though other thermal cycling elements are possible. In a typical device in accordance with the teachings herein, at least one first TED and at least one second TED are employed. The first TED and the second TED may be in generally opposing and spaced relation with one another. For example, they may be generally parallel with each other. They may be generally identical and operated substantially identically. The TEDs may be generally elongated and have a planar outer surface. The planar outer surface may be generally vertically oriented, or otherwise oriented in a direction generally parallel with the direction of entry into the thermocycler of a sample container. The planar outer surface also may be adapted to be in thermal communication (e.g., in conductive communication, directly or indirectly, with or without an intermediate media such as a thermal paste) with a sample holder. For example, any such thermal paste may have a thickness of at least about 0.008 mm and less than about 2 mm. The thermal conductivity of the paste at 36° C. may be at least about 0.8 W/m*K and less than about 3 W/m*K.

As will be appreciated, the TEDs operate on an effect by which a semiconductor-based solid state component can function as a heat pump. The application of a power source (e.g., a DC power source) to a TED causes heat to move from a first side of the TED to the other second side, cooling the first side while, heating the second side. A change in polarity of the applied voltage causes a reversal of the above phenomenon. The TEDs for use in the present teachings envision electrical leads connected with an array of solid state elements in electrical communication with each other and the leads, and which are typically supported on at least one common substrate, and more desirably sandwiched between opposing substrates. Multiple TEDs may be employed in combination. Multiple arrays of solid state elements may be carried on one or more support structures. One or a plurality of arrays of solid state elements may be part of a single TED-Multiple TEDs may be carried on a common support structure. The TEDs may be fabricated to include one or more internal temperature sensing device's. The TEDs may be fabricated to include a metallization pattern for interfacing with one or more other devices. The TEDs may be sealed (e.g., with an insulating polymeric material such as a room temperature vulcanizate such as silicone, an epoxy, or some other material). One or more of the TEDs may include a polymeric substrate, a ceramic substrate, a thin film substrate, a plated substrate, or any combination thereof. The TEDs may be provided as a module of two or more discrete TEDs. For example, they may be stacked relative to each other. They may be side by side relative to each other. One or more through holes may be employed in a TED.

The TEDs herein preferably exhibit the following performance characteristics: a value of ΔT Max (Maximum temperature differential in Celsius at $Q_c=0$ and iMax) of at least about 60° C., 70° C., or even 80° C.; and a value of $Q_c$ (Maximum heat pumping capacity in watts at iMax and Δt=0) of at least about 128 W. The TEDs may have a maximum thickness ($t_{max}$) of about 0.5 mm to 5.0 mm. Examples of TEDs suitable for use in the teachings herein are available from Ferrotec (USA) Corporation under the Model Number 85542 Rev A based upon model 7201/131/150BS/L390. An iMax (maximum input current in amperes at $Q_c=0$ and ΔT Max) may be of 15.0 A. The TEDs are preferably assembled with materials optimized for temperature cycling applications by minimizing the impact of thermally induced stresses.

It is believed that conventional wiring may be employed to supply a voltage to the TEDs. However, it is believed that larger lead wires (which may or may not be employed) reduce the amount of parasitic heat generated in the power transmission to the TEDs, by employing AWG 18 PTFE-coated lead wires that have a larger than conventional diameter, by at least about 5%, 10% or even about 20%. To account for the size differences, TEDs may need to be modified to provide a surface of suitable size and shape to which the wiring may be attached (e.g., soldered).

Any sample holder of the present teachings is adapted to receive at least one sample. It may be adapted to receive a plurality, of samples. For example, the sample holder may be a solid block of material that has one or a plurality of bores therein, such as bores extending inwardly from an exterior surface (e.g., a sample holder upper surface). The bores are adapted to receive either a sample (via a sample container), and/or at least one temperature sensor. The sample will be generally disposed between the first TED and second TED in thermal conducting relation sandwiched between opposing TEDs. The sample holder may be a substantially solid metal block that is free of any voids in it for passing any heat exchange fluid. The block may contemplate no passage of any liquid coolant therethrough. The sample holder is preferably a highly thermally conductive metal. For example, it may be substantially pure silver block, or a silver alloy-containing silver in a major quantity (i.e., greater than 50 percent by weight). The sample holder may be a sterling silver alloy. It may be half hard sterling silver, a dead soft sterling silver, or a combination of both. It may include an alloy of silver and copper (e.g., greater than about 85 wt. %, greater than about 90 wt. %, such as about 92.5% silver, with the balance copper). It may be coated with a thin layer of an additional substance to enhance its heat transfer or wear characteristics.

The sample holder herein may be of suitable size and shape to achieve generally uniform heating and cooling characteristics of the holder so that a plurality of samples can be heated and cooled under substantially identical conditions. One approach herein is to employ a block structure having a generally rectangular prism external geometry. The structure may have a first (e.g., top) surface, a second (e.g., bottom) surface, a first side surface adapted to be in thermal conducting relationship with at least one first thermal cycling element (e.g., a TED), a second side surface adapted to be in thermal conducting relationship with at least one second thermal cycling element (e.g., a TED), and a pair of opposing spaced apart end surfaces that connect the first and second side surfaces.

A plurality of bores are defined within the holder. The bores may each have a longitudinal axis. The bores may be formed to at least partially extend from the first surface toward the second surface. The bores may extend entirely through the block to define a through passage from the first surface through to, the second surface or to one of the other surfaces. Such through-passage may be suitably employed in combination with a detector (e.g., an optical detector) for a real-time detection system for monitoring amplification. Any bore structure herein may be defined so that a through passage including the bore structure extends through an outer surface of the sample holder in at least two separate locations. For example, any sample tube receiving bores of the sample holder may extend from end to end, and/or from end to side through the sample holder. In this manner or some other suitable manner, it may be possible to position a monitoring device (e.g., an optical monitoring device) in monitoring position relative to any sample positioned in such bore. In this manner, the teachings herein are adaptable and may be practiced with real-time monitoring of a PCR operation, such as by using a suitable optical monitoring device. Of course, it is possible that the bores may start at one end and terminate before they reach an opposing end.

The bores may be defined by an internal wall having one or more cross-sectional dimensions. For example, the internal walls defining the bores may have a generally circular cross-sectional geometry. They may have an oval cross-sectional geometry. The cross-sectional geometry may vary along the length of the walls. For example, the cross-sectional geometry may reduce as it proceeds from the first surface toward the second surface. Such reduction may be in a stepwise formation, a gradual continuous formation, or both. Such reduction may be such that the walls have a constant slope (e.g., a constant slope taper having an angle from about 0.10° to about 3.0° (e.g., from about 0.196 to about 1.91°)). The opening in the first surface may have a chamfer that extends only partially, into the holder (e.g., less than about 10%, or even less than about 1% of the length of the holder). Any bores that are adapted to receive a sample may have a longitudinal axis, and a cross-sectional profile along such axis that is circular, oval, or some other predetermined geometry. The cross-sectional profile of the bores along its axial direction may be constant, or it may vary along the height of such bores. For example, the walls defining the bore may be generally frustoconical, and include a sloped portion. One approach is to employ a wall structure that tapers along the holder, and has a generally oval profile along the tapered portion.

The sample holder may have one or more temperature sensor bores (e.g., a bore with a longitudinal axis that is generally parallel with the longitudinal axes of any bore for receiving a sample). The temperature sensor bore may be located generally in the center of the holder between the side surfaces and the end surfaces. The temperature sensor bore may be generally cylindrical. It may be defined as a through passage from the first surface to the second surface. The bore may be defined to include a shoulder at one end to assist in maintaining the sensor in a desired location within the bore. The temperature sensor may include a sensing element that directly contacts a wall defining such bore, or the sensing element may be spaced apart from any such wall. As an example, a suitable thermal conductive paste may be located between the wall defining the bore and the temperature sensor so that thermal communication is facilitated between the sample holder and temperature sensor. The thermally conductive paste may be present to fill any voids present to enhance thermal communication.

The sample holder may have a length (i.e. the distance between the end surfaces), a height (i.e., the distance between the first surface and the second surface), and a width (i.e., the distance between the side surfaces). The ratio of the height to the width may be at least about 4:1, at least about 7:1 or even at least about 10:1. The ratio of the height to the width may be less than about 25:1, less than about 18:1 or even less than about 12:1. The ratio of the length to the width may be at least about 10:1, at least about 15:1, or even at least about 20:1. The ratio of the length to the width may be less than about 40:1, less than about 30:1, or even less than about 25:1. The ratio of the length to the height may be at least about 1:1, at least about 1.5:1 or even at least about 2:1. The ratio of the length to the height may be less than about 4:1, less than about 3:1 or even less than about 2.5:1. By way of example, without limitation, a holder may have a ratio of length to height to width of about 60:30:2.7. Thus, expressed in units such as millimeters (mm), a holder may have a length of about 60 mm, a height of about 30 mm and a width of about 2.7 mm.

The width of the wall of the block from side walls to the location where the wall defining the bore in which a sample lube is inserted may be about 20% to about 35% (e.g., about 25%) of the overall width of the holder. Adjoining bores may be spaced relative to each other in a generally equidistant manner. For example, the longitudinal axis of each adjoining bore may be separated by a space of about 1/(N+0.5) times (x) the length of the holder, where N equals the number of bores. The approximate spacing between the outermost cross-sectional dimensions of the bores may be approximately the same as the width of the holder. Thus, for a holder having dimensions of about 60:30:2.7, and having 8 sample receiving bores, the spacing between the outer edge of respective bores may be about 2.7. The spacing from the outermost edge of the end bores to the ends of the holder may also be about 2.7. The dimensions expressed herein may be millimeters (mm) or some other unit, the holder may be substantially solid in that it contains no internal channels through which a coolant or refrigerant is pumped or otherwise agitated or convected.

The sample holder thus may have one or more bores defined therein with a wall geometry that substantially complements the geometry of the outer wall surface of such tubes. The cross-sectional geometry may be generally circular with a cross sectional dimension being a diameter. The cross-sectional geometry may be generally oval with a major axis and a minor axis. The bores may be defined to receive in contacting relationship a sample tube of a type described generally in commonly-owned application U.S. Application Ser. No. 61/477,785 and U.S. application Ser. No. 13/452, 419 incorporated by reference herein for all purposes.

Such a tube may include a closure portion. A strap may integrally connect to the closure portion and may be configured for defining a living hinge. The tube may include a body portion having a longitudinal axis and an outer wall generally circumscribing the longitudinal axis. The body portion may be integrally and hingedly connected with the closure portion by way of the strap. The body portion may include a head portion that has an opening through which a sample is dispensed, and a sample portion having a first outer wall dimension. The sample portion may further include a closed distal end and a wall structure that includes an outer wall and an inner wall, the inner wall may define a hollow cavity within which the sample resides as a sample volume after it is dispensed through the head portion and into the sample portion, the closed-ended hollow sample portion may be generally elongated along the longitudinal axis and may be configured for elastic deformation along a portion of its length, including in a direction that is generally transverse to the longitudinal axis so that at least a portion of the wall structure compressively deforms and engages the bore wall in the sample holder, and the first outer wall dimension of the sample portion reduces to a smaller second outer wall dimension, the tube may be free of any other internal structure in use. The tube may be formed to hold from about 5 µl to about 300 µl. The tube may be formed to hold less than 100 µl. The tube may be formed to hold less than 30 µl.

The sample receiving bores of the sample holder may have a portion for complementarily receiving all or part of a body portion of the tube. For example, it may have a portion for complementarily receiving only at least a portion of a sample portion of the tube, or at least a portion of a sample portion of the tube and at least a portion of a head portion of the tube. The bore may be adapted to receive both the head portion and the sample portion of a tube. In such instance, the length of the portion of the bore that receives the sample portion of the tube may be greater than the length of the head portion by a factor of at least about 6. The portion of the bore for receiving the closed-ended hollow sample portion of the tube may have an outer profile that tapers along the longitudinal axis so that it narrows as it approaches the location, in the bore that would be juxtaposed with the closed end of an inserted (e.g., a generally fully inserted) tube. The bore may taper so that the portion that receives the sample portion of the tube has a wall surface that tapers generally continually (e.g., with a substantially constant slope) along substantially the entirety of the length of the sample portion so that it narrows in at least one axis transverse to the longitudinal axis of the bore from a first wall dimension to a second wall dimension that is less than about one half (e.g., about one third) of the first outer wall dimension as it approaches the portion of the bore that is substantially juxtaposed with the closed end of an inserted (e.g., a generally fully inserted) tube. The bores may have an opening with a major and minor dimensional axis. For example, it may be a generally oval opening. At the opening, the ratio of the major axis to the minor axis will be about 1.5:1 to about 4.5:1, and more particularly about 2.2:0.7. The bore may taper to an end that has ratio of the major axis to the minor axis will be about 1.2:1 to about 4:1, and more particularly about 3.4:1.3. With both the opening and the end, the ratios may be about 1:1 (e.g., they may be generally circular).

The bores of the sample holder need not be tapered. They may be generally oval in shape along a major portion of their length (e.g., at least 50, 60, 70, 80 or 90% of the length). The bores may be generally rectangular, or have some other geometry.

FIG. 1e of U.S. Provisional Application No. 61/492,002, filed Jun. 1, 2011, illustrates examples of approximate dimensions of a suitable sample holder, and is incorporated by reference herein for all purposes. By way of illustration, one such sample holder may have a width of about 2.74 mm, a height of about 30 mm, and a length of about 60 mm. Each sample bore may have a major axis of about 4.4 mm, and a minor axis of about 1.3 mm. The bores may have an outer radius of about 0.57 mm at the respective corners of the bore that chamfers at the opening at about 45° to an inner corner radius of about 0.51 mm. From center to center of respective bores, there may be a spacing of about 7 mm. From the edge of the outermost bore to the side end of the sample holder there may be a spacing of about 0.5 mm. The bore that receives the temperature sensor may be located substantially half way along the length of the sample holder and may extend substantially the entire height of the holder. For example, it may include a portion (which may be a generally constant portion) that is about 28 mm in height into which a temperature sensor is placed. The respective bores into which the sample tubes are placed may be tapered inwardly substantially along its length, such as for causing the sample tube to engage the bore walls and apply pressure to the tube for enhancing the amount of contact between the holder and the tube and/or making the cross-section more narrow to reduce the distance heat must travel within the sample tube. The dimensions may vary within the above by about 10%, 20%, 30% or more. The relative proportions as to the above are within the scope of the present teachings, and they may be generally the same for larger or smaller sample holders.

The sample holder is also configured so that one or more outer surfaces can be thermally contacted with (e.g., in direct face to face contact with or in thermal communication with by means of indirect contact) opposing thermal cycling elements (e.g., thermoelectric devices) for conducting heat between the elements and the holder. The thermal contact may also be facilitated by means of a thermal paste located between the sample holder and thermal cycling elements. For example, the sample holder may have a side surface portion (e.g., a flat side surface portion) that has a complementary shape with an outer surface structure of one or more of the thermal cycling elements (e.g., TEDs). Though the teachings herein address the use of a single sample holder, thermocyclers of the present teachings, may include a plurality of sample holders.

Each of the thermal cycling elements (e.g., TEDs) may have one or more associated heat exchange structures (e.g., heat sinks) for transferring heat from or to each of the TEDs. The heat exchangers, may be in direct or indirect (e.g., via an intermediate conducting layer) thermal contact with (e.g., in direct face to face contact with) at least one of the TEDs. Suitable heat exchangers may be a relatively highly conductive metal. Suitable heat exchangers may include a plurality of fins. Such fins may be generally parallel relative to each other, or disposed at an angle (e.g., less than about 90°, 60°, 30° or even 15° relative to each other). One approach employs a plurality of fins that project in a direction generally perpendicular to a side of the sample holder. The fins each may have an outer surface configuration, which may be generally planar. Thus, it is possible that the generally planar outer surfaces will be oriented generally perpendicular to the longitudinal axes of any sample bores in the sample holder (e.g., generally horizontally). As will, be discussed, it is also contemplated that the generally planar outer surfaces will be oriented in the same general direction as an axis, of an axial fluid mover employed for exhausting air from the housing. One or more of the heat exchangers may include suitable structure to receive and carry a temperature sensor. For example, a fin or other structure may be sufficiently thick that a temperature sensor can be threadably attached to it.

The location of each TED with regard to the sample block may improve the uniformity of temperatures to which samples located within the sample block are exposed. As an example, the TEDs may be located along the sample block such that wiring from one TED may extend from one end of the sample block, and the opposing TED may be flipped in an opposite direction so that the wiring from the opposing TED may extend from an opposing end of the sample block. The temperature experienced by each bore may vary by a specified amount if the TED wiring extends from the same end of the sample block on both TEDs. However by rotating the opposing TED 180°, the temperature experienced by each bore may vary by less than that specified amount.

The thermocycler of the present teachings will employ suitable temperature sensing componentry. Such componentry may be adapted to approximate the temperature condition to which a sample is being subjected. It may be adapted to measure a thermal condition of one or more of the thermocycler components (e.g., a TED, a printed circuit board (PCB), a heat exchanger, a sample holder, an air mover, or otherwise). The componentry may typically include at least two temperature sensors. The at least two temperature sensors may be adapted and located to monitor at least two temperature conditions each originating in a location remote to each other. Such temperature conditions may be an indicator that approximates the temperature to which a sample is being exposed. The temperature sensor componentry also will be adapted to deliver signals corresponding with the temperature conditions it monitors, the signals may be used for controlling operation of one or more components.

The signals may be used in a controlling operation that accounts for thermal inertia characteristics of at least, one component of the thermocycler and also may be employed to take into account operational lags intrinsic in the operation of the electronic components. For example, such controlling operation may be one that causes a series of heating and cooling operations within a single heating or a single cooling stage. In this manner, the controlling operation may employ the signals in a heating stage that includes heating by one or more thermal cycling element to heat the sample holder to a temperature below a predetermined setpoint temperature, followed by an operation of cooling by the one or more thermal cycling element during the heating stage for a period of time, such as until the temperature sensed in the sample holder (e.g., from an interior region that approximates the location of a sample relative to outer surfaces of the holder) reaches the setpoint temperature. The controlling operation may employ the signals in a cooling stage that includes cooling by one or more thermal cycling element to cool the sample holder to a temperature above a predetermined setpoint temperature, followed by an operation of heating by the one or more thermal cycling element during the heating stage for a period of time, such as until the temperature sensed in the sample holder (e.g., from an interior region that approximates the location of a sample relative to outer surfaces of the holder) reaches the setpoint temperature.

The temperature sensing devices herein may be any suitable device for the intended application. They may be selected from any of a variety of sensing devices. For example, they may be a resistance temperature detector, a thermocouple, a thermistor, an integrated circuit (IC) temperature sensor or any combination thereof. They may incorporate a positive temperature coefficient sensing element or a negative temperature coefficient sensing element.

The one or more sample holder temperature sensors employed for the sample holder may be suitable resistance temperature detectors (RTDs). An example of a suitable sensor is available from Minco under the designation S207192PD with 25.4 mm glass coated ceramic-element length, 100 Ω±0.1% resistance at 0° C. and an alpha value of 0.00385Ω/Ω/° C. The sensor for the sample holder may be positioned so that a sensing element of the sensor is located within an interior region of the holder, and may be generally juxtaposed with any sample carried in the holder, so that it provides information approximating the temperature to which the sample is being exposed on the basis of like positioning within the sample holder. The sample holder may be fitted with a plurality of temperature sensors to detect a temperature gradient along the sample holder.

At least one thermal probe (e.g., temperature sensor) may be associated with at least one of the heat exchangers. The probe may be suitably configured to be mounted to a structure associated with any such heat exchanger. For example it may be mountable to a body, fin or other support structure. In this manner, the temperature that is monitored will be that on a surface or interior of the heat exchanger. As indicated, such temperature condition on the surface may differ from the temperature condition within the interior of the holder. By employing this sensor, suitable control over heating and cooling operations can be achieved by taking into account differences in temperature that may arise, such as differences arising as between the sample holder side of the thermal cycling elements and the heat exchanger side of the thermal cycling elements.

The probe may be threaded for threaded engagement with the heat exchanger. The probe may include a sensor element at least partially surrounded by an electrically isolated metallic (e.g., aluminum) case, with suitable conductive leads (e.g., tinned copper leads) in signaling communication with the sensor element. The probe may exhibit a nominal electrical resistance value at 25° C. of less than about 50 kΩ, less than about 30 kΩ, less than about 20 kΩ, less than about 16 kΩ or even less than about 12 kΩ. The probe may exhibit a nominal electrical resistance value at 25° C. of greater than about 3 kΩ, greater than about 6 kΩ or even greater than about 9 kΩ (e.g., about 10 kΩ). The probe may exhibit a beta value tolerance ($B_{25/100}$) of below about 5000 K. The probe may exhibit a beta value tolerance ($B_{25/100}$) of above about 3500 K. For example, the probe may exhibit a beta value tolerance ($B_{25/100}$) in the range of about 4150 to about 4450 K. The probe may exhibit a resistance tolerance value of $\Delta R_R/R_R$ of within about ±10%, a beta value tolerance of within about ±3%, or both. An example of a suitable thermistor is available from EPCOS AG under the product number B57045K103K.

For any of the temperature sensing devices herein, it is possible that a signal amplifier is employed to amplify the signal obtained from the sensing device. By way of example, a controller or other circuit component associated with a PCB of the thermocycler device may be adapted to supply a power signal to a temperature sensor. The signal is such that it generally avoids any distortions in temperature readings due to any self-heating of the sensor. The signal amplifier desirably will amplify the resulting relatively small signal outputted from the sensor up to a suitable value (e.g., about 0.5 V to about 4.5 V signal) for temperature measurement over the range of temperatures that are likely to be measured by the thermocycler. The amplified signal may range from about 5% to about 95% of the full range of the controller. That resulting voltage range closely matches the 0 V to 5 V capability of the controller employed. The amplifier circuitry is designed so that is it relatively insensitive to external heat issues. For instance it may employ a suitable combination of resistors and amplifiers that have negligible changes with their own internal temperature change. The amplifier circuitry may be free of any whetstone bridge.

At least one air mover may be employed for exhausting air from the thermocycling device. The air mover may include a housing at least one motor operably connected with an impeller for rotating the impeller. The impeller may rotate via a sleeve, bearing or by ball bearings. The housing may have a suitable shroud, such as one that includes or adjoins a guard grille with struts. The shroud may have a length along the rotational axis of the air mover that spans to include and substantially surround the impeller, and that extends to a location substantially adjoining an inner wall of the housing. In this manner, the air mover is able to draw air in a generally uni-directional manner, which may have a path through the base of the thermocycler device or any other air inlet, optionally across a printed circuit board (PCB), over at least a portion of the heat exchanger, and through the shroud, before exhausting from a port of the housing.

The air mover may be a suitable blower or fan. The air mover may be capable of and/or operate for passing at least about 55, 70, 85 or even 100 cubic meters per hour (or 30, 40, 50 or even 60 cubic feet per minute). It may operate to rotate at one or more desired rates, and at a rate of at least about 500, 1000, 2000 or even 3000 rotations per minute. The air mover may be an axial air mover or a centrifugal air mover. The air mover may be relatively compact, (e.g., less than about 100 mm in its largest dimension). The air mover may be DG powered. As described herein, it is an axial air mover. An example of an air mover for use herein is available commercially from ebmPapst, under the designation 3412NGHH.

The thermocycler may include a chassis structure that supports various components within the housing. The chassis may include a frame that has forward portion, a rearward portion, an upper portion, and a base portion. One or more (e.g., each) of the forward portion, rearward portion, upper portion, and base portion may include a through-opening. For example, the base portion (which may be adapted so it is spaced apart from a support surface, such as a table or countertop, on which it rests) may have an opening for allowing entry of air into the thermocycler from beneath the thermocycler. The chassis may include one or more support brackets for carrying one or more components. The chassis may be made of a plurality of metallic components, and/or polymeric components that are suitably joined together (e.g., by welding, mechanical fastening, or otherwise). The chassis may be configured so that it supportably receives a sample holder in at least the upper portion. The sample block may be supported so that a bottom of the holder is suspended above a void. The void is defined to have a suitable geometry so that it optionally receives a real-time detection device (e.g., a device for optically monitoring any reaction that takes place within one or more sample tubes placed in the sample block), the chassis may also be suitably configured so that a housing can be placed in covering relationship over the chassis for substantially enclosing the components, while still allowing the entry of air into the thermocycler (e.g., through the bottom portion of the chassis). The chassis may be such that it has one or more heights. For example, the forward portion of the chassis may have a shorter height than the rearward portion of the chassis. The chassis may have one or more adjustable feet.

As indicated, a housing may be carried on the chassis. The housing may be configured for enclosing thermal cycling elements (e.g., TEDs) of the thermocycler, any associated heat exchangers, temperature sensors, and at least a portion of the electrical circuitry. The housing may have an open bottom. The housing may include at least one air exhaust port. The housing may include at least one air inlet port. The housing may include at least one sample access opening. The housing and at least one air mover may be assembled together so that air within the housing can be exhausted from the housing through the at least one exhaust port of the housing. It is possible that the housing may have a single exhaust port, such as one located-along a side of the housing. The housing may have a geometry that approximates the geometry of the chassis. For example, the housing may be such that it has one or more heights; the forward portion of the housing may have a shorter height than the rearward portion of the chassis, the housing may expose certain portions of the chassis. The housing may include openings for allowing access to electrical power connections, data communication ports or the like. The housing may be a suitable molded plastic configuration. The housing may include an upper portion that is hingedly connected with the chassis. The housing may include an upper portion that is hingedly connected with a lower portion, both the upper portion and the lower portion substantially covering the chassis. One or more components of the housing may be connected with the chassis, such as by mechanical attachment (e.g., by one or more fasteners).

In general, the thermocycler instrument of the present teachings may be configured with electrical circuitry adapted to receive an electrical signal from at least one power supply, and signally interface with one or more control device, the at least one temperature sensor, the at least one air mover and the at least one first and second thermal cycling elements (e.g., TEDs). The one or more parameters are selected from an amount of power delivered to the at least one-thermoelectric device, a polarity of the at least one thermal cycling element, a pulse width of power being delivered to the at least one thermal cycling element, the time that power is delivered, or any combination thereof. The circuitry may be such that it is adapted to shut down operation of one or more electrically driven components in response to a sensed malfunction condition. The circuitry may be such that it is adapted to deliver an indication of the status of operation of the thermocycler (e.g., one or more lights for indicating a power on condition, a cycling condition, or both). The circuitry optionally may be adapted to perform a function of operating a device for monitoring amplification of a nucleic acid of a sample. Circuitry may include one or more electrically conductive paths (e.g., hard-wired cables, wires, traces, etc.). The circuitry may include a plurality of circuit portions that collectively define a part of or a complete single circuit. The circuitry may include a plurality of circuit portions that collectively define a plurality of circuits. As to the latter, such plurality of circuits may be independent circuits, which nonetheless may be configured to function cooperatively with each other to perform the recited functions of the present teachings.

The conductive paths may be part of at least one printed circuit board ("PCB"), such as a PCB including conductive paths on two or more surfaces in electrical communication with each other through conductive vias. For example a ground plane (e.g., a copper ground plane) may be employed in spaced relation with another powered plane. A number of components may be in signaling communication with each other by way of electrical cabling or other suitable wiring.

By way of illustration, the teachings herein contemplate that circuitry for various operations of the thermocycler are carried in at least one PCB that may also carry a controller. The PCB may be adapted to include a connector to accept power and ground lines from one or more power supplies (e.g. a 12 V supply). It thus may include one or more fuses to help prevent damage to electronic components. The PCB may be adapted to include suitable elements (e.g., a plurality of capacitors, such as three capacitors of various sizes) for helping to minimize fluctuations and noise in the incoming power supply. Suitable elements may be employed to selectively direct the flow of current. For example, diodes may be included to prevent current from the power supply (e.g., a 12 V supply current) from flowing in the wrong direction. The PCB may have suitable connectors and amplifier circuitry for one or more temperature sensors.

The PCB may be connected directly with a controller, such as by way of one or a plurality of headers. A board of the controller may also be mechanically fastened or otherwise attached to the PCB through at least one header, the PCB power supply signal (e.g., the 12 V signal) may be sent to the controller and used to power the controller. The controller may have a lower voltage (e.g., about 5 V) regulator that is used to power the lower, power portions of the PCB through that same header. With other headers (e.g., two or more other, headers), the controller may provide digital outputs used to (a) control power to the air mover, optionally the speed of the air mover (e.g., by employing a pulse width modulation (PWM) circuit); and/or to provide the signals to control the H-bridge enable, direction, and PWM lines for controlling operation of the thermal cycling elements (e.g., the TEDs). By way of yet another possible header, the controller board may employ one or more analog input lines to record signals corresponding with one or any combination of any sensed temperature condition of a heat sink, a 5 V signal to ensure the components are being powered properly, a sensed temperature condition of the PCB, a ground signal to ensure the components are being grounded properly, a sensed temperature condition of the sample holder, or the main power supply (e.g., 12 V supply) signal, to ensure that the instrument and TEDs are being powered properly (as to the latter, a voltage divider may be employed so that the controller sees a voltage within its capability, such as about 4 V). As may be necessary, suitable circuit elements (e.g., resistors, capacitors or a combination thereof) may be added to prevent power spikes to the controller board and to smooth rapid spikes and noise, in any of the signals from the temperature sensors.

The power line on the PCB resulting from an output from the controller's regulator is generally used to power various operational components on the PCB. This is a reduced voltage supply (e.g., about 5 V from an initial 12 V supply). The signal may be fused and include one or more capacitors (e.g., two) to smooth most of the voltage irregularities and noise. This line may be used to power one or more temperature sensors. In advance of delivering power to the sensors, the voltage may be reduced to a sufficiently low level so that self-heating of the sensor does not occur in a manner that would distort temperature readings. For example, the voltage may be divided by a factor of at least about 5, 10, 20, 50 or higher (e.g., to about 0.1 V). As a specific example, the voltage may be divided by a factor of 10.

It is possible, that any PCB employed may include one or more boards that individually are divided into at least one digital section and at least one analog section. These sections may be separated by a gap in a copper ground plane employed. Most of the digital lines may be in the digital section (crossing only over a small region that separates the two sections). All of the analog lines may be in the analog section. This separation of analog from digital helps to minimize electrical noise that may be created in the analog signals.

For certain of the wiring it is possible that the wiring will be selected and employed in a manner for avoiding the emission and/or absorbance of electromagnetic or radio frequency interference. One or more ferrites may be attached to the electrical circuitry. A ferrite may be attached to the AC power inlet wires. A ferrite may be attached to the USB wiring. A ferrite may be attached to the 12 V voltage supply line. The one or more ferrites may have a typical impedance of less than about 500Ω, less than about 350Ω, or less than about 250Ω at a 100 MHz test frequency. The one or more ferrites may have a typical impedance of greater than about 50Ω, greater than about 100Ω, or greater than about 200Ω at a 100 MHz test frequency (e.g., about 240Ω). An example of a suitable ferrite is available from Fair-Rite Products Corp. under the product number 0431167281.

As gleaned from the above, the control functions of the thermocycler device herein may be consolidated on one or more suitable controller or other computer processor devices. For example, there may be an onboard control device (e.g., one or a combination of two or more microcontroller printed circuit boards) located on and/or or at least partially within the thermocycler. The onboard control device may include one or more programmable electronic processors (e.g., microprocessors) or other computer devices which may include suitable memory, such as flash memory. It may include one or more input and/or output interfaces (e.g., pins) for communicating with one or more externally located peripheral devices, computer processors or both. The onboard control device may include one or more analog inputs for receiving signals from one or more of the operational components of the thermocycler (e.g., one or more of the temperature sensing devices). The onboard control device may include one or more pulse width modulation circuits for controlling power (e.g., duty cycle) to one or more of the operational components of the thermocycler (e.g., the thermal cycling elements (e.g., TEDs), the air mover, or each). The onboard control device may include an interface for receiving a power supply, and suitable circuitry for distributing power to one or more of the operational components of the thermocycler. An example of a suitable controller includes the Arduino Mega 2560 or other controllers having like functional features and/or at least such performance characteristics. Such a device, as with others that may be employed herein, may include any suitable combination of a plurality of (e.g., 54) digital input/output pins (of which 14 can be used as PWM outputs), a plurality of (e.g., 16) analog inputs, a plurality of (e.g., 4) UARTs (hardware serial ports), an oscillator (e.g., a 16 MHz or faster crystal oscillator), an external connection port (e.g., for USB connection), and a power jack. It may also include an ICSP header, and a reset button. The control device may be powered by an external power-supply, by another powered device (e.g., by a computer or other device, via a USB or other like connection).

One or more components of the circuitry may be for the purpose of delivering a signal obtained by a temperature sensor about a temperature condition to the controller. Once received by the controller, the controller may perform one or more algorithms on the basis of the signal that directs the operation of one or more of the components (e.g., the air mover, the TEDs, or otherwise). In order to allow for the use of a low voltage signal to one of more of the temperature sensors (e.g., RTDs), the temperature sensing circuitry may include one or more amplification elements, e.g., one or more operational amplifiers, that increase the outputted signal from the temperature sensor by a factor of at least about 5, 10, 20, 50 or higher. An example of a suitable amplifier is a complementary metal oxide semiconductor amplifier, such as is commercially available from Texas Instruments under Model No. OPA2333-HT. The operational amplifier may be employed with one or more input current limiting elements. Two or more operational amplifier elements may be employed in series and may be used in parallel.

One possible approach to employing a first temperature sensor circuitry (e.g., a sample holder temperature sensor circuit portion) may employ a suitable connection to a power supply (e.g., a relatively low voltage supply as compared with a main power supply, such as a 5 volt supply). The circuitry generally will include a suitable temperature sensor (e.g., and RTD sensor) that is in signaling communication with one or more signal amplification elements to deliver an amplified signal to the control device that originated from the power supply, after having passed through the sensor and any amplification element. More particularly, the circuitry may include one or more components (e.g., one or more capacitors) for minimizing electrical voltage spikes or otherwise smoothing the signal prior to the signal passing through the temperature sensor (e.g., an RTD sensor). The circuitry may include one or more components for amplifying the signal that issues from the temperature sensor. For example, there may be one or more amplification circuit components (e.g., two amplification circuit portions). If a plurality of amplification components exists they may differ from each other in regard to the amount of amplification. By way of example, one or more of the amplification circuits may include an operational amplifier in a circuit that includes at least one resistor, and at least one capacitor. The signal issuing from one such amplification circuit may feed directly into an operational amplifier of another such amplification component. The amplification components are selected to desirably increase the voltage that arises from the temperature sensor to a voltage that approaches the initially supplied voltage (e.g., about 5 V). The resulting signal is delivered to an analog input of the control device. The circuitry may contain one or more grounds. This circuitry may be suitably employed for a temperature sensor that is employed within a sample holder of the thermocycler of the present teachings. Two or more of such circuitry portions may be employed within the present thermocyclers.

The teachings herein also provide for one or more additional temperature sensor circuitry. For instance, there may be a circuit board temperature circuitry portion employed for providing information about a temperature that the circuit board is experiencing. There may be a component (e.g., heat exchanger) temperature sensor circuitry portion employed for providing information about a temperature condition that the component is experiencing.

The circuit board temperature sensor circuitry may be connected to a power supply (e.g., a relatively low voltage supply as compared with a main power supply, such as the same 5 volt supply that supplies the first temperature sensor circuit), the circuit board temperature circuit may include one or more fuses, and/or one or more components for smoothing the voltage (e.g., two or more, different capacitors), the circuitry may be grounded, the signal issuing from the temperature sensor (e.g., a thermistor) may be split into two parallel paths one of which includes at least one element (e.g., a resistor) for reducing voltage so that the resistance of the temperature, sensor can be measured and thus the temperature of the temperature sensor can be calculated.

The component temperature sensor circuitry may be connected to a power supply (e.g., a relatively low voltage supply as compared with a main power supply, such as the same 5 volt supply that supplies the first temperature sensor circuitry), the circuit may be grounded. It may include one or more elements (e.g., a resistor) for reducing voltage, the signal issuing from the temperature sensor (e.g., a thermistor) may be routed to the control device for processing.

The thermocycler may have a main power circuitry portion that supplies power to an air mover if present, the TEDs, or each. The main power circuit may include power supply communication circuitry for communicating with the control device when the thermocycler is in a powered operational mode. Any such power supply communication circuitry may also include one or more indicator (e.g., a light, such as an LED) to an operator that indicates that the thermocycler is in a powered operational mode. A grounded power supply, such as a 12 V direct current power supply, supplies a voltage through a power line (which may include a suitable fuse) and which has a branch that powers the indicator, the voltage is subjected to one or more circuit element (e.g., a plurality of capacitors) for smoothing the signal and avoiding potentially problematic power spikes. The voltage is then supplied to the control device, such as along one input branch via a voltage input port. Another branch of the voltage may be supplied via a grounded line, through an analog input port, such voltage being provided in a reduced state (e.g., reduced by a resistor element) and for the purpose of communicating to the control that the main power supply is in a power on state.

The circuitry of the present teachings may function to power and operate an air mover (e.g., rotate an impeller of an air mover) whenever the main power supply is switched on. The circuitry thus may include one or more components configured to run the air mover, when the main power supply is switched to an on position. By way of example, a suitable transducer arrangement (e.g., a pair of negative field effect transducers) may be employed for functioning as a switch that remains generally in an on operating position.

Though suitable circuitry for operating other thermal cycling elements may be employed, the present teachings particularly address illustrative circuitry for operating TEDs. Per such circuitry, two or more thermoelectric devices are in electrical communication with a power supply (e.g., the main power supply) for causing the TEDs to power on and off. A circuit component is in switching signaling communication with the applicable control device and the TEDs. The circuit component may include a suitable H-bridge circuit element. The switching of the H-bridge element may be signaled by the control device to switch between a first and second polarity for controlling heating or cooling. The signal may be a pulse width modulated signal issued from the control device.

Desirably, circuitry employed herein for controlling the operation of the TEDs will supply electricity to any TEDs from the power supply. The circuitry also will include one or more component that functions to rapidly switch polarity of the voltage applied (e.g., direct current voltage) to the junctions of the TEDs according to signals provided by the applicable controller (e.g., from the on-board controller previously discussed). The present rapid polarity switching circuitry component may be a stand-alone component, of it may be commonly carried with any thermocycler controller device. The present rapid polarity switching circuitry, component may be provided as part of a printed circuit board, and may optionally be mounted to its own heat exchanger or sink. One approach is to employ a suitable H-bridge circuit. The H-bridge circuit may be a solid state circuit. The rapid polarity switching circuitry may include suitable amplifier switching circuitry to switch a high power electrical line (such as 12 V and up to 25 A) with a low power signal line (such as 5 V and less than 1 A). The rapid polarity switching circuitry may include a suitable interface for control signal input. For example, it may be adapted for receiving pulse width modulation signaling, signaling for identifying desired polarity, enabling signaling, and/or for grounding. An example of one suitable control device for the thermoelectric devices herein is available from Accuthermo Technology Corp. under the model no. FTX700 or FTX700D.

Desirably, the circuitry employed herein for controlling the operation of any air mover will supply electricity to any air mover from the power supply. The circuitry may also include one or more-component that functions to alter the speed of an impeller of the air mover. The variable air mover speed is advantageous in that it reduces noise and that the controller adjusts the air mover so as to maintain optimal heat exchanger temperature. Alteration of air mover-speed may assist in more precisely controlling the temperature of the heat sinks. The air mover may have certain on-board electronics. For example, it may have a suitable sensor (e.g., a Hall effect sensor) for monitoring rotational speed. Such sensor may be in signaling communication with any applicable control device of the thermocycler.

In general, the air mover control circuitry (if an air mover is included) will receive power from a suitable power supply, such as the main power supply (e.g., 12 V direct current supply). The air mover control circuit also may be in operative communication with a relatively reduced voltage supply. For example, it may be from a pulse width modulated power supply (e.g., issued by way of the control device) voltage of a reduced voltage (e.g., about 5 V). The reduced voltage is supplied for operating, one or more suitable circuit element (e.g., a switching device, such as a pair of nFETs) for switching the available power from the main supply on or off to the air mover.

One or more components of the thermocycler may employ a suitable, switch that shuts down operation of the component in the event of a malfunction, such as a runaway temperature condition. Such a switch may employ a temperature sensitive element (e.g., a bimetallic temperature sensitive disc), which may be a surface mounted element, and which will remain in a switched open or closed position below a certain temperature, but then (respectively) close or open a circuit upon reaching a certain predetermined temperature (e.g., above about 140° F., 155° F., 170° F. or higher) or range of temperatures (e.g., the previous mentioned temperatures ±about 7° F.). An example of such a switch is a thermostat available from Selco Products Company under the designation OA-170. Any switch employed may be ah automatic, reset switch (e.g., a thermostat) or a manually reset switch. In the event of shutdown of main power supply, the controller is still configured to receive a reduced voltage signal (e.g., a 5 V signal via a USB interface, from some external device such as a computer). The latter signal may be such that it could signal the external device that a shutdown has occurred.

Other variations within the circuitry are possible. For example, it is possible that data acquisition electronics may be employed to directly receive information about a temperature condition, directly control an H-bridge circuit, and/or directly amplify a signal. A USB plug or other port may be employed for connection with a remote computer device which may contain a non-transitory storage medium on which software is provided having code for instructing the performance of one or more steps herein. Temperature sensors may employ a three wire structure. A whetstone bridge may be employed with a temperature sensor (e.g., a three wire RTD) to compare the resistance of the RTD with a known resistance of a reference resistor, such as a resistor on a PCB.

The circuitry and the components desirably are selected and operated so that power may be supplied to the thermocycler, while at least two generally opposing and spaced apart thermal cycling elements, and preferably thermoelectric devices, have a sample holder (such as one configured as a block) therebetween, and while heat exchangers associated with the elements (e.g., thermoelectric devices) are projecting away from, the sample holder. For example, a voltage having a positive polarity and a negative polarity may be applied for powering the at least two generally opposing and spaced apart thermoelectric devices of the thermocycler, such as by way of an H-bridge circuit. A voltage may be applied to an air mover circuit for powering the rotation of an impeller of the air mover. In this manner air may be convectively expelled air from the thermocycler. Desirably, the polarity of the voltage that is applied to power the thermal cycling elements (such as thermoelectric devices) is suitably controlled to repeatedly alternate the operation of the elements (e.g., thermoelectric devices) between a first condition of supplying heat to the sample holder and a second condition removing heat from the sample holder. At the start of operation, and during operation of one or more of the thermal cycling elements (e.g., thermoelectric devices), one or more temperature conditions will be experienced by the sample holder, and particularly at a generally internal location within the sample holder. The one or more temperature conditions can be monitored with the temperature sensor componentry. For example, for the various embodiments herein, it is possible to employ a step of obtaining at least one sample holder electrical signal corresponding with at least one temperature condition within the sample holder, e.g., at least one temperature condition at a location within the interior of the sample holder that is substantially juxtaposed with at least one sample supported within the holder. The location of a temperature sensor in the holder is such that the temperature condition it senses may approximate the temperature condition that the sample would be subjected to, while undergoing heating and cooling within the sample holder.

In addition to the sample holder temperature, temperature of at least one remote location may be monitored, such as a temperature of at least one of the heat exchangers may be monitored. For example, a signal from a temperature sensor associated with one or more heat exchangers may be obtained.

In this manner it is believed possible to more accurately monitor and control operation of the thermal cycling elements (e.g., thermoelectric devices) for efficient overall operation. That is, it is contemplated that one or more steps may be employed for controllably adjusting any air mover, the supply of power (e.g., via the voltage) to the thermoelectric devices, or both, on the basis of either or both of the sample block signal or any heat exchanger signal.

More particularly, in accordance with one of the aspects of the present teachings, component operation lag and/or thermal inertia of one or more of the components (e.g., the sample holder) may result in a change in a sensed temperature condition relating to a sample temperature condition, even when heating or cooling of the sample has been stopped (such as following cessation of power delivery to any thermal cycling element). The teachings herein envision the employment of a sensed temperature condition of a remote element such as a heat exchanger which may be exploited to adjust the temperature control parameters of the thermocycler to facilitate close thermal control of the sample holder. A difference in that temperature condition and the temperature condition sensed from within the interior of the sample holder may then be employed advantageously for causing one or more of the thermal cycling elements (e.g., TEDs) to undertake a heating or cooling operation within a respective cooling or heating stage. In this manner, the temperature of the sample may be prevented from exceeding a predetermined maximum temperature during heating, or falling below a predetermined cooling temperature. A braking of the heating or cooling thus occurs (such as during a terminal portion of a heating or cooling operation within a stage), and may be employed to slow the rate at which the predetermined setpoint temperatures are reached to help minimize overshoot or undershoot. In this manner, relatively high rates of heating or cooling may be maintained for as long as possible.

Figure 1A:
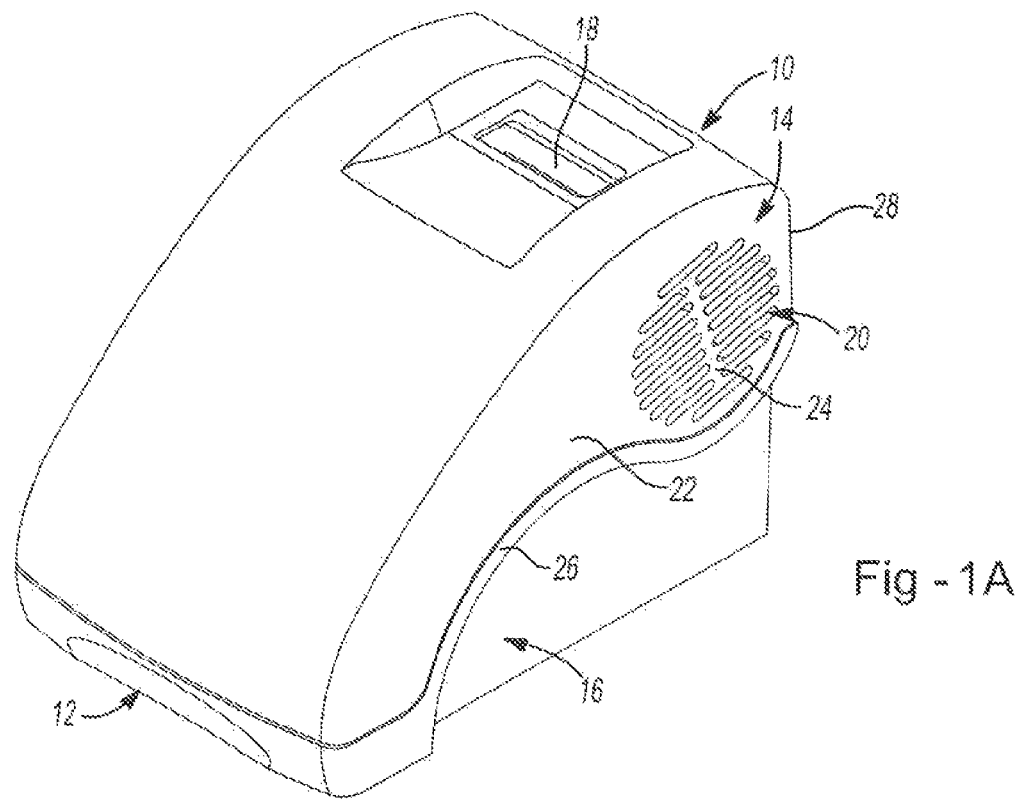
FIG. 1A is a front perspective view of an illustrative thermocycler of the present teachings.
Figure 1B:
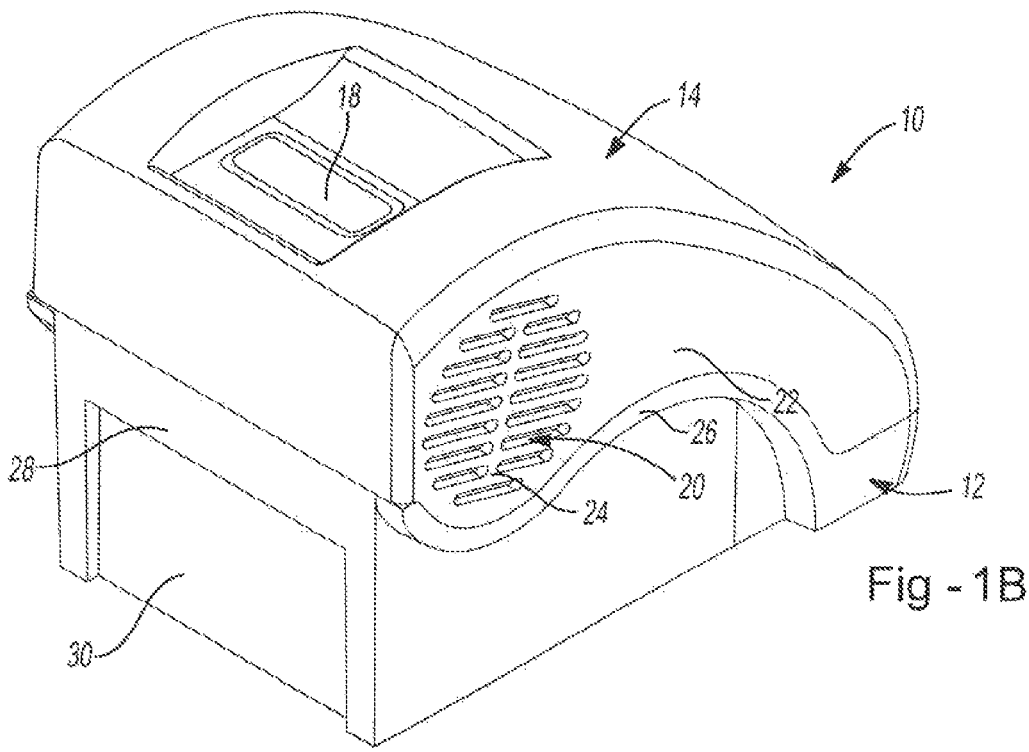
FIG. 1B is a rear perspective view of the thermocycler of FIG. 1A.
Figure 1C:
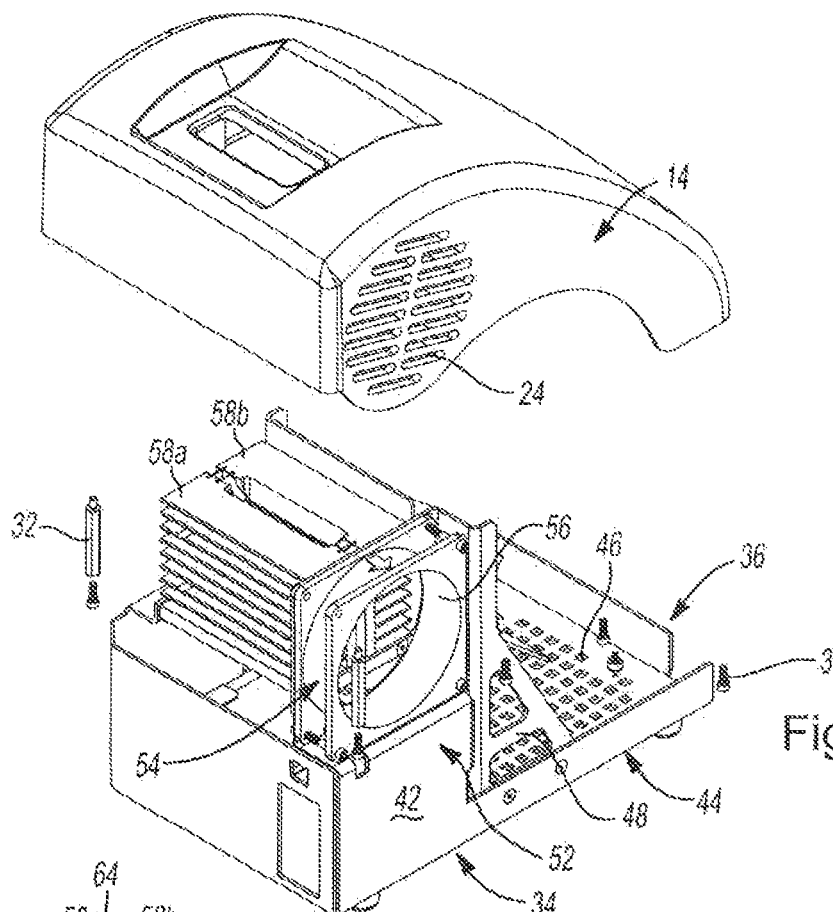
FIG. 1C is a rear exploded perspective view of the thermocycler of FIGS. 1A and 1B, without a bottom housing portion.

With reference to the accompanying drawings, an example of a thermocycler instrument in accordance with the present teachings is further illustrated. Turning to FIGS. 1A and 1B, there is shown a thermocycler 10 having a housing 12 having an upper portion 14 and a lower portion 16. The upper portion may have a generally arcuate overall sidewall structure, and may have a front wall that may be arcuate as well, but is depicted as being generally straight in the portion spanning between the opposing side walls. As seen, the upper portion may have a width that is larger than the width of the lower portion over a majority of the length of the housing. The housing includes, a sample access opening 18 in the upper portion, through which a sample tube (not shown) is inserted. It may be recessed (as shown) relative to an upper surface of the housing. An optional cover, such as a heated cover (not shown) may be included over the opening 18. A vent portion 20 is formed in a side wall 22 of the housing and includes a grille 24 defining either an air inlet or an exhaust port. The upper and lower portions are engaged (e.g., sealingly engaged) with each other by way of a generally sinusoidal or arcuate edge 26 of the upper portion. A rear end 28 of the housing 12 may optionally include a port structure 30 to provide internal access within the housing. The housing may include other openings adapted to receive electrical cable connections (e.g., as illustrated by a generally rectangular opening in a bottom a corner of a chassis portion 34 in 1C). With reference to FIG. 1C, the upper portion 14 and the lower portion 16 may be connected to each other with suitable fasteners 32.

Figure 1D:
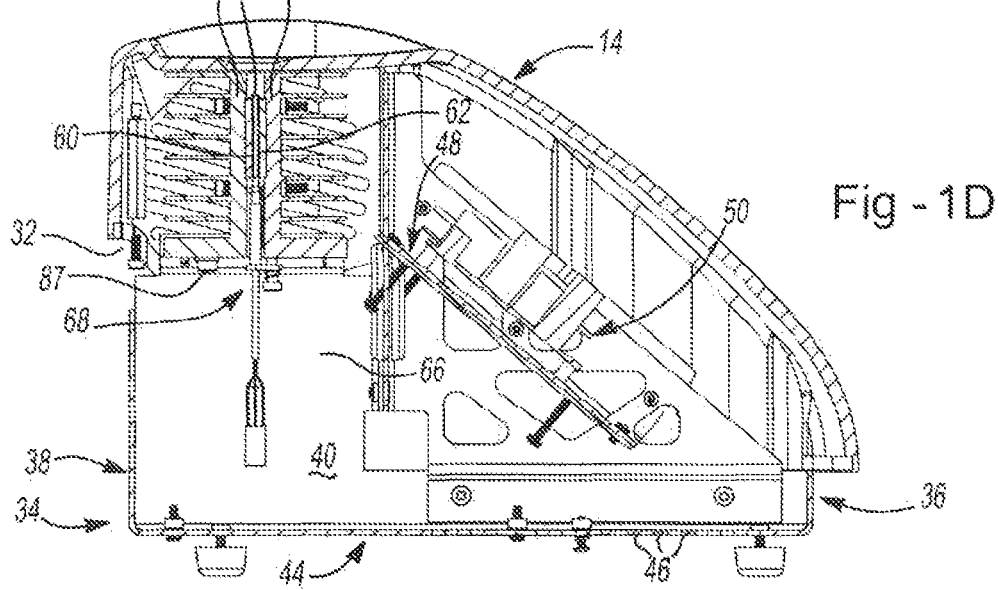
FIG. 1D is a side sectional view of the thermocycler of FIGS. 1A-1C.

As seen in FIGS. 1C and 1D, the housing may cover a chassis portion 34. The chassis may include a frame structure (e.g., shown as being generally rectangular, though other shapes are possible) that includes a forward portion 36, a rearward portion 38, a first side portion 40, and a second side portion 42. A base portion 44, which desirably is spaced above a rest surface (such as by optional adjustable feet), may include a plurality of air hole openings 46, so that air may enter the thermocycler from beneath the thermocycler. A support bracket structure 48 (e.g., shown angularly disposed relative to the base portion in FIG. 1D) may support an electronics module 50, which may include one or more printed circuit boards with circuitry for operating the thermocycler. A support structure 52 (e.g., one or more brackets or other support members) may also support an air mover assembly 54 (shown with a fan case 56, and without an impeller and motor, and without an optional further shroud), heat exchangers 58a and 58b, a first TED structure 60, a second TED structure 62 and a sample holder 64. The orientation of fins of the heat exchanger may be as depicted in FIGS. 1C and 1D. For instance, they may project generally parallel to the base portion in a fore and aft direction. A void 66 is defined within the thermocycler, into which a device for monitoring a nucleic acid amplification reaction can be located. The void may be located adjacent to the sample holder, and may be substantially juxtaposed with it, above it, below it, or both. Suitable hardware to supportably receive a temperature sensor may be employed so that the temperature sensor enters the sample holder 64 from a location beneath the sample holder. A second temperature sensor 87 may be employed on a heat exchanger, e.g., on a bottom portion of a heat exchanger, and possibly proximate a free end of a fin of the heat exchanger.

With reference to FIG. 1E1-1E6, as to the sample holder 64 it is depicted to include a block structure 70 having a generally rectangular prism external geometry. The block structure has a top surface 72, a bottom surface 74, a first side surface 76 adapted to be in thermal conducting relationship with the first TED structure 60 (see FIG. 1G), a second side surface 78 adapted to be in thermal conducting relationship with the second TED structure 62, and a pair of opposing spaced apart end surfaces 80 and 82 that connect the first and second side surfaces. A plurality of sample receiving bores 84 are defined within the block structure. The bores may each have a longitudinal axis (LA) that extends along the length of the bore. As seen more particularly in FIG. 1E, a centrally located temperature sensor bore 86 is shown, and includes a shoulder 88. As can be appreciated, the bore is positioned for allowing a sensor to experience approximately the same temperature to which a sample undergoing PCR is being subjected. References for determining length (L), width (W) and height (H) dimensions are illustrated. The bores are adapted to receive a sample tube, such as the tube 90 of FIG. 1F, which includes a closure portion 92, a body portion 94, and a head portion 96. Desirably it is an integral structure and a strap defining a living hinge 98 connects the closure portion with the body portion.

With reference to the accompanying drawings, an example of circuitry for use in accordance with the present teachings is illustrated in FIGS. 2A and 2B.

The general operation of the illustrative circuit of FIGS. 2A and 2B is explained in the following. Additional reference may be made to Table 1 below, which addresses various of the circuit elements, shown in FIGS. 2A and 2B. Two or more of the circuit elements may be combined into a single circuit element. The function of one or more of the circuit elements may be divided among two or more circuit elements. The performance values specified may vary 10%, 20% or more from those shown. Values specified may vary from those specified, but remain generally within the relative proportionate amounts shown. An example of suitable circuitry is available commercially from Streck, Inc. in its Philisa® instrument identified previously.

TABLE 1

| Element | Function | Specification |
|---|---|---|
| 1130 | LED to display when power is turned on | Blue |
| 1090 | H-bridge, controls power to the TEDs | 600 W power control |
| 1010 | Power supply | 12 V, 300 W |
| 1030 | Air mover | 60 CFM |
| 1020 | Microcontroller board - reads analog voltages, sends results to computer, sends digital voltages to operate air mover, H-bridge | |
| RTD PCB | Temperature sensor printed circuit board (PCB) - Connects and amplifies RTD (temperature sensor), heat sink thermistor, and printed circuit board thermistor. Connects 12 V power, microcontroller board, air mover, and front LED | |
| 1070 | Heat sink - prevents thermal electric devices (TEDs) from overheating | |
| 1040 | TEDs - Heat or cool sample block | |
| 1050 | Sample block - Contain and heat or cool samples located therein | |
| 1060 | RTD (temperature sensor) - reads the sample block temperature | 100 ohm |
| 1210 | Thermostat - turns off power to thermocycler if heat sinks become too hot | 170° F. |
| 1080 | Thermistor - reads the heat sink temperature | 10000 ohm |
| Power Entry Module | Smoothes input AC current, fuses AC current | 10 A, up to 250 VAC |
| Not shown | Ferrites - reduces electromagnetic interference | 240 ohms at 100 MHz |
| R1 | Pulldown resistor - keeps air mover on unless software indicates otherwise | 10000 ohm |
| R2 | Voltage divider for heat sink thermistor - Allows heat sink thermistor resistance (i.e. temperature) to be read | 10000 ohm |
| R3 | Limits current to front panel LED to dim LED brightness to desired level and prevent LED from drawing excessive current | 10000 ohm |
| R4 | Voltage divider for R5 to bring the 12 V power down to 4 V, so it can be read by the 5 V maximum analog input | 2000 ohm |
| R5 | Voltage divider for R4 to bring the 12 V power down to 4 V, so it can be read by the 5 V maximum analog input | 1000 ohm |
| R6 | Limits current from 5 V line to analog input in case of a short or over-voltage condition | 1000 ohm |
| R7 | Voltage divider for R8 to bring the 12 V power down to 5 V, so that the fan is normally on | 12000 ohm |
| R8 | Voltage divider for R7 to bring the 12 V power down to 5 V, so that the fan is normally on | 8660 ohm |
| R9 | Voltage divider with RTD #1 - Allows RTD#1 resistance (i.e. temperature) to be read | 4990 ohm |
| R10 | Voltage divider with RTD #2 - Allows RTD#2 resistance (i.e. temperature) to be read | 4990 ohm |
| R11 | With R13 acts as a unity gain amplifier of RTD#1 signal and allows RTD voltage to be used without drawing unnecessary self-heating current through RTD | 49900 ohm |
| R12 | With R14 acts as a unity gain amplifier of RTD#2 signal and allows RTD voltage to be used without drawing unnecessary self-heating current through RTD | 49900 ohm |
| R13 | With R11 acts as a unity gain amplifier of RTD#1 signal and allows RTD voltage to be used without drawing unnecessary self-heating current through RTD | 49900 ohm |
| R14 | With R12 acts as a unity gain amplifier of RTD#2 signal and allows RTD voltage to be used without drawing unnecessary self-heating current through RTD | 49900 ohm |
| R15 | With R17 and R19 amplifies RTD#1 signal voltage to approximately a 0 V to 5 V range | 36000 ohm |
| R16 | With R18 and R20 amplifies RTD#2 signal voltage to approximately a 0 V to 5 V range | 36000 ohm |
| R17 | With R15 and R19 amplifies RTD#1 signal voltage to approximately a 0 V to 5 V range | 26700 ohm |
| R18 | With R16 and R20 amplifies RTD#2 signal voltage to approximately a 0 V to 5 V range | 26700 ohm |
| R19 | With R15 and R17 amplifies RTD#1 signal voltage to approximately a 0 V to 5 V range | 500 ohm |

TABLE 1-continued

| Element | Function | Specification |
|---|---|---|
| R20 | With R16 and R18 amplifies RTD#2 signal voltage to approximately a 0 V to 5 V range | 500 ohm |
| R21 | Limits current from amplified RTD#1 line to analog input in case of a short or over voltage condition | 100 ohm |
| R22 | Limits current from amplified RTD#2 line to analog input in case of a short or over voltage condition | 100 ohm |
| R23 | Voltage divider with PCB thermistor - Allows PCB thermistor resistance (i.e. temperature) to be read | 10000 ohm |
| C1 | Stabilizes 12 V signal from transient voltage spikes | 10 uF |
| C2 | Stabilizes 5 V signal from transient voltage spikes | 10 uF |
| C3 | Stabilizes 12 V signal from transient voltage spikes | 1 uF |
| C4 | Stabilizes 12 V signal from transient voltage spikes | 0.1 uF |
| C5 | Stabilizes 5 V signal from transient voltage spikes | 0.1 uF |
| C6 | Acts as a frequency filter for RTD#1 signal | 1 nF |
| C7 | Acts as a frequency filter for RTD#2 signal | 1 nF |
| C8 | Acts as a frequency filter for RTD#1 signal | 1 uF |
| C9 | Acts as a frequency filter for RTD#2 signal | 1 uF |
| C10 | Acts as a frequency filter for RTD#1 signal | 1 uF |
| C11 | Acts as a frequency filter for RTD#2 signal | 1 uF |
| C12 | Acts as a frequency filter for RTD#1 signal | 47 nF |
| C13 | Acts as a frequency filter for RTD#2 signal | 47 nF |
| C14 | Stabilizes 5 V signal from transient voltage spikes | 0.1 uF |
| D1 | Flyback diode - Reduces voltage spikes when air mover is turned on or off | |
| D2 | Prevents 5 V current from powering the air mover when the thermocycler is turned off | |
| D3 | Prevents thermocycler from running if 12 V power cable and front LED cable were swapped during manufacture or repair | |
| F1 | Protects PCB from 12 V power surges and protects power supply from shorts on PCB | ⅜ A |
| F2 | Protects fan from 12 V power surges and protects power supply from shorts in the air mover | 1 A |
| F3 | Protects PCB from 5 V power surges and protects microcontroller board from shorts on PCB | ⅜ A |
| H1 through H6 | Headers - connect PCB to other electronics | |
| Q1 | MOSFET - Turns a normally on signal to Q2, unless told otherwise | |
| Q2 | MOSFET - Turns the fan on or off depending on signal from Q1 | |
| T1 | PCB thermistor - measures PCB temperature to detect conditions that are too hot or too cold to safely or properly operate the thermocycler | 10000 ohm |
| U1 (U1a and U1b) | Operational amplifier to amplify RTD#1 voltage to a 0 V to 5 V signal | |
| U2 (U2a and U2b) | Operational amplifier to amplify RTD#2 voltage to a 0 V to 5 V signal | |
| Arduino MEGA 2560 | Microcontroller board - Reads analog voltages, sends results to computer and sends digital voltages to operate air mover and H-bridge | |

With reference to both FIGS. 2A and 2B, aspects of an electrical system 1000 that can be employed in the present teachings are depicted. The system 1000 includes an example, of a power supply component 1010, a controller component 1020, an air mover component 1030, thermoelectric devices component 1040, and a sample, holder component 1050 between the thermoelectric devices. A temperature sensor 1060 (e.g., a RTD) for measuring a temperature condition of the sample holder is in signaling communication with the controller 1020 to provide information about the temperature of the sample holder. Heat sinks 1070 flank the thermoelectric devices 1040. At least one of the heat sinks has a temperature-sensor 1080 (e.g., a thermistor). An H-bridge device 1090 is in signaling communication with the controller 1020 for controllably supplying power (e.g., pulse width modulated power) to the thermoelectric devices so that the polarity of the thermoelectric devices can be switched for heating and cooling. The controller, other circuitry, or each can be mounted on one or more printed circuit boards 1100. Any such printed circuit board may itself include a suitable temperature sensor (e.g., a thermistor). The system may have a suitable interface (e.g., a USB interface) 1120 for communication with a peripheral device, a computer (e.g., a portable laptop, handheld, server, desktop, netbook, tablet, smartphone or otherwise) or some other electronic processor or other computing device hardware (hot shown). One or more indicators (e.g., an LED lamp) 1130 may be employed for indicating the powered condition of the system. The system may further include various circuit portions that cooperate in a manner to controllably operate the thermocycler. For example, there may be an air mover circuit portion 1140, a sample holder temperature sensor circuit portion 1150 (an optional second such portion is shown in FIG. 2B), a heat sink temperature sensor portion 87, a printed circuit board temperature sensor circuit portion 1160, a heat exchanger (e.g., heat sink) component temperature sensor circuit portion 1170, a main power supply circuit portion 1180, a power supply communication circuit portion 1190, an H-bridge signal circuit portion 1200, a malfunction power off circuit component 1210, or any combination thereof. Various cable assemblies may be employed, such as for connecting power supply, thermoelectric devices, H-bridge device, temperature sensors, fans, lights, or other components that reside remotely from any printed circuit board that carries electronic components.

The air mover circuit portion 1140 receives power from a main power supply 1010 (e.g., 12V direct current supply). The air mover control circuit also may be in operative communication with a relatively reduced voltage supply. For example, it may be from a pulse width modulated power supply controlled by the controller 1020. The reduced voltage is supplied for operating one or more suitable circuit element (e.g., a switching device, such as a pair of nFETs, Q1 and Q2, which may be further employed in combination with resistors R1, R7 and R8 in FIG. 2B) for switching the available power from the main supply on or off to the air mover. Optionally, one or more fuses (e.g., fuse F2) may be employed. In general, the air mover (which desirably may be a 12V axial air mover) will be operated so that when the main power supply is on, the impeller of the air mover automatically is switched on in rotating operation.

The sample holder temperature sensor circuit portion 1150 employs a suitable connection to a low voltage supply as compared with a main power supply, e.g., a 5 volt supply. The circuit portion generally, will include an RTD temperature sensor 1060 that is in signaling communication with one or more signal amplification elements (U1A and U1B) to deliver an amplified signal to the control device that originated from the 5V power supply. More particularly, the circuit may include one or more elements, such as a capacitor C10 for smoothing the signal prior to the signal passing through the RTD sensor, or for reducing voltage (e.g., resistors R9, R11, R17, R19 and R22). One or more components for amplifying the signal that issues from the temperature sensor may include combinations of elements (e.g., capacitor and resistor combinations, such as C6/R13 and/or C12/R15) for tuning the amplification. Though described with reference to RTD1 in FIG. 2B, one or more like circuit portions may be employed such as the circuit shown in FIG. 2B for RTD2.

The printed circuit board temperature sensor circuit portion 1160 may also be connected with a 5 volt power supply by way of the controller 1020. The circuit board temperature circuit may include at least one fuse F3, and one or more components for smoothing the voltage (e.g., two or more different capacitors (C2 and C5) in series) ahead of a signal passing through a thermistor 1110. The circuit may be grounded. The signal issuing from the temperature sensor (e.g., a thermistor) may be split into two parallel paths one of which includes an element (e.g., a resistor R23) for reducing voltage ahead of its analog input into the controller.

The heat sink component temperature sensor circuit portion 1170 may be connected to a relatively low voltage supply as compared with a main power supply, such as the same 5 volt supply as above described. The circuit portion may be grounded. It may include one or more elements (e.g., a resistor R6) for reducing voltage. The signal issuing from the thermistor 1080 may be routed to the controller for processing.

The power supply communication circuit portion 1190 may be employed to provide a visual indication through an LED 1130 that the power from the main power supply is on. This circuit portion may also suitably communicate with the controller to signal the controller as to the power state. For example, a signal (e.g., after being smoothed by capacitors C1, C3 and C4) may be passed through an element (e.g., resistor R4) to reduce voltage to a level that is within the operable range of the controller (e.g., to a level of about 4 V), so that the signal can enter the controller 1020 via an analog input pin (e.g., Ain6). The power supply communication circuit portion 1190 may also be grounded via resistor R6.

For the thermoelectric circuit portion 1200, two or more TEDs 1040 are in electrical communication with the main power supply via the controller 1020, which is configured so it can issue a signal, such as a pulse width modulated signal, to the H-bridge, for causing the TEDs to switch on and off (e.g., such as through Dout10), to change polarity (e.g., such as through Dout9), to control the amount of power delivered to the TEDs (e.g., such as by a pulse width modulation control feature through Dout11), or any combination thereof.

It is possible that the thermocycler will include one of more shut down components 1210 that sense a runaway temperature condition and will shutdown power from the main power supply to all or selectively to only some of the components. For example, as seen in FIG. 2A, the shutdown component 1210 is a switch (e.g., a thermostat) associated with one of the heat-exchangers. Thus, if the heat exchanger reached a certain predetermined temperature deemed beyond, the intended range of operation for the instrument, the thermostat would switch off power to the TEDs. Such a switch may employ a temperature sensitive element (e.g., a bimetallic temperature, sensitive disc), which may be a surface mounted element, and which will remain in a switched open or closed position below ascertain temperature, but then (respectively) close or open a circuit upon reaching a certain predetermined temperature (e.g., above about 140° F., 155° F., 170° F. or higher) or range of temperatures (e.g., the previous mentioned temperatures ±about 7° F.). An example of such a switch is a thermostat available from Selco Products Company under the designation OA-170. Any switch employed may be an automatic reset switch (e.g., a thermostat) or a manually reset switch (e.g., thermostat). FIGS. 2a and 2b of U.S. Provisional Application No. 61/492,002, filed Jun. 1, 2011, illustrate additional aspects of the circuitry and are incorporated by reference herein.

The operation of thermocycler devices in accordance with the present teachings includes combinations of various steps, generally including steps of: (a) receiving information (e.g., via signals) from one or more of the temperature sensors; optionally, storing such information in memory; (b) processing the information to determine the appropriate operational parameter to invoke (e.g., the duration, nature and/or amount of an electricity supply, such as the amount of power, the amount of time of delivery, polarity, and/or any pulse width modulation) for operating at least one of the thermal cycling elements (e.g., TEDs) to cause heating or cooling by way of the thermal cycling elements; (c) reversing the polarity employed in step (b), and applying power by way of the reversed polarity for managing the extent of the heating or cooling of step (b); (d) determining the amount of time for applying power pursuant to the step (c) taking into account any necessary stopping time (e.g., to perform one or more braking operations) so that at least one predetermined setpoint temperature is reached; and (e) maintaining the predetermined temperature for a predetermined amount of time (e.g., by employing a modified proportional-integral-derivative (PID) logic, such as for pulse width modulation of the power delivered); and (f) repeating, steps (a) through (e)

until amplification is completed. Other specific operations are discussed subsequently in further detail.

The methods of operating the thermocycler device of the teachings herein may employ one or more steps of issuing, signals for causing heating and codling within a single heating or cooling stage so that the temperature quickly reaches the predetermined setpoint temperature with minimal deviation upon holding at that setpoint temperature. For example, the methods may employ one or more steps of issuing signals for causing heating and cooling within a single heating or cooling stage on the basis of monitoring and analyzing a first temperature condition sensed within a sample holder, and a second temperature condition sensed outside of the sample holder (e.g., on a heat exchanger in thermal conducting contact with the sample holder). In this manner, the signal may take into account potential lag, due to component and/or thermal inertia effects, such as the effect of thermal inertia of the sample holder, the thermal phenomena of the system, such as the impact of heat exchanger temperature upon behavior of the TEDs, and the response time of the temperature sensor. Any of the steps, may be performed by one or more computer processor programmed with suitable software to perform the steps. Thus, even if not expressly set forth herein, the present teachings also contemplate such software (i.e., in a form as embodied on a non-transitory storage medium) and its use in or with the present thermocycler to control amplification of nucleic acid.

The following illustrates with more particularity how software may be employed for allowing a user to operate a thermocycler in accordance with the present teachings. An example of suitable software is available commercially from Streck, Inc. in its Philisa® instrument, as identified previously.

Envisioned herein is software that may include one or more routines or programs on a non-transitory storage medium. One such program or routine may pertain to a user interface functionality which the software includes code for graphically displaying a user interface, instructing input, receiving and storing of user input for developing a PCR protocol. For example, as seen in FIGS. 3A-3G, users may be prompted to select a favorite protocol (i.e., a protocol that is among the more commonly employed of protocols by the user) or a saved protocol, to create a new protocol, or to use a predefined protocol (see FIG. 3B-3D). The selection will allow a user to adjust time, temperature, and cycling settings. Users are prompted to enter temperatures and hold times for each PCR step in a Temperature Settings user interface screen, as shown for example in FIGS. 3E-3G. For example, software herein may include code that causes prompts for a user to input desired temperatures and hold times for a heating stage and a cooling stage within an individual cycle, along with the number or cycles and/or steps under such conditions. Software herein may include code that causes prompts for a user to input the cycling stage conditions with the starting step number, final step number, and the number of cycles in a user interface screen (see FIG. 3G). Users may be provided an opportunity to write protocol notes in a space on a user interface screen such as a protocol instruction box. Users may be provided an opportunity via the software to save a protocol, whereby the software causes the protocol to be saved to a storage medium. Optionally, the user may be prompted to add protocol to a "favorite" list. Users may be prompted via the software to input a user selection in accordance with any other prompts or drop down menu choices illustrated in the user interfaces of FIGS. 3A-3G.

After a protocol has been inputted and/or selected, the software preferably includes code that performs steps of causing to provide instructions to the thermocycler instrument, such as by way of one or more controller on the thermocycler. The protocol may be executed and may be monitored via the software. Thus, after the thermocycler is switched on, the user may be provided with a start button, which when hit will initiate operation of the software for causing the thermocycler to run the protocol.

Once a PCR protocol run is completed, the software may deliver a signal (e.g., a pop up message or other graphical display) indicating to the effect that the "PCR run is completed". The software may be configured so that the run data, resulting temperature graph for the run, and optional run notes may be saved (optional) (see FIG. 3H).

The FIGS. 3H-J and FIGS. 4A-C also illustrates an example of information that the software may cause to display during operation, based upon information it receives about processing conditions being experienced by the sample holder and/or other components of the thermocycler instrument.

The software may be configured and/or operated to automatically launch when a computer onto which it is loaded is switched on. It may be configured and/or operated to be manually launched (e.g., by a user clicking on an icon).

The software may be configured and/or operated so that the first time, the software is opened, a user will be provided with a display that is blank. For instance the display may indicate a "New" blank PCR protocol. The next time the software is opened it may be configured and/or operated so that it will default to the last protocol that was either saved or loaded. The software may be configured and/or operated for providing a user with an option to select a previously designated "Favorite" protocol, open a previously "Saved" protocol, or start a "New" blank protocol. The software may include a pre-programmed protocol and may be configured and/or operated for providing a user with a choice of a pre-programmed "2-step" protocol or "3-step" protocol as a starting point, which the user may edit as desired.

The software may be configured and/pr operated for permitting a user to open a Recently Used or Favorite Protocol. For example, it may cause a button to be displayed on a screen, which can be clicked (e.g., via a mouse controlling a cursor). By clicking a button for "Favorites" a user may be provided by the software with one or more sections such as "Recently used protocols", "Favorite protocols", and/or an Add/Delete User or Category section. The software may be such that it stores a number of recently run and/or favorite protocols (e.g., 3, 5, 10 or more recently run protocols). Date information about the runs (e.g., when run, when saved, or both) may be stored and displayed. The software may fee such that it allows users to define categories (e.g., by run type and/or user names).

The software may be such that it displays a user interface which invites a user to input one or more desired times, temperatures, cycles, notes or any combination thereof, for defining a protocol. It may invite the user to input multiple cycles, which may be the same or different in terms of any of the foregoing parameters. The software may provide the user with an opportunity to add or delete a step (e.g., from a pre-programmed protocol). The software may provide the user with an opportunity input a number of cycles that will be repeated without deviation from a preceding cycle. The software will be such that a user can save any of its protocols or add or delete a protocol to a list of favorite protocols. The software may provide a preview display to a user, by which a proposed protocol is displayed to the user (e.g., in graphical depiction, such as a plot of time versus temperature), and which may also include the protocol time (see FIG. 3H).

After the design, selection or other input into the protocol, the software may provide the user with a display that can start the run (e.g., a button that can be clicked).

Upon a user inputting that, a PCR should commence, the software may initiate a diagnostic check of the thermocycler. The software may also perform a review of inputted values for the protocol, and will prompt corrections if an error by the user has occurred. For example, if there is a protocol issue, such as a blank entry box or an out of range value, then the run will not start.

Assuming no diagnostic or protocol input problems are identified, the software will communicate instructions to the thermocycler (e.g., via a controller on the thermocycler) to cause the thermocycler to perform PCR according to the protocol selected. The software may be such that it substantially continuously receives temperature data from the thermocycler (e.g., the temperature of the sample holder), elapsed time, or both, so that progress of the run can be monitored. The software thus may cause a graphical display to be outputted to the user that displays the actual times and temperatures achieved by the thermocycler. The display may be such that a temperature graph can be expanded for more details or reduced for fewer details. The software may permit a user to stop a run, pause a run, or resume a run. During or after completion of a run of a protocol, the software may be such that it allows the user an opportunity to save data observed from the run. The software may be such that it stores the date and time that each PCR run is started, paused, and stopped. It may also store the instrument serial number, temperature, protocol name and conditions. It may also store information about, any software error messages, including the date and/or time of the error.

Software may include multiple routines or programs in a non-transitory storage medium that includes programming code with instructions for causing a processor or other computer device to perform a method that includes initializing the thermocycler instrument, causing heating or cooling within a stage, dynamically receiving temperature condition information (e.g., from at least two temperature sensors remotely positioned as to each other), making calculations for dynamically altering power delivery to any thermocycling elements (e.g., thermoelectric devices), and/or maintaining a hold temperature, in accordance with a user inputted protocol. The software (one or more aspects of which may be part of firmware associated with a suitable processor, such as a controller processor), may be such as to allow the methods herein to be computer-implement. Thus, as will be appreciated from the above discussion, whether computer-implemented or not, the teachings herein contemplate various of the methods described herein.

By way of illustration, controlling the thermocycler instrument may involve monitoring the at least two temperatures (e.g., the temperatures measured by the first and second temperature sensors) and determining, on the basis thereof, a condition for activation of a process step by which braking is applied, prior to when the temperature conditions within a sample holder reach a setpoint temperature. Temperature values employed may be actual values or may be values that are directly or otherwise related to the actual value. Thus, it is also within the scope of the teachings to employ for control operations values that are not actual temperature values but adjusted temperature values. Temperatures may be measured other than from within a sample holder, provided that the temperature is used for controlling operation for heating or cooling any samples within the sample holder achieves the desired setpoint temperatures while substantially avoiding undershoot and overshoot.

By way of further illustration, one method for controlling operation of the thermocycler instrument may include any combination of the following steps: receiving at least one first setpoint temperature predetermined by a user, the at least one first setpoint temperature being a maximum temperature to which a sample is to be heated for polymerase chain reaction (e.g., for denaturation and/or elongation) of at least one sample; receiving at least one second setpoint temperature predetermined by the user, the at least one second setpoint temperature being a minimum temperature to which a sample is to be cooled (e.g., for annealing) of the at least one sample; receiving at least, one first hold time corresponding with an amount of time predetermined by the user during which the temperature of the sample holder is maintained generally at the at least one first setpoint temperature; receiving at least one second hold time corresponding with an amount of time predetermined by the user during which the temperature of the sample holder is maintained, generally at the at least one second setpoint temperature; causing at least one thermal cycling element to heat a sample holder; receiving a first sensor signal from a first temperature sensor corresponding with a temperature of the sample holder (e.g., a temperature within the sample holder); receiving a second sensor signal from at least one second temperature sensor that is located externally of the sample holder (e.g., temperature of a heat exchanger); determining a value of any first temperature offset amount (TOFFSET1) based upon the temperature reading from the at least one first and second temperature sensors; causing heating of the sample holder (e.g., at substantially full available power such as about 200 to about 250 Watts (W)), until the sample holder reaches a first offset temperature that is below the first setpoint temperature by the first temperature offset amount; at the time the first offset temperature is reached, causing a cooling pulsation of the at least one thermal cycling element during the heating stage for a sufficient amount of time so that the temperature arrives within about 1° C. (or even about 0.25° C.) of the first setpoint temperature and further heating of the sample holder is interrupted; causing the temperature to be maintained within about 1° C. (or even about 0.25° C.) of the first setpoint temperature for the first, hold time; causing at least one thermal cycling element to cool a sample holder (e.g., such as at substantially full available power, such as about 200 to about 250 Watts (W)); receiving a signal from the first temperature sensor corresponding with a temperature of the sample holder; receiving a temperature reading from the at least one second temperature sensor that is locate remotely from the sample holder; determining a value of any second temperature offset amount (TOFFSET2) based upon the temperature reading from the at least one first and second temperature sensors; causing cooling of the sample holder until the sample holder reaches a second offset temperature that is above the second setpoint temperature by the second temperature offset amount; at the time when the second offset temperature is reached, causing a heating pulsation of the at least one thermal cycling element during the cooling stage for a sufficient amount of time so that the temperature arrives within about 1° C. (or even about 0.25° C.) of the second setpoint temperature and further cooling of the sample holder is interrupted; and causing the temperature to be maintained within about 1° C. (or even about 0.25° C.) of the second setpoint temperature for the second hold time;

optionally repeating the above steps for a predetermined number of cycles until the amplification desired by the user is achieved.

Values of TOFFSET1 and TOFFSET2 may be repeatedly and/or continually determined within a single stage, within a cycle or both.

By way of further illustration, one such method for controlling operation of a thermocycler instrument herein may include steps of receiving at least one first setpoint temperature of at least about 85° C., to which the at least one biological sample is to be heated in the sample holder for polymerase chain reaction, and at least one second setpoint temperature of below about 70° C. to which the biological sample held in the sample holder, is to be cooled for annealing of the at least one biological sample; maintaining a heating rate of at least about 8° C./second (e.g., at least 10° C./sec, at least 12° C./sec or 15° C./sec) until a first offset temperature amount below (by no more than about 7.5° C. below) (e.g., in the range of about 1 to about 2.5° C.) the first setpoint temperature is reached for the sample holder; when the first offset temperature is reached, pulse cooling the sample holder to slow the heating rate until the sample holder is within about 1° C. (or even about 0.25° C.) of the first setpoint temperature; maintaining a cooling rate of at least about 6° C./second (e.g., at least about 8° C./sec or 10° C./sec) until a second offset temperature above (by no more than about 7.5° C.) (e.g. in the range of about 1 to about 2.5° C.) above the second setpoint temperature is reached for the sample holder; when the second offset temperature is reached, pulse heating the sample holder to slow the cooling rate until the sample holder is within about 1° C. (or even about 0.25° C.) of the second setpoint temperature; monitoring a first temperature corresponding with a temperature of the sample holder and a second temperature corresponding with a temperature of the heat exchanger; adjusting an amount of time, a temperature or both at which the steps of pulse cooling, the pulse heating or both commence based upon the first temperature and the second temperature; and repeating the above steps for a predetermined number of cycles until the amplification desired by the user is achieved. As seen, one of the unique aspects of the teachings herein is the ability to monitor temperatures for determining and compensating for the effects of thermal inertia, system lag, and/or thermal behavior of the hardware components (e.g., TEDs). For example, one of the unique aspects of the teachings herein is the monitoring temperatures of a sample holder (e.g., within a sample holder), and a location remote of the sample holder (e.g., a heat exchanger), and the calculation (which may be on a repeated and ongoing basis within a stage and/or across a plurality of stages or cycles) of an offset temperature at which temperature braking is initiated for minimizing overshoot and undershoot (e.g., so that overshoot and undershoot, if any, is less than about 1° C., or even 0.25° C. of a setpoint temperature), within a stage, and still maintaining a generally rapid rate.

By way of summary, an illustrative methodology may include a plurality of cycles, each including a heating and a cooling stage, until amplification is completed, the methodology may include a heating stage step that includes a step of: (a) causing heating at full available power until the temperature reaches a temperature that is offset from (e.g., below) a setpoint temperature; and (b) causing cooling during the heating stage for a certain amount of time so that the temperature arrives at the setpoint with minimal overshoot (e.g., no greater than about 1° C. (or even about 0.25° C.)). The amount of time engaged in cooling at full power may be minimal. As an example, substantially no cooling step may be required in heating to the setpoint temperature. The methodology may then include a cooling stage that includes a step of: (a) causing cooling toward a cooling setpoint temperature at full available power until the temperature is offset from the setpoint temperature; and (b) causing heating for a certain amount of time so that the temperature arrives at the setpoint with minimal undershoot (e.g., no greater than about 1° C. (or even about 0.25° C.)). Unlike other traditional thermocycler control methodologies, this illustrative methodology minimizes the amount of time for the heating and cooling stages to be completed while maintaining precise control of the temperature.

Again, the amount of time engaged in heating at full available power may be minimal. As an example, substantially no heating step, may be required in cooling to the setpoint temperature. By locating thermal paste in between the TEDs and sample holder and between the sample holder and the first temperature sensor, control over temperature and the speed at which a temperature is reached may be improved such that minimal cooling is required during a heating step and minimal heating is required during a cooling step.

When the setpoint temperature during either of a heating or cooling stage is reached, and it is desired to maintain such temperature for a period of time, it may be necessary to continue to deliver power, but in a lesser amount then previously. Thus, the methodology envisions the possibility of issuing one or more signals (e.g., by way of a modified Proportional Integral Derivative ("PID") control logic) to cause a reduction in the power to the thermal cycling elements. Pulse width modulation may be employed to control delivery of such power.

As noted previously, the teachings herein take into account a recognition that within thermocycler systems employing certain thermal cycling elements, such as TEDs, there arises the possibility for thermal inertia effects. That is, for samples that are processed in accordance with the present teachings, there will be a certain amount of mass that is subjected to heating and cooling. Such mass is generally passive, though it intrinsically conducts and stores a certain amount of heat. As a result, it is possible that a source or sink of heat that is delivered from the mass can be eliminated, and for a period of time, the mass will continue to conduct and store the heat that was delivered to it, and possibly see a rise or drop of its temperature. This heat storage, in the mass causes a dead time delay from the time of the change of the heat source or sink to the time when the temperature sensor can measure the change in the control. The dead time management of control operations to address such thermal inertia is an unexpected solution to problems heretofore faced as a result of temperature overshoots or undershoots.

The ability to manage such thermal inertia makes it possible to employ less overall power during an entire amplification process, to shorten individual heating and cooling operations, or both. In more detail, the step of receiving information (e.g., via signals) from one or more of the temperature sensors includes a step of transmitting a signal from one or more temperature sensors (e.g., an RTD temperature sensor, such as that employed for sensing the temperature of the sample holder). The information may be transmitted to the controller (e.g., an Arduino Mega2560 controller or the like). The processor of the controller may include a non-transitory storage medium that is programmed so that on a periodic basis (e.g., approximately less than every 1, 30 or even 150 milliseconds), temperature sensor signal input to the controller is identified and at least temporarily stored in memory. The length of such period may be selected to avoid unduly large lags in temperature readings. For example, an 8° C./sec ramp rate with 30 ms intervals gives ~0.24° C. temperature changes between readings. A 300 ms interval would give 2.4° C. temperature changes, which might cause temperatures to overshoot the desired temperature. The length of such period also is selected so that fast intervals avoid potential problems with overwhelming the processor with the processing of unnecessarily large amounts of data, which may be of relatively insignificant additional value as compared with data obtained from a slower period. The step of receiving information may be performed intermittently or continuously. For example, it may be ongoing, so it is up-to-date and ready to be sent as soon as the software asks for it.

In more particular detail, and without intending to be bound by theory, among the various aspects of the present teaching are the provisions herein that take into account and control operations to address thermal inertia effects that are present as a result of structure of various components. For example, the teachings take into account a recognition that performance may be enhanced by responding to dead times that may arise as between a heating or cooling operation and the temperature that is sensed as a result. That is, when temperature of a sample holder is changing quickly, such as at a rate of about 8 to 15° C./second heating or about 6 to 10° C./second cooling, then sensor lag time arises in the form of a delay from when the power to a thermal cycling instrument (e.g., at least one TED) is changed to when the thermal sensor begins to respond to that change. Believed to be among the contributing factors to this are the following: time for any circuit component (e.g., an H-bridge) to respond to a power change instruction from a control device; time for power to get to the thermal cycling elements (e.g., TEDs); time for any of the thermal cycling elements (e.g., TEDs) to respond to the power change; time for heat to be pumped to/from, the TEDs (if used) through any thermal paste and into the sample holder; time for the temperature change to conduct from the sample holder through the thermal paste to a temperature sensor carried on the sample holder; time for heat to conduct through the temperature sensor case to the actual sensor wires within the temperature sensor; time for the sensor wires to change temperature and thus give a changed temperature signal; time for the temperature signal to be amplified; time for the processor to measure the change in the amplified temperature signal; and time for that changed measurement to be communicated to the software.

During the dead time, it is likely that the temperature of each element within that system continually changes. By the time the software notices a temperature change of the sample holder, the sample holder may then be at a new temperature. To illustrate, suppose there is a 0.2 sec dead time from the sample holder temperature to the controlling software and the sample holder at a 15° C./sec ramp rate, then the software signal could lag the actual temperature by (15° C./sec)*(0.2 sec)=3.0° C. In other words, in that scenario, by the time the software thinks the temperature has reached the setpoint, then the actual temperature would have overshot the setpoint by 3.0° C. When PCR results can be impacted by temperature errors as great at 0.5° C., that 3.0° C. difference can be quite significant. Even if the software immediately changes the power signal to the TEDs, the dead time from the time the software sent the signal until the time the change reaches the sample holder, the inertia of past heating signals will have carried that sample holder even more than 3.0° C. past the desired temperature setpoint.

Accordingly, the teachings herein contemplate the reduction of dead time so that controlling operations commands (e.g., those issued by software on a non-transitory storage media), can apply braking to the heating or cooling operation before a setpoint temperature has been reached. Braking may be done as described herein, with one preferred approach being the reversal of polarity of at least one thermal cycling element (e.g., at least one TED) while heating to issue a pulsing of cooling, or vice versa, the reversal of polarity of at least one thermal cycling element (e.g., at least one TED) while cooling to issue a pulsing of heating. The polarity reversal effect occurs at a dynamically altered and calculated offset temperature value (which may be altered within one of more stages, within one or more cycles or both).

Another surprising aspect of the teachings herein is that the determination of the offset temperature may not merely be a function of sample holder temperature. It may also be a function of at least one other temperature measure from a position (e.g., within the instrument) that is remote from the sensor. For instance, one unique feature of the thermocycler is that an optimal TOFFSET temperature may be a function of the heat exchanger temperature as measured by a second sensor. Such heat exchanger temperature, in turn, may be influenced by such factors as the thermal paste employed, manufacturing variances or other factors that may influence inertia or lag.

It should be appreciated, that the "braking" operation need not be employed in every instance. In some instances, such as when the heating rate and anticipated dead time are sufficiently low, that a resulting temperature error of less than about 1° C. (or even about 0.25° C.) will occur, then braking may be avoided before entering a temperature hold. For example, it may be possible to simply identify a predetermined temperature (e.g., an offset temperature) and instead of polarity reversal, simply cease applying power to one or more thermal cycling element so that the sample holder arrives at a temperature within it through inertial effects.

The processor on the controller may include a non-transitory storage medium programmed to cause a processor or other computing device to substantially continuously sum up a predetermined amount of the most recent voltage data points from the one or more temperature sensors (e.g., the most recent 100, 600, 2000 or some other statistically reliable amount of RTD voltage data points that is sufficient to minimize random noise, but not too large that there is a long delay lag to measure real temperature changes). The controller may be programmed to give greater weight to more recent data points if desired to enhance accuracy. Conversely, the controller may be programmed to give greater weight to less recent data points or adjusted within the software to more closely match the temperature experienced within the internal of the sample tube.

The processor on the controller may include a non-transitory storage medium that is programmed to cause a processor or other computing device to provide a storable temperature value (T) that is a function of the substantially continuously summed up voltage data points. By way of example, a cubic formula may be applied for obtaining the temperature value (T). To illustrate, the a voltage signal summation from the controller may be stored as a software variable, V, and the temperature value determined according to a suitable calibration formula (1), which may be obtained empirically, such as by comparing the temperature of the RTD to the temperature measured with NIST-traceable calibration probes. An illustrative Formula (1) is, as follows:

$$T = V^3 * cubic + V^2 * quadratic + V * slope + V * intercept \quad \text{Formula (1):}$$

The Formula (1) may be adjusted for the summation, and/or any data point weighting, if used. Optionally, this temperature T may be estimated based upon a history of past temperature reads. Such estimation, based upon the slope of the temperature reads, may be appropriate in instances when a substantial period of time has elapsed since a temperature signal has been received.

As indicated, one possible methodology employs a step of processing the temperature sensor signal information to determine the appropriate power and voltage polarity to supply to at least one of the thermal cycling elements (e.g., TEDs) to cause heating or cooling by way of the thermal cycling elements. Such step may also include a step of determine whether to cause heating or cooling at full power, to use a modified Proportional Integral Derivative (PID) control logic to control heating or cooling or both. By way of illustration of this step, it is envisioned that in the course of an amplification process, there may be a series of repeated heating and cooling cycles (e.g., at least about 10, 20, 30 or more) that cause a nucleic acid (e.g., DNA) sample to be subjected to denaturation, annealing and elongation, until the copies of the desired nucleic acid segment (e.g., gene) are increased exponentially. Each switch between heating and cooling may be regarded as a temperature stage. At the start of every temperature stage, it is possible that there will be a step of determining if a temperature condition needs to be changed (e.g., via the thermal cycling elements) for the next stage. For this, a setpoint temperature (e.g., a temperature inputted by an operator, such as when the operator inputs the desired temperatures for the heating and cooling cycles) may be compared with the temperature (T) value obtained from one or more of the temperature sensors. If T differs from the next setpoint, Tsetpoint, by a certain predetermined value (e.g., less than 2° C., 1° C. or even about 0.25° C.), then it may be possible to skip the heating/cooling step. Optionally, it may be corrected if needed in the hold stage with a modified PIDlogic control operation. If T is colder by a certain predetermined value (e.g., at least 1° C. (or even about 0.25° C.) colder) than the next setpoint, then the controller may issue an appropriate signal (e.g., substantially immediately) to set the TEDs to a certain level of power (e.g., 100% of available power) for heating, so that the temperature can reach the setpoint temperature quickly. Similarly, if T is hotter by a certain predetermined value (e.g., at least 1° C. (or even about 0.25° C.) hotter) than the next setpoint, then the controller may issue an appropriate signal (e.g., substantially immediately) to set the TEDs to a certain level of power (e.g., 100% of available power) for cooling so that the temperature can reach the setpoint temperature quickly.

The methods herein may employ a step of stopping the application of power for heating or cooling prior to the temperature sensors signaling that the setpoint temperature has been reached. It is thus possible that the methods employed may avoid temperature overshoot conditions. Accordingly, the methods herein envision a step of determining one or more stopping times for the application of power (e.g., for stopping the application of 100% of available power) for heating or cooling.

The methods herein may also employ one or more steps of ceasing or otherwise altering power delivery to at least one of all of the thermal cycling elements. For example, the controller may cause cessation or alteration of power delivery upon the occurrence of one or more of receipt of a signal that an operator has inputted a command to stop or pause operation; detection that the operation of software has ceased; receipt of a signal that an internally programmed diagnostic test has been run and is not satisfied by the thermocycler (e.g., a diagnostic test may be performed that includes one or more tests for proper 12 V, 5 V, and ground line signals; checks of any heat sink and/or PCB temperature; temperature sensor response testing, (such as a test that confirms a signal response from a temperature sensor when a known heating or cooling function is performed)); or defection that a communication disruption has occurred between an operator computer processor and the thermocycler (e.g., if the computer processor locks up, a communication line becomes disconnected or otherwise. In any of these instances, heating or cooling may be caused to stop by a signal from the controller that turns off an H-bridge, which will also stop powering the thermal cycling elements (e.g., the TEDs).

During normal cycling in an amplification process, it is possible that the controller may cause cessation or other alteration of power delivery upon the occurrence of receipt of a signal indicating that the temperature setpoint has already been reached and/or passed. In one aspect, the software may provide a restricted mode function, which is activated if the heat exchangers begin, to approach a trip set-point of the thermostat which may eliminate power to the entire thermocycler. If a second temperature sensor on the heat sinks reaches a pre-defined setpoint (i.e. about 5 to 10 degrees below the thermostat setpoint range), the amount of available power that can be applied to the TEDs is reduced (i.e. from 100% to 80%). The restricted mode setpoint and percent power are configured such that the instrument may continue to execute the protocol under extremely adverse conditions without arriving at the trip set-point. The amount of power available for the TEDs upon the heat sinks reaching the setpoint temperature for the restricted mode may be adjustable or may be a fixed value.

In one preferred aspect, it is possible that the controller will operate to stop or otherwise alter power delivery for heating or cooling slightly before the temperature setpoint has been reached. Thus, the controller will operate to stop or alter power delivery when a signal is obtained that indicates that a temperature of the sample holder, heat exchanger or both have passed an offset temperature (TOFFSET) and entered within an offset temperature range (i.e., a temperature between the Toffset and Tsetpoint). In general, during a heating operation, the controller will cause cessation or other alteration of the power supply to the thermal cycling elements when the sensed temperature value (T) is greater than or equal to the value of Tsetpoint minus the value of Toffset. In general, during a cooling operation, the controller will cause cessation or other alteration of the power supply to the thermal cycling elements when the sensed temperature value (T) is less than or equal to the value of Tsetpoint plus the value of Toffset. For each of the heating and cooling operations, the value for Toffset differ, and may be empirically determined and may be continually updated within a heating or cooling operation. Typically it is a value that is at least about 7.5° C. from the Tsetpoint. The empirical determination of Toffset generally will contemplate considerations relating to temperature slope, temperature setpoint, and starting temperature. If the slope of the temperature (as a function of time) is positive and high, then the temperature at which the heating at high (e.g., 100%) power is stopped should occur sooner (larger offset). If the slope of the temperature is near zero, then the temperature at which the heating at 100% power is stopped should occur later (smaller-offset). If the slope of the temperature is negative during heating, then there may be a problem with the instrument, but if not, the temperature offset should be small or hear zero. In regard to the temperature setpoint consideration, if the temperature setpoint is high, then there is most likely a large temperature range that is being covered and the temperature will be subject to thermal inertia considerations of the heated mass, so the temperature at which the heating at 100% power is stopped should occur sooner (larger offset). If the temperature setpoint is low, then there is most likely a small temperature range that is being covered and the temperature will not have a lot of influence of thermal inertia, so the temperature at which the heating at 100% power is stopped should occur later (smaller offset). In regard to the starting temperature consideration, if the starting temperature is high, then there is most likely not much temperature ground to cover, so the temperature at which the heating at 100% power is stopped should occur sooner to avoid overshoots. If the starting temperature is low, then there is most likely a lot of ground that the temperature must cover, so the temperature at which the heating at 100% power is stopped should occur later to be certain to actually reach the setpoint.

By way of illustration, for heating operations, Toffset may be the lesser of 7.5° C. or a value empirically determined by a generally linear formula, namely that of Formula (2). Toffset is regularly updated during heating since the measured values of Tslope and Theatsink will change as the heating progresses. It should be appreciated that the empirical values employed below (and for the mother formulae herein) may be empirically determined for particular instruments and may vary (e.g., within about 10%, 20%, 30% or more of the recited values).

$$Toffset = (7.83016E\text{-}04*Tslope^2 + 0.2004083*Tslope - 0.000461*Tsetpoint + 0.0118805*Tstart + Rheat2*Theatsink + Rheat1 - 2.50484) \quad \text{Formula (2):}$$

For Formula (2), Tslope is the slope at which the temperature is rising and Tstart is the temperature when the heating phase is started. Rheat1 and Rheat2 are constants related to response capabilities of each machine, such that Rheat1=−0.00218199*AutoTime+1.457692 and Rheat2=0.00170697*AutoTime−0.0001742*Tsetpoint−0.08496. AutoTime is an empirically determined value for each instrument and may vary from instrument to instrument and is a factor that takes into account thermal inertia and/or lag effects. Generally, it will be a time in seconds to cycle to 95° C. then to 60° C. ten times with no holds, at each temperature, starting with heat exchanger temperature at 31° C. AutoTime typically may range from about 55 seconds to about 75 seconds, more typically about 64 seconds.

By way of illustration, for cooling operations, Toffset may be the lesser of 7.5° C. or the absolute value empirically determined by a quadratic formula, namely that of Formula (3). If there is a hold time of greater than 1 second, 0.25° C. is added to Toffset. Toffset is regularly updated during cooling since the measured values of Tslope and Theatsink will change as the cooling progresses.

$$Toffset = \text{absolute value of } [-0.006334*Tslope^2 - 0.0082697*Tslope - 0.01855*Tsetpoint + 0.0025557*Tstart + Rcool2*Theatsink + Rcool1 - 0.38227] \quad \text{Formula (3):}$$

If there is a hold time greater than one second, subtract 0.25° C. from Toffset. If the final Toffset is greater than 7.5° C., then Toffset=7.5° C. Rcool1 and Rcool2 are constants related to response capabilities of each machine, such that Rcool1=−0.00218199*AutoTime+1.457692 and Rcool2=0.00068584*AutoTime+0.0000813*Tsetpoint+0.026004.

Heating or cooling may be stopped without the temperature overshooting (e.g., heating hotter than the Tsetpoint for heating) or undershooting (e.g., cooling colder than the Tsetpoint for cooling). This may be accomplished by reversing the direction of polarity of the H-bridge output for a specified amount of time so that the thermal inertia is stopped substantially at the Tsetpoint, but leaving the power substantially constant (e.g., at 100%). The amount of time to apply reverse polarity direction (referred to as the "stopping time") may be controlled in accordance with at least two factors, namely the desired new setpoint and the temperature that is sensed from a second location (e.g., from a heat exchanger) that is remote from the first sensed location (e.g., the sample holder). By way of illustration, the times (in milliseconds (ms)) for which a reversed polarity direction voltage is applied (e.g., at 100% of available power) may be selected from the following Table 2. Times specified may vary within a range of about ±20%, or about ±10%. For the below, the determination of whether a heat exchanger is warm or cold can be based upon an actual temperature measurement. Alternatively, it could be regarded as cold if less than four heating operations and four cooling operations of an amplification process have occurred.

TABLE 2

| Setpoint temperature | Time (heat exchanger warm) | Time (heat exchanger cold) |
|---|---|---|
| >85° C. | 70 ms | 65 ms |
| 66° C. to 85° C. | 70 ms | 62 ms |

Faster times are also possible, e.g., less than about 50 ms, less than about 30 ms or even about 15 ms.

The teachings herein envision that at such time when external heating or cooling has stopped, and the thermal inertia of the heated mass is generally in an equilibrium temperature state at or near the setpoint temperature, the temperature of the heated mass (e.g., the sample holder) may be kept generally constant at or near the temperature setpoint for a certain predetermined set holding time. For this, the controller may include a non-transitory storage medium programmed to cause a processor or other computer device to employ a modified proportional integral derivative (PID) control logic to maintain the temperature, at substantially that setpoint for such set holding time (e.g., via pulse width modulation). If the set holding time is less than the stopping time (e.g., approximately 15 milliseconds), then it may be unnecessary to invoke the employment of employing PID logic, because the temperature has already been near the temperature setpoint for at least the period of that holding time. In such instance, it is possible that the controller will simply issue a signal to proceed with the next programmed heating or cooling operation (e.g., to continue at 100% of available power to attain the next predetermined temperature setpoint).

One approach to operating the thermocycler during any PID control step is for the controller to issue a signal to place any of the thermal cycling elements (e.g., the TEDs) in a heating operation (e.g., the controller commands a H-bridge circuit element so that polarity of voltage for the TEDs causes heating of the TEDs). The controller may cause power to be delivered in any suitable amount. One approach is to cause power to be delivered at one or more different amounts, such as by a gradual ramping (e.g., in percent from 0 to 100 in 256 discrete, steps with 0 representing 0% power and 100 representing 100% power), where power is determined according to Formula (4).

$$\text{Power} = (0.003426 * T\text{setpoint}^2 + 0.340975 * T\text{setpoint} - 0.95 * T\text{heatsink} + 0.5) - (T\text{error} * 17 + 0.00077 * T\text{integral} + 2.5 * T\text{slope}) \quad \text{Formula (4):}$$

Formula 4 provides power value in percent. If Power is greater than 100% then set Power to 100%. If Power is greater than safe mode percent when safe mode is on then set power to the safe mode percent. If Power is positive then set the H-bridge to heat the TEDs. Otherwise set the H-bridge to cool the TEDs and use the absolute value of Formula 4 to set the Power percentage. Power is regularly updated as the temperature hold occurs Theatsink, TempError, Tintegral and Tslope will vary with time.

For Formula (4) Terror=T−Tsetpoint, and Tintegral is the integral of the temperature errors (summation of errors) during this temperature hold after the stopping time has been reached.

If the machine is cold (e.g., less than 4 PCR cycles have been performed, or as determined by a sensed heat exchanger temperature), then an additional amount of power may be added, to the determined value (e.g., about 5 to about 25%, such as about 16%). In this manner, it will be possible to take info account that heat sinks, which are not very hot, will withdraw more heat from the samples.

For the above, it is possible that when holding at temperatures below room temperature, the polarity of power that is employed may be such that the thermal cycling elements (e.g., TEDs) are operated for cooling instead of heating.

It will be appreciated, from the above teachings, that among the various, aspects of the present teachings are methods, apparatus, software (which may be in the form of firmware) adapted for operating a thermocycler instrument (e.g., a thermocycler device employing opposing spaced apart thermoelectric devices as described in the present teachings) for amplification, by polymerase chain reaction. One or more of the methods may be computer-implemented and thus may be executed by at least one electronic processor having program code on it. Thus, in regard to the various aspects there is envisioned at least one non-transitory tangible computer readable medium on which is provided program instructions, whether as software, firmware or both, for controlling operation of the instrument such as by a processor or other computer device to execute one or more steps or otherwise perform the recited functions.

One of the advantageous features believed possible in accordance with the present teachings is the ability to perform relatively rapid thermal cycling operations. The teachings herein concerning the unique hardware is believed to contribute, at least in part, to the rapid performance of the instrument. The rapid performance also is believed possible due, at least in part, to the improved computer-implemented techniques described herein, pursuant to which substantially real time temperature condition information is employed and processed for delivering suitable power to rapidly heat and cool a sample over a number of predetermined cycles and optionally operate one or more, air mover. One of the unique benefits of the computer-implemented techniques is the ability to operate the instrument at relatively high power levels corresponding with at least 80% or more (e.g., 85% or more, or even 95% or more, such as about 100%) of the available power, during one or more (if not all) of the heating and codling stages. Time is saved not only by the ability to operate at such high power levels, but also by virtue of the substantial avoidance of overshoot conditions (that is, heating to a temperature above a user predetermined setpoint temperature), and/or the avoidance of undershoot conditions (that is, cooling to a temperature below a user predetermined setpoint temperature). Overshoot conditions can be substantially avoided by use of program code that functions to cause a substantial change of heating rate from at least one thermal cycling element (e.g., at least one thermoelectric device) when an offset temperature is reached; and undershoot conditions can be substantially avoided by use of program code that functions to cause a substantial change of cooling rate from at least one thermal cycling element (e.g., at least one thermoelectric device) when an offset temperature is reached. Conceptually, program code herein functions to apply braking to a heating or cooling operation when a predetermined offset temperature is reached, until a setpoint temperature is reached.

With further elaboration now concerning the previous teachings, as pertaining to control methods and software that is adapted to perform such methods. At least one non-transitory tangible computer readable medium may store a program causing at least one computer processor to execute process steps that may include a step of receiving information (e.g., an electrical signal, or some other input) about a first temperature corresponding with the temperature at least one sample holder of the instrument, and about a second temperature corresponding with a temperature external of the sample holder. Such temperature desirably corresponds to a temperature within the sample holder (e.g., at a location that experiences substantially the same heat state as a sample undergoing PCR). Based upon the information concerning the first temperature and the second temperature, the process steps may include a step of dynamically altering or otherwise controlling any of a plurality of parameters (e.g., power that is applied, pulse width, duty cycle, offset temperature, or the like) for automatically controlling operation of at least one thermal cycling element of the instrument. As appreciated for the above, and for other teachings herein referring to software, the at least one non-transitory tangible computer readable medium thus may store a program that includes code that causes a processor or other computer device to perform functions called for in the steps.

As mentioned, a user is provided with opportunities to custom design a PCR protocol. The user inputted values may be stored in suitable memory (e.g., stored in a database), from which the values may be received for processing in accordance with operational aspects of the software. Such values may be stored temporarily or permanently. Thus, the teachings herein envision at least one non-transitory tangible computer readable medium that stores a program that includes code for instructing input of protocol parameters (e.g., using a suitable input device and being in response to one or more prompts by way of a graphical user interface provided on one or more display device, such as described previously with respect to the illustrations of FIGS. 3 and 4), directing the input to a suitable non-transitory storage medium, thereafter retrieving the inputted protocol values, and instructing operation of the thermocycler instrument in accordance with the protocol values. As discussed previously, such preselected values may include one or more setpoint temperatures for heating and/or cooling; one or more hold times; one or more repeat cycle amounts; and identification information to correlate a sample with a particular protocol for the instrument, among others (see FIGS. 3A-3G). A user may be able to retrieve a previously inputted protocol for causing additional cycling to occur in accordance with the protocol. The code may function to address other user preferences as have been described previously (e.g., the selection of "favorites", previously run protocols, adding notes, etc.).

Accordingly, on at least one non-transitory tangible computer readable medium there may be code that causes the following steps to be performed (e.g., by a processor or other computing device): receiving at least one first setpoint temperature predetermined by a user, the at least one first setpoint temperature being a maximum temperature to which a sample is to be heated for polymerase chain reaction of at least one sample; receiving at least one second setpoint temperature predetermined by the user, the at least one second setpoint temperature being a minimum temperature to which a sample is to be cooled for annealing of the at least one sample; receiving at least one first hold time corresponding with an amount of time predetermined by the user during which the temperature of the sample holder is maintained generally at the at least one first setpoint temperature; receiving at least one second hold time corresponding with an amount of time predetermined by the user during which the temperature of the sample holder is maintained generally at the at least one second setpoint temperature.

On at least one non-transitory tangible computer readable medium herein there may be code that performs, the functions of transmitting operational instructions to control (e.g., by causing a processor or other computing device to control) the heating and/or cooling of a thermal cycling element (e.g., one or more thermoelectric devices), and optionally one or more blowers. For example, the code may cause one or more electrical signals to deliver power to the thermal cycling elements (e.g., one or more thermoelectric devices), and optionally one or more blowers for causing the thermal cycling element, the optional blower, or both to effectuate heat transfer to or from at least one sample.

On the at least one non-transitory tangible computer readable medium herein there may be code that performs the functions of causing performance of the steps of receiving temperature information from at least one and preferably at least two temperature sensors. At least one of the temperature sensors may be adapted to deliver information about the temperature of a sample (e.g., by providing temperature information from within a sample holder that is holding the sample). Based upon the temperature information, the code may perform the function (e.g., causing a processor or other computer device to issue) of issuing control signals for operating the thermal cycling elements, the air mover or both for effectuating heat transfer to or from at least one sample (e.g., by the thermal cycling elements, the air mover or both) until the one or more, setpoint temperatures are reached.

In one particular aspect, the code may be such that it causes steps of issuing signals for supplying power to at least one of the thermal cycling elements, the optional blower, or each, until information about the temperature of a sample holder (e.g., such as a temperature condition from within the sample holder that approximates of otherwise corresponds with sample temperature) received from the one or more temperature sensors indicates that the temperature of the sample holder is within a predetermined difference (e.g., within about 5° C., within about 3° C. or even within about 1° C.) relative to the setpoint value, but prior to any overshoot of the value. Thus, to illustrate, if a setpoint temperature for a maximum heating temperature is 80° C., then the code would function to cause power to be delivered to one or more thermal cycling elements until a temperature less than 80° C. is reached (e.g., about 75° C., 77° C. or 79° C.), but is not exceeded. Likewise, for example, if a setpoint temperature for a lowest cooling temperature is 60° C., then the code would function to cause power to be delivered to one or more thermal cycling elements until a temperature higher than 60° C. (e.g., about 65° C., 63° C. or 61° C.) is reached, but is not below such temperature. Suitable code may be such that it causes signals to issue for supplying power to at least one of the thermal cycling elements, the optional air mover, or each, to change the conditions to which the sample holder is subjected from a heating to a cooling state, or vice versa. For instance, during what would be regarded as a heating cycle, when temperature information about a sample (e.g., information about the temperature of the holder) indicates that the temperature is rising and approaching the setpoint temperature, but before the temperature reaches the setpoint temperature, the code may be such that it may cause one or, more thermal cycling elements to stop the application or power for heating, and switch to applying power for cooling instead (e.g., for thermoelectric cycling elements, this may entail a reversal of polarity of the device and power delivery to the device in the reversed state) such that the temperature associated with the sample substantially reaches such setpoint temperature (e.g., it is within 1° C., or oven 0.25° C. of the setpoint temperature). The codes may be such that it causes some other braking operation to occur in lieu of, or in addition to polarity reversal.

As alluded to in the above, without intending to detract from the significance of the teachings herein, but for purposes of demonstrating the conceptual operation of the heating and cooling methodologies, the teachings herein may be understood conceptually as applying braking to a sample holder heating and cooling operation. For instance, during a heating step in which temperature is rising at a certain rate, when the temperature hears but is below the heating setpoint temperature, a pulsation (e.g., over the course of a relatively brief interval, such as an amount of less than about 1 second, less than about 700 milliseconds, less than about 500 milliseconds of even less than about 100 milliseconds (e.g., about 70, 50, 30 or even 15 milliseconds (ms) or less)) of cooling is applied to slow the rate, of heating of the sample holder, i.e., braking of the heating of the sample holder occurs. In this manner it may be possible that the methods are performed to avoid overshoot of the setpoint temperature. Though an amount of cooling occurs, the heat delivered during the heating, step may continue to propagate throughout the sample holder, albeit at a slower rate than prior to the pulsation. Similarly, during a cooling step in which temperature is dropping at a certain rate, when the temperature nears put is below the codling setpoint temperature, a pulsation (e.g., over the course of a relatively brief interval, such as an amount of less than about 1 second, less than about 500 milliseconds or even less than about 100 milliseconds (e.g., about 15 milliseconds) of heating is applied to slow the rate of cooling, i.e., braking of the cooling occurs. Though an amount of heating occurs, the heat removal during the cooling continues throughout the sample holder, albeit at a slower rate than prior to the pulsation. In this manner it may be possible that, the methods are performed to avoid undershoot of the setpoint temperature for cooling.

Though conceptually the operations are possible with a single sensor within a sample holder, advantageously a second sensor is employed, and preferably is located remotely from the sample holder. As it pertains to the methods, apparatus and software herein, the temperature at which the reversal occurs from heating to cooling (i.e., the temperature at which a cooling pulsation starts), or from cooling to heating (i.e., the temperature at which a heating pulsation starts), or at which some other braking operation occurs, may be regarded as an offset temperature ("TOFFSET"). With reference to the above illustrative teachings, the offset temperature effectively is the temperature at which braking of heating or cooling commences (such as by way of reversed polarity direction of voltage to thermoelectric thermal cycling elements). In this manner, the fastest arrival at the setpoint destination is achieved.

Though it is possible that the offset temperature may be established as constant throughout thermal cycling of a sample, the offset temperature may vary throughout the thermal cycling of a sample. Thus, from heating stage to heating stage, or from cooling stage to cooling stage, or within a heating or cooling stage, respective stage offset temperatures may differ. The offset temperature may vary to address a substantially instantaneous temperature condition measured (e.g., by at least one and more preferably at least two spaced apart temperature sensors) for a sample. Thus the teachings herein contemplate that there may be at least one non-transitory, tangible computer readable medium herein having code thereon that causes steps of receiving information (e.g., by way of one or more signals from at least one, and preferably two or more temperature sensors) about a substantially instantaneous temperature condition to which a sample is being subjected, calculating an offset temperature to address the substantially instantaneous temperature condition, and based upon the calculated value, issuing instructions for causing at least one pulsation of cooling (if during a sample heating step) or at least one pulsation of cooling (if during a sample cooling step).

It will be appreciated, in view of the context of the teachings herein, that any instructions for causing a thermal cycling element to heat or cool, of for causing a pulsation of heating or cooling, may entail causing electrical power to be delivered to one or more thermal cycling elements, in one or more predetermined amounts for one or more predetermined amounts of time. With respect to embodiments herein employing thermoelectric devices, such steps may entail causing polarity of any thermoelectric devices to be switched between heating and cooling modes of operation. Code for causing these functions to be performed may be a part of any computer program that is stored on at least one non-transitory tangible computer readable medium. It should be appreciated that additional modes of operation are also envisioned. For example, it is described that the methods herein may include switching from heating to cooling (i.e., a pulsation) within a heating cycle, and switching from cooling to heating (i.e., a heating pulsation) within a cooling cycle. Such an approach, particularly when employed with a thermoelectric device as a thermal cycling element that does both the heating and the cooling, advantageously allows the thermal cycling element to be operated to its rated power capacity (or a predetermined fraction thereof). It is also possible that, rather than switching from heating to cooling within a heating step (or cooling to heating within a heating step), that power delivered to the thermal cycling element may be substantially reduced (e.g., by 50% or more of its highest volume) or ceased to slow the rate of heating or cooling upon reaching an offset temperature within a sample holder. Another possibility may be to employ multiple thermal cycling elements. For example, one thermal cycling element may be employed as a primary heating or cooling element and an auxiliary thermal cycling element is employed for the pulsation. In this manner, the teachings herein envision that when an offset temperature is reached the primary thermal cycling element is operated in a heating or cooling mode, with the auxiliary element operated in the respective opposite cooling or heating mode.

With additional discussion now about the previously discussed offset temperature, the offset temperature may be a dynamic value that fluctuates throughout the thermal cycling of a sample. It may be a value that is calculated by one or more algorithms based upon temperature readings from either or both of the temperature sensors that occurs during a stage of heating and/or codling. The offset temperature may be a function of the initial starting temperature at the start of a respective heating or cooling stage, the user's predetermined setpoint temperature, and the temperatures measured by the temperature sensors (e.g., a first temperature sensor located within the sample holder and a second temperature sensors located remotely from the sample holder). The offset temperature may be a dynamic calculated value that is repeatedly determined by a formula that includes as a portion a linear function of the second temperature signal. The formula can include a portion that is a quadratic function of the slope of the first temperature signal with respect to time. The formula can be a linear function of the users' predetermined setpoint temperature. The formula can be a linear function of the initial starting temperature. The formula may be such that is can be derived by recording overshoots and undershoots as a function of the second temperature signal, the startpoints, setpoints, etc., and then empirically evaluating the values by linear regression analysis.

In another unique aspect of the teachings herein, as described elsewhere, at least one second temperature sensor is employed, which will be remotely ideated relative to the first temperature sensor. For example, it may be external of the sample holder, such as on a heat exchanger associated with one or more of the thermal cycling elements. The software herein is contemplated to receive information from the second sensor and perform one or more calculations based upon such information.

In more detail, it is thus contemplated that there may be steps performed that dynamically alter power delivery and which may be computer implemented. For example, at least one non-transitory storage medium may have a program with code that has instructions for causing at least one thermal cycling element to heat a sample holder; receiving a first sensor signal from a first temperature sensor corresponding with a temperature of the sample holder; receiving a second sensor signal from at least one second temperature sensor that is located externally of the sample holder (e.g., on or near a heat exchanger); determining a value of any first temperature offset amount (TOFFSET1) based upon the temperature reading from the at least one first and second temperature sensors; causing heating of the sample holder until the sample holder reaches a first offset temperature that is below the first setpoint temperature by the first temperature offset amount; at the time when the first offset temperature is reached, causing a cooling pulsation of the at least one thermal, cycling element during the heating stage for a sufficient amount of time so that the temperature arrives within about 1° C. (or even about 0.25° C.) of the first setpoint temperature and further heating of the sample holder is substantially interrupted; causing the temperature to be maintained within about 1° C. (or even about 0.25° C.) of the first setpoint temperature for the first hold time; causing at least one thermal cycling element to cool a sample holder until the temperature of the sample holder reaches a second offset temperature that is above the second setpoint temperature by a second temperature offset (TOFFSET2) amount; receiving a signal from the first temperature sensor corresponding with a temperature of the sample holder; receiving a temperature reading from the at least one second temperature sensor that is locate remotely from the sample holder; determining a value of any second temperature offset amount (TOFFSET2) based upon the temperature reading from the at least one first and second temperature sensors; causing cooling of the sample holder until the sample holder reaches a second offset temperature that is above the second setpoint temperature by the second temperature offset amount; at the time when the second offset temperature is reached, causing a heating pulsation of the at least one thermal cycling element during the cooling stage for a sufficient amount of time so that the temperature arrives within about 1° C. (or even about 0.25° C.) of the second setpoint temperature and further cooling of the sample holder is interrupted; and causing the temperature to be maintained within about 1° C. (or even about 0.25° C.) of the second setpoint temperature for the second hold time.

As indicated one or more algorithms may be employed for determining the offset temperatures. With reference to the above embodiments, illustrative algorithms may include, the following. For example, it is envisioned that code may be provided (by way of a non-transitory computer storage medium) that has instructions for deriving a value of a first offset amount based upon the temperature reading from the at least one second temperature sensor according to the previously discussed Formula (2):

$$T\text{offset} = (7.83016E{-}04 * T\text{slope}^2 + 0.2004083 * T\text{slope} - 0.000461 * T\text{setpoint} + 0.0118805 * T\text{start} + R\text{heat2} * T\text{heatsink} + R\text{heat1} - 2.50484)$$

Pursuant to Formula 2, Tslope is the instantaneous slope at which the temperature of the sample holder is rising and Tstart is the temperature of the sample holder when the heating of step (e) started; Rheat1=−0.00218199*AutoTime+1.457692 and Rheat2=0.00170697*AutoTime−0.0001742*Tsetpoint−0.08496; and AutoTime ranges from about 55 seconds to about 75 seconds.

It is envisioned that code may be provided (by way of a non-transitory computer storage medium) that has instructions for deriving a value of a second offset amount based upon the temperature reading from the at least one/second temperature sensor according to the following previously discussed Formula (3):

$$T\text{offset} = \text{absolute value of } [-0.006334 * T\text{slope}^2 - 0.0082697 * T\text{slope} - 0.01855 * T\text{setpoint} + 0.0025557 * T\text{start} + R\text{cool2} * T\text{heatsink} + R\text{cool1} - 0.38227]$$

Pursuant to Formula 3, if there is a hold time greater than one second, then 0.25° C. is subtracted from Toffset; If the final Toffset is greater than 7.5° C., then Toffset=7.5° C.; Rcool1=−0.00218199*AutoTime+1.457692 and Rcool2=0.00068584*AutoTime+0.0000813*Tsetpoint+0.026004.

It will be appreciated that, after any the pulsation period has passed, the sample holder temperature may be held at or near the setpoint temperature for a hold time as set by a predetermined-value from the user. If the hold time is set to zero seconds, then there is no temperature hold, and the software goes on to the next temperature setpoint. To perform the temperature hold, at least one non-transitory storage medium may be employed that includes code for causing power and polarity of the thermal cycling elements (e.g., TEDs) to be repeatedly updated with the goal, to maintain the sample holder at a temperature that is within 1° C. or even 0.25° C. of the setpoint temperature. This may be accomplished by causing a step of (a) pulse width modulation to alter the power sent to the TEDs and/or through (b) changing the polarity, as necessary. A pulse width modulation percent ranging from −100% to 100% may be calculated, where negative percent values designate cooling by the TEDs and positive percent values designate heating by the TEDs. The pulse width modulation percent may be a modified form of PID (proportional, integral, and derivative) control of the first temperature sensor. The modified PID formula has additional, terms which depend on the setpoint temperature and the second temperature sensor value. Meanwhile the code may cause operation for a period of time and may interface with a timer so that the temperature hold begins as soon as the sample holder temperature is within ±1° C. of the setpoint temperature. The temperature hold timer may start during the pulsation period. After the temperature hold time has passed, then the software will advance sequence of operations so that it causes heating or cooling in a successive stage (e.g., to the next successive temperature setpoint in the user inputted protocol).

As can be appreciated, PCR amplification will typically require that a plurality of cycles to be performed. Thus, the at least one non-transitory tangible computer readable medium herein may further include code that causes a repetition of the above steps for a predetermined number of cycles until the amplification desired by the user is achieved. By way of example, without limitation, the teachings herein contemplate that the code may include instructions that cause the instrument to perform the function of receiving at least one first setpoint temperature of at least about 85° C., to which at least one sample is to be heated in a sample holder for polymerase chain reaction denaturation, and at least one second setpoint temperature of below about 70° C. to which the sample held in the sample holder is to be cooled for annealing of the at least one sample. The code may include instructions that cause the instrument to perform the function of maintaining a heating rate of at least about 8° C./second (e.g., at least 10° C./sec, at least 12° C./sec or 15° C./sec) until a first offset temperature amount below (by no more than about 7.5° C. below) the first setpoint temperature is reached for the sample holder. The code may include instructions that cause the instrument to perform the function of, when the first offset, temperature is reached, pulse cooling the sample holder to slow the heating rate until the sample holder is within about 1° C. of the first setpoint temperature. The code may include instructions that cause the instrument to perform the function of maintaining a cooling rate of 6° C./second, 8° C./second, or 10° C./second until a second offset temperature above (by no more than about 7.5° C. above) the second setpoint temperature is reached for the sample holder. The code may include instructions that cause the instrument to perform the function of, when the second offset temperature is reached, pulse heating the sample holder to slow the cooling rate until the sample holder is within about 1° C. of the second setpoint temperature. The code may include instructions that cause the instrument to perform the function of receiving information from a sensor arrangement for monitoring a first temperature corresponding with a temperature of the sample holder and a second temperature corresponding with a temperature external of the sample holder. The code may include instructions that cause the instrument to perform the function of adjusting the time, temperature or both at which the steps of pulse cooling, the pulse heating or both commence based upon the first temperature and the second temperature. The code may include instructions that cause the instrument to repeat the above steps for a predetermined number of cycles (e.g., using a cycle number value inputted by a user) until the amplification desired by the user is achieved.

From the above, it will be understood that offset temperatures may be calculated one or more times within a particular stage, within a particular cycle or within a complete PCR amplification operation. The teachings thus envision a closed loop control operation, which employs temperature readings from each of two or more sensors provided to address thermal inertia indicators, and performs calculations to continually or at least periodically update an offset temperature value that is used to determine the time when a pulsing function is performed (e.g., a cooling pulse during a heating stage, or a heating pulse during a cooling stage).

The teachings herein contemplate that software may be programmed (e.g., as firmware) in at least one microprocessor physically located on board the instrument. Moreover, software may be employed on an electronic microprocessor, that is either on board or separate from the instrument (e.g., as part of a dedicated computer for this purpose or some other computer, such as a computer server, a desktop computer, a notebook computer, a netbook computer, a tablet, a smartphone, or some other device). The firmware and the software may cooperate together for causing the operation of the instrument. The software effectively operates in a master/slave relation with the firmware and issues commands to the firmware.

By way of illustration, as to any such firmware, it is thus contemplated that the instrument may include at least one non-transitory tangible computer readable medium herein, which may further include code that is programmed for causing to be performed the functions of initializing the operation of the instrument (e.g., causing power to initially be delivered to one or more of the thermal cycling elements); establishing communication with the software (e.g., via a USB connection); receiving temperature sensor information and determining substantially in real-time a moving average of temperature received from the sensors (e.g., so that such sensor information can be inputted into the software); monitoring activity of communication with the electronic microprocessor on which the software resides, and (a) if communication has lapsed for a pertain period, re-establishing communication, and/or (b) if there has been a predetermined period in which commands from the computer have not been received, then providing an update to the computer of temperature sensor information; and performing commands received from the software (e.g., measure and report diagnostics, measure and report temperatures, adjust power to the thermal cycling elements, control power to any blower, enable or disable any circuitry of the instrument, read and/or write calibration and/or data to memory, and/or reset communications with the computer on which the software resides). The firmware may also include code that is programmed for performing the function of diagnosing instrument faults and reporting such faults.

To further illustrate the above teachings, reference may be made to FIGS. 5A-5F. FIG. 5A illustrates examples of sequences of steps that firmware may perform. Thus, for the firmware, at least one non-transitory tangible computer readable medium may be programmed with code for issuing instructions to the instrument of the teachings to perform one or any combination of the following steps. There may be a step of initializing the thermocycler instrument (step 5a1). There may be a step of establishing communications with an electronic processor having the instrument software thereon (e.g., via a suitable communication link, which may be wireless, wired (and thus which may include a suitable connection such as a USB connection), or both)) (step 5a2). There may be a step of updating a moving average of temperatures measured by one or more of the instrument temperature sensors (step 5a3). There may be a step of determining if communication is still active (e.g., via the communication link) between the firmware and the instrument software (step 5a4). There may be a step of determining if there are any commands issuing from the electronic processor upon which the instrument software code resides (step 5a5). There may be a step of performing one or more of the operational commands that are instructed and communicated via the communications link from the instrument software (step 5a6). Thus, instructions from the instrument software may cause the firmware to cause performance of one or more functions such as measuring and/or reporting instrument diagnostics; measuring and/or reporting sensed temperatures; adjusting power and/or polarity of one or more of the thermal cycling elements (e.g., thermoelectric devices or TEDs); enabling or disabling one or more circuit elements (e.g., an H-bridge); controlling power delivered to one or more instrument blowers or fans; reading and/or writing calibration and/or data to memory; re-establishing or re-setting communications with the electronic processor having the instrument software thereon; and re-booting the instrument software. The firmware may operate according to the sequence of FIG. 5A, and may re-perform certain steps (e.g., steps 5a2 and 5a3) in response to a negative indication from steps 5a4 and 5a5, respectively.

With reference to FIG. 5B, there is shown a flow diagram for the general operation of the instrument software. Thus, at least one non-transitory tangible computer readable medium may be programmed with code for issuing instructions to the instrument of the teachings to perform one or any combination of the following steps. Upon a step of initializing the software 5b1, a step 5b2 of establishing a communication link with the firmware may be employed (e.g., via a USB connection, or otherwise as described previously). A step may be employed of setting up and initiating one or more background timers (step 5b3), pursuant to which one or more timing operations may be performed. For example, the one or more background timers (which will typically be running throughout instrument operation) may be such that after a predetermined amount of time has elapsed, the instrument software will issue one or more signals to interrogate the firmware to obtain information about any sensed temperature conditions, any instrument diagnostic issues or both (step 5b4) to determine if signaling communication with the firmware is still active (step 5b5). These periodic interrogations will continue at intervals established by step 5b3. However, if it is determined that communication with the firmware has been lost, then the software will cause to issue a signal independently of the firmware to cause the operation of the instrument to be interrupted (step 5b6), while continuing to seek to establish communications with the firmware (step 5b2). Steps 5b2-5b6 may occur concurrently with subsequent steps, e.g. the code may be such that the steps 5b2-5b6 may occur concurrently with operation of the software in the steps of FIG. 5C.

FIG. 5C illustrates the general functionality that is programmed in code stored on a non-transitory tangible computer readable medium for instructing instrument operation based upon whether the instrument is in an initial cycling mode for a sample, or whether the instrument is in a mode, in which its operation has been interrupted or otherwise stopped prematurely, before complete polymerase chain reaction (PCR) has occurred for a sample. In this mode, the software may be programmed to cause initializing steps or the other steps from FIG. 5B to occur (step 5c1), which may be ongoing. It will be appreciated that the computer or other electronic processor on which the code having the program instructions resides may be in signaling communication with a non-transitory tangible computer readable medium having a database or otherwise contains protocol information for PCR that has been inputted by a user, and the software will cause the function of retrieving such protocol information (step 5c2). Upon the code determining that there has been actuation by the user of the instrument (e.g., by depressing or clicking on a start button) (step 5c3), and upon determination that there has been no premature interruption of the protocol of an existing PCR operation (step 5c4) the code will cause the software and hardware to be initialized for commencement of cycling (step 5c5), which may entail re-setting values to initial values, clearing of information that is displayed to a user, and/or enabling power to be delivered to one or more thermal cycling elements (e.g., by activating a circuit device such as an integrated circuit that allows power to flow through the one or more thermoelectric elements). As seen from step 5c4, if a PCR operation was interrupted prematurely, the code may cause a step to be performed of determining the stage at which operation was interrupted and then re-starting operation an intermediate stage of operation (e.g., the stage at which the operation was interrupted). Thereafter, the PCR operation will progress with the first or next successive stage, as the case may be (step 5c6). Within each stage, it will be seen that the instrument software includes code for issuing instructions to cause heating or cooling to the desired temperature for the desired amount of time, and to repeat this until the desired number of cycles or cycling loops (i.e., a series of consecutive stages that include heating and any holding at a setpoint temperature) have occurred. Thus, the code will include instructions for causing to be performed the steps of commanding the instrument to heat or cool to a user inputted setpoint temperature for the particular stage (step 5c7); commanding the instrument hold at a setpoint temperature for the particular stage for a user inputted desired time (step 5c8); determining if the stage is at an end of a cycling loop (step 5c9), and if so, determining if the user-inputted number of loops have been completed (step 5c10). If the number of loops has been completed then, the next PCR stage can be performed. If not, then a loop count is incremented (step 5c11) and the next PCR stage is set to the beginning of a PCR loop (step 5c12), and the method continues until it is determined that the last user inputted stage of PCR occurs (step 5c13), at which time cycling is stopped (step 5c14), unless and until further cycling is desired by the user.

During the steps of heating or cooling to a user inputted setpoint temperature, consistent with the above step 5c7, it is envisioned that a heating or cooling routine may be initiated, such as previously described (with reference to the description of the "braking" of a heating or cooling operation). An illustration of such a heating or cooling routine is set forth in FIG. 5D. It is contemplated that the heating or cooling routine may be performed in accordance with instructions issued by in code stored on a non-transitory tangible computer readable medium for instructing instrument operation. By way of illustration, a step of initiating the heating or cooling routine may be performed (step 5d1), pursuant to which the code causes a value to be obtained for a user inputted stage, setpoint temperature (step 5d2) and a sample holder temperature measurement value (step 5d3). The code causes a comparison to be made between the setpoint value and the measured value and depending upon the results of the comparison (e.g., if a temperature difference is within a predetermined amount, such as about 2° C.) (step 5d4), will either cause an exiting from the routine (step 5d5), or establish instructions to cause either heating or cooling (step 5d6), and further determine the extent of power to be employed for the heating or cooling (which may range in amounts of the available power, but desirably will be at least about 75% of the available power, or even about 100% of the available power) (step 5d7). Additionally, the code may determine one or more control parameters for dictating the time for which power is applied, such as described previously (e.g., without limitation the amount of the power, any pulse width modulation or any combination thereof). For example, as seen for step 5d8, desirably an offset temperature will be determined as described previously, which may be calculated by an algorithm stored on the non-transitory tangible computer readable medium as part of the code. During the heating or cooling, the code will cause calculations to be performed on the basis of ongoing information obtained about the temperature of the sample holder (step 5d9) and the temperature from a location remote from the sample holder (which location may or may not be in thermal conducting relation with the sample holder). For example, the remote location may be part of a heat exchanger (e.g., heat sink) in thermal communication with the sample block, via an intermediate thermoelectric device, calculations will be made to determine the proximity of the temperature of the sample, holder to the setpoint temperature (step 5d10) and to determine a substantially instantaneous value for the offset temperature. If it is determined that the absolute value of any difference between an instantaneous temperature reading of the sample holder (Tcurrent) and setpoint temperature (Tsetpoint) is greater than the offset temperature (per step 5d10), then the code will cause a calculation to be made to determine whether braking of the heating or cooling (e.g., by switching polarity of one or more powered TED thermal cycling elements) should occur. This may be done by calculating the temperature slope (step 5d11). For example, if the temperature slope is greater than a predetermined value (e.g., 1° C./second), then the code may issue instructions to cause "braking" of the heating or cooling operation, such as by reversing polarity ("swapping directions") of a TED thermal cycling element, while operating the element at a predetermined power amount (e.g., 100% of available power) (step 5d12), so that a pulsing occurs as described previously. Of course, if the temperature slope is below the predetermined value, then such pulsing may not be heeded (step 5d13), and the routine may be exited for the stage. Meanwhile, temperature reading optionally may be caused to be displayed to the user (step 5d14). Throughout, as mentioned, the code may be obtaining ongoing information about the temperature remote from the sample holder (step 5d15), and using that information for performing calculations to update the offset temperature values (step 5d16).

With reference to FIG. 5E, the teachings herein also envision at least one non-transitory tangible computer readable medium may be programmed with code for issuing instructions to the instrument of the teachings to perform a temperature hold ("T hold"). This may arise, for example, in instances when a user desires and inputs into the system (for use by the instrument software) a protocol by which a sample is to be subjected to a substantially constant temperature for a specified time. The code may cause a temperature hold routine to be initiated (step 5e1), pursuant to which the inputted setpoint temperature may be obtained along with the desired hold time (step 5e2). If it is determined that no hold time has been entered or a hold time of zero has been entered (step 5e3), then the routine may be exited (step 5e4). If a hold time has been specified, then the code will determine operational parameters (e.g., polarity, power, time, any pulse width modulation, or otherwise for controlling operation of one or more of the thermal cycling elements) and command the instrument (e.g., via the firmware) to heat or cool according to the parameters (step 5e5). A starting time will be obtained for when the hold is to occur (step 5e6). Optionally, the code may cause temperatures to be displayed to a user (step 5e7). Desirably, throughout the routine (e.g., substantially continuously), temperature readings from sensors located in the sample holder, and remotely of the sample holder (e.g., on a heat exchanger, as described previously), may be obtained (step 5e8) and employed to determine whether to continue with the existing control parameters or to vary one or more parameter (step 5e9). For example, one approach may be for the code to issue instructions for modulating the pulse width of the power that is being delivered (effectively increasing or decreasing the power delivered to one or more of the TEDs) in order to maintain temperature substantially constant (step 5e10). This can continue for the time period selected by the user (the "setpoint time") (step 5e11), after which the routine can be exited (step 5e12).

FIG. 5F illustrates an example of one series of operations that may be computer-implemented such as by being instructed by code stored one at least one non-transitory storage, medium. The code may be such that it causes to be performed a step (step 5/1) of receiving at least one first setpoint temperature predetermined by a user. The at least one first setpoint temperature may be one or more maximum temperatures to which a sample is to be heated for a polymerase chain reaction (e.g., denaturation and/or elongation) of at least one sample. The code may cause a step (step 5/2) of receiving at least one second setpoint temperature predetermined by the user, the at least one second setpoint temperature being a minimum temperature to which a sample is to be cooled for annealing of the at least one sample. The code may cause a step (step 5/3) of receiving at least one first hold time corresponding with an amount of time predetermined by the user during which the temperature of the sample holder is maintained generally at the at least one first setpoint temperature, the code may cause a step (step 5/4) of receiving at least one second hold time corresponding with an amount of time predetermined by the user during which the temperature of the sample holder is maintained generally at the at least one second setpoint temperature, the above receiving steps may be in any sequence, the code may cause a step (step 5/5) of causing at least one thermal cycling element to heat a sample holder (e.g., in accordance with a heating routine as described previously). As may be appreciated, the code may be adapted for correlating signals corresponding with temperatures into information that may be employed as part of an algorithm for calculating one or more values that are used for establishing temperatures to which a sample is heated or cooled. The code may cause a step (step 5/6) of receiving information (e.g., by way of a first sensor signal) from a first temperature sensor corresponding with a temperature of the sample holder and a step (step 5/7) of receiving information (e.g., by way of at least one) from a second sensor signal from at least one second temperature sensor that is located externally of the sample holder (e.g., at a heat exchanger as described herein). The code may cause a calculation step (step 5/8) to be performed for determining a value of any first temperature offset amount (TOFFSET1), or some other trigger condition for activating a control operation, based upon the temperature reading from the at least one first and second temperature sensors. The code may include program instructions for causing a step (step 5/9) of heating, of the sample holder as needed until the sample holder reaches a first offset temperature that is below the first setpoint temperature by the first temperature offset amount. The code may cause steps 5/6 through 5/9 to repeat and continually update TOFFSET1 within a single stage until the offset temperature is reached. Moreover, the code may include program instructions for causing a step, (step 5/10), at the time the first offset temperature is reached, of starting a cooling pulsation of the at least one thermal cycling element during the heating stage for a sufficient amount of time so that the temperature arrives within a predetermined amount (e.g., about 1° C. or less, such as about 0.25° C.) of the first setpoint temperature and further heating of the sample holder is interrupted. The code may include program instructions for causing a step (step 5/11) of causing the temperature to be maintained within the predetermined amount (e.g., about 1° C. or less, such as about 0.25° C.) of the first setpoint temperature for the first hold time. The code may include program instructions for a step (step 5/12) of causing at (east one thermal cycling element to cool a sample holder. The code may be adapted for performing a step (step 5/13) of receiving information (e.g., by way of at least one signal) from the first temperature sensor corresponding with a temperature of the sample holder, and a step (step 5/14) of receiving temperature reading information (e.g., by way of at least one signal) from the at least one second temperature sensor that is located remotely from the sample holder. The code may cause a calculation step (step 5/15) to be performed for determining a value of any second temperature offset amount (TOFFSET2) (or some other trigger condition for activating a control operation) based upon temperature readings from the at least one first and second temperature sensors. The code may include program instructions for causing a step (step 5/16) of causing cooling as needed of the sample holder until the sample holder reaches a second, offset temperature that is above the second setpoint temperature by the second temperature offset amount (optionally by repeating steps 5/13 through 5/16 and continually updating TOFFSET2). The code may further issue instructions so that, at the time when the second offset temperature is reached, a step (step 5/17) is performed for causing a heating pulsation of the at least one thermal cycling element during the cooling stage for a sufficient amount of time so that the temperature arrives within a predetermined amount (e.g., about 1° C. or less, such as about 0.25° C.) of the second setpoint temperature and further cooling of the sample holder is interrupted. Moreover, the code may be that it causes a step (step 5c18) of causing the temperature to be maintained within the predetermined amount (e.g., about 1° C. or less, such as about 0.25° C.) of the second setpoint temperature for the second hold time. For example, it may cause a routine as described previously for temperature holds to occur. Of course, the code may be such that it causes a monitoring of the stages that have occurred within the user inputted protocol and will cause repeating of steps (step 5/19) for a predetermined number of cycles until the amplification desired by the user is achieved. The dotted paths of FIG. 5F optionally may be followed if multiple first setpoints exist and/or multiple second setpoints exist, for example, using the next successfully inputted setpoint and other protocol values. It will be appreciated that, if the first stage (as inputted by the user) requires cooling, then the code may go from step 5/4 to 5/10 (path not shown).

Reference to FIG. 6 provides additional guidance to the concepts of offset temperature and how it relates to a heating and cooling stage. Times and temperatures are shown for purposes of illustration. Shorter times for pulsation, for instance, are contemplated. For the illustration in FIG. 6, a heating stage heating starts at a first temperature (about 72° C.) and continues for a first amount of time (shown here as just, less than two seconds) to a first offset temperature (shown as about 93° C.). At that time, a cooling pulsation slows the cooling so that a sample holder arrives at a first setpoint temperature (shown as about 95° C., at right about two seconds). The sample holder is held at the first setpoint temperature (shown as about 95° C.) for first hold time (shown as about 5 seconds) (e.g., by pulse width modulation and multiple switching of polarity for both heating and cooling). A cooling stage then starts and cools from the first setpoint temperature to the second offset temperature (shown as about 62° C.), at which a heating pulsation occurs (shown as slightly less than one second, and may be about 15 milliseconds), until arriving at the second setpoint temperature. The sample holder is held at the second setpoint temperature (shown as about 60° C.) for second hold time (shown as about 6 seconds) (e.g., by pulse width modulation and multiple switching of polarity for both heating and cooling). As seen, the temperatures do not exceed 1° C. (or less, such as about 0.25° C.) from the setpoint temperatures, so that undershoot and overshoot are substantially minimized.

Though many of the teachings herein are described with reference to code performing a step or causing a step or function to be performed, the teachings contemplate that the code contains elements adapted for performing such step or function, even if not expressly stated. Thus, not only is the method enabled by the code contemplated within the scope of the teachings, but so is the code and its respective elements. Moreover, it will be appreciated that the various references to code stored on a non-transitory tangible computer readable medium, or other like clauses contemplate non-transitory embodiments and are not intended as covering transitory propagating signals. As to the steps for which the software is described as performing or causing to be performed, the teachings herein contemplate such steps whether associated with software or not. Thus, methods herein may include the steps described in the context of the software, whether executed by software of not.

The person skilled in the art will also understand that functions performed by software herein may be performed by firmware, and functions performed by firmware may be performed by software. The computer-implemented methods herein may be performed by at least one suitable electronic device and may be performed by a device including at least suitable electronic processor (e.g., one or more central processing units (CPUs) that performs various processing according to one or more programs recorded in a read only memory media (ROM), one or more programs loaded to random access memory media (RAM) or any combination thereof. Suitable storage media (e.g., RAM) may store data inputted by a user, by way of one or more databases, and may be in processing communication with the appropriate CPU to perform the various data, processing functions. Such CPU, ROM and RAM may interconnected with each other. It may be a hard wired connection, a wireless connection or a combination. An input/output interface may interconnected as well to cooperate with any CPU, ROM and/or RAM (e.g., via a bus). One or more suitable input device may be provided for a user, e.g., a keyboard, a mouse, a touch screen, or otherwise. The output device may include a suitable display and the like, a memory composed of a hard disk and the like, and/or a communication link composed of a wired link, a wireless link or both. The communication link may interface or allow operation with other devices (not shown) via a network including the Internet.

Any suitable non-transitory recording medium may be employed. Such medium may be permanently loaded onto a device or may be loaded as needed, such as by a portable removable non-transitory recording media, such as a USB memory drive, a flash memory drive, a magnetic disk, an optical disk (CD-ROM (Compact Disk-Read Only Memory), DVD (Digital Versatile Disk)), a magnet-optical disk (MD (Mini-disk)), and traditional semiconductor memory. The storage medium may be resident on a user computing device, on a thermocycling instrument, on a server within a user's facility, and/or on a server at a remote facility (e.g., in a cloud storage facility).

As can be appreciated, among the advantages, and technical benefits realized from the present teachings is a system that enables fast heating and cooling of samples under tight temperature control in accordance with a user inputted protocol for polymerase chain reaction. It will be appreciated that the system taught herein is useful with a wide, range of commercially available chemical agents that facilitate PCR processing. However, it should be recognized that the rapid rates contemplated herein may not lend the disclosed instrument for use with certain chemical agents, such as agents that require a certain period of time for thermal processing in order for the agent to become sufficiently active. The skilled artisan should be able to ascertain appropriate agents to employ within the performance expected from the instrument herein. Alternatively, the skilled artisan could define appropriate protocols (e.g., to extend the time periods for stages), so that the agents can be used most effectively.

The instrument herein is believed suitable for use with a wide range of commercially available enzymes such as Pure recombinant high fidelity DNA polymerase from *Thermococcus kodakaraensis* KOD1, a *Pyrococcus*-like enzyme, or other suitable products offered under the names KOD from Toyobo, Platinum® Taq DNA Polymerase from Life Technologies Corp., Phusion® from New England BioLabs, Inc., SpeedStar™ from Westburg BV or Takara Bio Company, or the like. However, as to certain enzymes, it needs to be considered that there may be "time-release" activation associated with the enzyme. For example, the formulation of Amplitaq Gold® (from Applied Biosystems) requires about a 10 minute initial hot-start to activate sufficient enzyme amounts, with more enzyme activation needed in subsequent PCR cycles accomplished with 1 minute denaturation holds. Thus, the total run time is dominated by the time required for enzyme activation with ramp time savings having less impact. Though such an enzyme may be employed, a user will typically need to input one or more relatively long hold times. Other enzymes (e.g., DeepVent® from New England BioLabs, PFU from Strategene, or others) that are regarded as having relatively slow extension (copying of the DNA) rates may also dictate longer run times. It may also be possible to employ other agents for helping to expedite the activity of an enzyme. For example, for a primer annealing step, it may be possible to increase an amount of magnesium and PCR primer concentrations, in order to help expedite the process. It is generally expected that PCR primers that are used in slow PCR protocols can be directly applied to rapid PCR with optimization of annealing temperature, time, and concentrations.

For PCR probes (i.e. real-time fluorescent dyes/probes), any extra processing time that may be required will typically depend on the specifics of the probe. For example, a certain amount of time may be required for dyes to efficiently intercalate into double-stranded DNA (diffusion or reaction rate time). For probes such as molecular beacons, the association/disassociation of the probe to itself may require additional hold times. For Taqman probes, the exonuclease activity of the enzyme to break down the probe may require additional hold time. Accordingly, in designing a protocol suitable for use herein, it is contemplated that the user will take into account the relative performance characteristics of the agents, being employed along with the sample, and select appropriate (if any) protocol adjustments.

It will be appreciated that the instruments and other teachings herein have widespread application and may be used in the field of diagnosis of a disease, treatment of a disease, forensic analysis, genetics analysis or the like. Examples of uses may include medical diagnostics, reverse transcription PCR (RT-PCR), genetic fingerprinting/forensics (crime scene DNA), paternal testing, bacterial identification, free fetal DNA analysis, genetic screening for cancer or drug efficacy, genetic disease testing, molecular cloning and sequencing applications, gene expression, genome mapping, or HIV/TB diagnostics (infectious disease diagnostics). The instruments described herein may be utilized in conjunction with additional instruments for biological testing, such as those disclosed in U.S. Publication No. 2010/0291536 and PCT Publication No. WO2011/153244, the contents of these applications being hereby incorporated by reference for all purposes.

The thermocycler instrument herein and associated methods for using it may be adapted for many uses and such uses are contemplated within the scope of the teachings herein. Among such uses may be one or more of a quantitative PCR operation; an operation that employs one or more isothermal conditions for amplification; an operation that may be employed with one or more living cells or micro-organisms and/or for the identification of a bacteria, virus or other infectious agent; an operation in which the timing of the addition of a polymerase is selectively employed (e.g., a hot start PCR operation); an operation that employs multiple primer sets within a single PCR mixture (e.g., a multiplex PCR operation); and/or an operation that employs a single primer pair for amplifying multiple targets (e.g., a multiplex ligation-dependent probe amplification); an operation that employs gradually lowering annealing temperatures at later cycles (e.g., a step-down PCR operation). In one aspect of the teachings, it is envisioned that there may be a PCR operation that is performed to determine a load (e.g., a viral load or otherwise) for sortie infectious agent by the employment of a quantitative PCR approach (e.g., via a real-time analysis, using an optical detection technique).

EXAMPLES

Example heating and cooling protocols demonstrating speed of cycling and accuracy of heating and cooling to setpoint temperature are shown at examples 1 and 2 below.

Example 1

Stage 1: Heat/Cool to 95° C., hold for 0 seconds; Stage 2: Heat/Cool to 60° C. hold for 0 seconds; Repeat stage 1 and stage 2 for 30 cycles. The resulting time and temperature graphic data is shown at FIG. 4A.

Example 2

Stage 1: Heat/Cool to 95° C., hold for 30 seconds; Stage 2: Heat/Cool to 95° C., hold for 5 seconds; Stage 3: Heat/Cool to 60° C., hold for 5 seconds; Stage 4: Heat/Cool to 72° C., hold for 5 seconds; Stage 5: Heat/Cool to 72° C., hold for 5 seconds; Repeat stages 2, 3, and 4 for 30 cycles. The resulting time and temperature graphic data is shown at FIG. 4B.

Example 3

Stage 1: Heat/Cool to 95° C., hold for 10 seconds; Stage 2: Heat/Cool to 95° C., hold for 5 seconds; Stage 3: Heat/Cool to 55° C., hold for 5 seconds; Stage 4: Heat/Cool to 72° C., hold for 5 seconds; Stage 5: Heat/Cool to 95° C., hold for 4 seconds; Stage 6: Heat/Cool to 68° C., hold for 4 seconds; Stage 7: Heat/Cool to 90° C., hold for 3 seconds; Stage 8: Heat/Cool to 50° C., hold for 3 seconds; Repeat stages 1 through 8 for 3 cycles. The resulting time and temperature graphic data is shown at FIG. 4C.

General Comments

Though various of the above steps in the teachings herein are described as being performed by at least one controller within the thermocycler, such functions may alternatively or additionally be performed by a processor external of the thermocycler, such as by a processor of a computer that, is in signaling communication with the thermocycler. Further, reference in the teachings to "a controller" or "the controller" also contemplate a control system by which one or more control functions may spread among a plurality of control devices (e.g., electronic processors or other computer devices). For each of the above-described Formulae, the operator asterisk symbol (*) refers to a multiplication function, the operator (A) indicates that the following number is an exponent. Further, input and output values for temperature are in Centigrade.

The teachings herein pertain not only to novel, aspects of the thermocycler instrument (and methods of controlling it) as a whole, but also to the individual components. Thus for example, it is contemplated that sub-assemblies, and/or individual steps or sub-routines described herein are among the novel features of the teachings and may merit patent protection for themselves. Thus, the teachings herein envision that the sample holder is unique, as is its combination with one or more of flanking thermoelectric devices, at least one temperature sensor, and the described heat exchangers (and optionally any thermal paste or the like). The use of the disclosed sample tubes with such sample holder is also a unique feature, and may merit patent protection independent of other features herein. The software taught herein may merit patent protection independent of other features herein, or in combination with any suitable thermocycler instrument. Further, the control methodologies described herein are not limited to the specific thermocyclers described, but may be used with other thermocyclers.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

As to all of the foregoing general teachings, as used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples, of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight and vice versa. Thus, an expression in the Detailed Description of the Invention of a range in terms of at "x" parts by weight of the resulting polymeric blend composition also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Concentrations of ingredients identified in Tables herein may vary ±10%, or even 20% or more and remain within the teachings.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps, herein also contemplates embodiments that consist essentially of, or even consist of the elements, ingredients, components or steps. Plural elements, ingredients, components of steps can be provided by a single integrated element, ingredient, component or step. Alternatively, a single integrated element, ingredient, component or step might be divided into separate plural elements, ingredients, components or steps. The disclosure of "a" of "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

Even if not expressly stated, teachings from a description of one embodiment may be combined with teachings for other embodiments unless the description makes clear that such embodiments are mutually exclusive, or that the resulting combination would be clearly inoperative in the absence of unreasonable experimentation.

It is understood that the above description is intended to be illustrative and not restrictive. Many embodiments as well as many applications besides the examples provided will be apparent to those of skill in the art upon reading the above-description. The scope of the invention should, therefore, be determined hot with reference to the above description, but should instead be determined with reference to the appended claims, along with the full scope of equivalents to which such claims are entitled, the disclosures of all articles and references, including patent applications and publications, are incorporated by reference for all purposes, the omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A method for operating a thermocycler instrument for amplification by a polymerase chain reaction, comprising the steps of:
   a) operating the thermocycler instrument including:
      (i) a sample holder which is a block with a plurality of bores therein, wherein each bore is adapted to complementarily receive a sample tube,
      (ii) a pair of thermoelectric devices opposed and spaced apart having the sample holder disposed between, each of the thermoelectric devices having at least one heat exchanger,
      (iii) at least one first temperature sensor associated with the sample holder, and
      (iv) at least one second temperature sensor associated with the at least one beat exchanger,
   for causing at least one sample in the sample tube contained in the sample holder to undergo polymerase chain reaction amplification by repealed cycling between at least a denaturation heating stage and an annealing cooling stage;
   b) monitoring a first temperature corresponding with a temperature of the sample holder using the at least one first temperature sensor, and a second temperature corresponding with a temperature of the at least one heat exchanger and external of the sample holder using the at least one second temperature sensor, and wherein substantially real time temperature condition information obtained from the at least one first temperature sensor and the at least one second temperature sensor is employed and processed for delivering suitable power;
   c) dynamically controlling the power that is delivered to the pair of thermoelectric devices of the thermocycler instrument based upon the first temperature and the second temperature, wherein the dynamically controlling step (c) includes the steps of:
      (i) receiving at least one first setpoint temperature predetermined by a user, the at least one first setpoint temperature being a maximum temperature to which the at least one sample is to be heated for polymerase chain reaction denaturation of the at least one sample;

(ii) receiving at least one second setpoint temperature predetermined by the user, the at least one second setpoint temperature being a minimum temperature to which the at least one sample is to be cooled for annealing of the at least one sample;

(iii) receiving at least one first hold time corresponding with an amount of time predetermined by the user during which the temperature of the sample holder is maintained generally at the at least one first setpoint temperature;

(iv) receiving at least one second hold time corresponding with an amount of time predetermined by the user during which the temperature of the sample holder is maintained generally at the at least one second setpoint temperature;

(v) causing at least one of the thermoelectric devices to heat the sample holder;

(vi) receiving a first sensor signal from the at least one first temperature sensor corresponding with the temperature of the sample holder;

(vii) receiving a second sensor signal from the at least one second temperature sensor corresponding with the temperature of the at least one heat exchanger and is located externally of the sample holder;

(viii) determining a value of any first temperature offset amount (TOFFSET1) based upon the temperature reading from the at least one first and second temperature sensors;

(ix) causing heating of the sample holder until the sample holder reaches a first offset temperature that is below the first setpoint temperature by the first temperature offset amount;

(x) at the time the first offset temperature is reached, causing a cooling pulsation of at least one of the thermoelectric devices during the heating stage for a sufficient amount of time so that the temperature arrives within about 1° C. of the first setpoint temperature and further heating of the sample holder is interrupted;

(xi) causing the temperature to be maintained within about 1° C. of the first setpoint temperature for the first hold time;

(xii) causing at least one of the thermoelectric devices to cool the sample holder until the temperature of the sample holder reaches a second offset temperature that is above the second setpoint temperature by a second temperature offset (TOFFSET2) amount;

(xiii) receiving a temperature reading from the at least one first temperature sensor corresponding with the temperature of the sample holder;

(xiv) receiving a temperature reading from the at least one second temperature sensor corresponding with the temperature of the at least one heat exchanger and is located remotely from the sample holder;

(xv) determining a value of any second temperature offset amount (TOFFSET2) based upon the temperature reading from the at least one first and second temperature sensors;

(xvi) causing cooling of the sample holder until the sample holder reaches the second offset temperature that is above the second setpoint temperature by the second temperature offset amount;

(xvii) at the time when the second offset temperature is reached, causing a heating pulsation of at least one of the thermoelectric devices during the cooling stage for a sufficient amount of time so that the temperature arrives within about 1° C. of the second setpoint temperature and further cooling of the sample holder is interrupted;

(xviii) causing the temperature to be maintained within about 1° C. of the second setpoint temperature for the second hold time; and (xix) repeating at least steps (v)-(xviii) for a predetermined number of cycles until the amplification desired by the user is achieved.

2. The method of claim 1, wherein the dynamically controlling step includes controlling operation of one or more parameters of at least one of the thermoelectric devices.

3. The method of claim 1, wherein the dynamically controlling step includes controlling operation of the pair of thermoelectric devices and an alteration of the power that is delivered on a basis of repeatedly determining an offset temperature and controlling introduction of a respective heating pulsation during the annealing cooling stage, or cooling pulsation during the denaturation heating stage, on the basis of the offset temperature.

4. The method of claim 2, wherein the one or more parameters are selected from an amount of the power delivered to at least one of the thermoelectric devices, a polarity of at least one of the thermoelectric devices, a pulse width of the power being delivered to at least one of the thermoelectric devices, the time that the power is delivered, or any combination thereof.

5. The method of claim 3, wherein alteration of power includes altering an amount of the power delivered to each of the thermoelectric devices, a polarity of each of the thermoelectric devices, a pulse width of the power being delivered to each of the thermoelectric devices, the time that the power is delivered, or any combination thereof.

6. A method for operating a thermocycler instrument for amplification by a polymerase chain reaction, comprising the steps of, a) operating the thermocycler instrument including:
(i) a sample holder which is a block with a plurality of bores therein, wherein each bore is adapted to complementarily receive a sample tube,
(ii) a pair of thermoelectric devices opposed and spaced apart having the sample holder disposed between, each of the thermoelectric devices having at least one heat exchanger,
(iii) at least one first temperature sensor associated with the sample holder, and
(iv) at least one second temperature sensor associated with at least one of the at least one heat exchanger,
for causing at least one sample in the sample tube contained in the sample holder to undergo polymerase chain reaction amplification by repeated cycling between at least a denaturation heating stage and an annealing cooling stage;

b) monitoring a first temperature corresponding with the temperature of the sample holder using the at least one first temperature sensor, and a second temperature corresponding with the temperature of the at least one heat exchanger and external of the sample holder using the at least one second temperature sensor, and wherein substantially real time temperature condition information obtained from the at least one first temperature sensor and the at least one second temperature sensor is employed and processed for delivering suitable power;

c) dynamically controlling the power that is delivered to the pair of thermoelectric devices of the thermocycler instrument based upon the first temperature and the second temperature,
   wherein the dynamically controlling step includes controlling operation of one or more parameters of at least one of the thermoelectric devices;
   wherein the dynamically controlling step includes controlling operation of the pair of thermoelectric devices and an alteration of the power that is delivered on a basis of repeatedly determining an offset temperature and controlling introduction of a respective heating pulsation during the annealing cooling stage, or cooling pulsation during the denaturation heating stage, on the basis of the offset temperature;
   wherein alteration of power includes altering an amount of power delivered to each of the thermoelectric devices, a polarity of each of the thermoelectric devices, a pulse width of power being delivered to each of the thermoelectric devices, the time that power is delivered, or any combination thereof; and
   wherein the dynamically controlling step (c) includes the steps of:
   (i) receiving at least one first setpoint temperature predetermined by a user, the at least one first setpoint temperature being a maximum temperature to which the at least one sample is to be heated for polymerase chain reaction denaturation of the at least one sample;
   (ii) receiving at least one second setpoint temperature predetermined by the user, the at least one second setpoint temperature being a minimum temperature to which the at least one sample is to be cooled for annealing of the at least one sample;
   (iii) receiving at least one first hold time corresponding with an amount of time predetermined by the user during which the temperature of the sample holder is maintained generally at the at least one first setpoint temperature;
   (iv) receiving at least one second hold time corresponding with an amount of time predetermined by the user during which the temperature of the sample holder is maintained generally at the at least one second setpoint temperature;
   (v) causing each of the thermoelectric devices to heat the sample holder;
   (vi) receiving a first sensor signal from the at least one first temperature sensor corresponding with the temperature of the sample holder;
   (vii) receiving a second sensor signal from the at least one second temperature sensor corresponding with the temperature of the at least one heat exchanger that is located externally of the sample holder;
   (viii) determining a value of any first temperature offset amount (TOFFSET1) based upon a temperature reading from the at least one first and second temperature sensors;
   (ix) causing heating of the sample holder until the sample holder reaches a first offset temperature that is below the first setpoint temperature by the first temperature offset amount;
   (x) at the time the first offset temperature is reached, causing a cooling pulsation of the thermoelectric devices during the heating stage for a sufficient amount of time so that the temperature arrives within about 1° C. of the first setpoint temperature and further heating of the sample holder is interrupted;
   (xi) causing the temperature to be maintained within about 1° C. of the first setpoint temperature for the first hold time;
   (xii) causing at least one of the thermoelectric devices to cool the sample holder;
   (xiii) receiving a temperature reading from the at least one first temperature sensor corresponding with if the temperature of the sample holder;
   (xiv) receiving a temperature reading from the at least one second temperature sensor corresponding with the temperature of the at least one heat exchanger that is located remotely from the sample holder;
   (xv) determining a value of any second temperature offset amount (TOFFSET2) based upon the temperature reading from the at least one first and second temperature sensors;
   (xvi) causing cooling of the sample holder until the sample holder reaches a second offset temperature that is above the second setpoint temperature by the second temperature offset amount;
   (xvii) at the time when the second offset temperature is reached, causing a heating pulsation of the thermoelectric devices during the cooling stage for a sufficient amount of time so that the temperature arrives within about 1° C. of the second setpoint temperature and further cooling of the sample holder is interrupted;
   (xviii) causing the temperature to be maintained within about 1° C. of the second setpoint temperature for the second hold time; and
   (xix) repeating steps (v)-(xviii) for a predetermined number of cycles until the amplification desired by the user is achieved.

7. The method of claim 1, wherein at least one of the steps of causing the temperature to be maintained includes monitoring the temperature and applying a pulse width modulated signal to at least one of the thermoelectric devices.

8. The method of claim 6, wherein at least one of the steps of causing the temperature to be maintained includes monitoring the temperature and applying a pulse width modulated voltage signal to the thermoelectric devices.

9. The method of claim 1, wherein the thermocycler instrument is adapted to operate and is operated for heating the sample holder at a rate of at least about 8° C./second.

10. The method of claim 1, wherein the thermocycler instrument is adapted to operate and is operated for cooling at a rate of at least about 6° C./second.

11. The method of claim 1, wherein the thermocycler instrument is capable of a total runtime of less than or equal to 30 minutes for completed amplification.

12. A method for controlling operation of a thermocycler instrument for amplification by polymerase chain reaction, comprising the steps of:
   a) introducing at least one biological sample and at least one fluorescent agent into a thermocycler instrument that includes:
      (i) at least one pair of thermoelectric devices which are opposing and spaced apart and have one or more associated heat exchangers;
      (ii) at least one sample holder which is a substantially solid metal block and is disposed in thermal conducting relation with and between the at least one pair of thermoelectric devices, wherein the sample holder includes:

a plurality of bores defined therein and each bore is adapted to receive a sample contained in a tube, and at least one sensor bore to receive a temperature sensor within the sample holder;

(iii) at least one first temperature sensor that is located in the sensor bore and is adapted to monitor a first temperature of the at least one sample holder;

(iv) at least one second temperature sensor located externally of the sample holder and in a sensing relationship with at least one of the one or more heat exchangers to monitor at least one second temperature;

(iv) a detector;

b) receiving at least one first setpoint temperature of at least about 85° C., to which the at least one biological sample is to be heated in the sample holder for polymerase chain reaction denaturation, and at least one second setpoint temperature of below about 70° C. to which the biological sample held in the sample holder is to be cooled for annealing of the at least one biological sample;

c) maintaining a heating rate of at least about 8° C./second until a first offset temperature amount of no more than about 7.5° C. below the first setpoint temperature is reached for the sample holder;

d) when the first offset temperature is reached, pulse cooling the sample holder to slow the heating rate until the sample holder is within about 1° C. of the first setpoint temperature;

e) maintaining a cooling rate of at least about 6° C./second until a second offset temperature by no more than about 7.5° C. above the second setpoint temperature is reached for the sample holder;

f) when the second offset temperature is reached, pulse heating the sample holder to slow the cooling rate until the sample holder is within about 1° C. of the second setpoint temperature;

g) monitoring a first temperature corresponding with a temperature of the sample holder with the at least one first temperature sensor and a second temperature corresponding with a temperature of at least one of the one or more heat exchangers with the at least one second temperature sensor;

h) adjusting an amount of time, a temperature or both at which the steps of pulse cooling, the pulse heating or both commence based upon the first temperature and the second temperature; and i) detecting amplification in a real-time mariner and repeating steps (b)-(h) for a predetermined number of cycles until the amplification desired by a user is achieved.

13. The method of claim 12, wherein the receiving step (b) includes receiving at least one first hold time for which the at least one first setpoint temperature is desired by the user to remain substantially constant, and at least one second hold time for which the at least one second setpoint temperature is desired by the user to remain substantially constant.

14. The method of claim 13, wherein a step of pulse width modulation is employed, while monitoring at least the temperature of the sample holder for delivering power to the pair of thermoelectric devices for the duration of the first and second hold time in order to maintain substantially constant temperatures at each of the first and second setpoint temperatures.

* * * * *

UNITED STATES PATENT AND TRADEMARK OFFICE
CERTIFICATE OF CORRECTION

PATENT NO. : 9,737,891 B2
APPLICATION NO. : 13/484963
DATED : August 22, 2017
INVENTOR(S) : Joel TerMaat et al.

Page 1 of 1

It is certified that error appears in the above-identified patent and that said Letters Patent is hereby corrected as shown below:

In the Claims

Column 68, Line 44, Claim 6 delete "one beat exchanger" insert --one heat exchanger--
Column 68, Line 47, Claim 6 delete "by repealed cycling" and insert --by repeated cycling--
Column 72, Line 9, Claim 6 delete "if" after the phrase "corresponding with"
Column 74, Line 15, Claim 18 delete "a real-time mariner" and insert --a real-time manner--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*